(12) United States Patent
    Morselli Gysi et al.

(10) Patent No.:    US 12,670,969 B2
(45) Date of Patent:      Jun. 30, 2026

(54) NETWORK MEDICINE FRAMEWORK FOR IDENTIFYING DRUG REPURPOSING OPPORTUNITIES

(71) Applicants:Northeastern University, Boston, MA (US); Scipher Medicine Corporation, Waltham, MA (US); The Brigham and Women's Hospital, Inc., Boston, MA (US); President and Fellows of Harvard College, Cambridge, MA (US)

(72) Inventors: Deisy Morselli Gysi, Boston, MA (US); Albert-László Barábasi, Brookline, MA (US); Italo Faria do Valle, Boston, MA (US); Onur Varol, Cambridge, MA (US); Xiao Gan, Boston, MA (US); Asher Ameli, Kenmore, WA (US); Joseph Loscalzo, Boston, MA (US); Marinka Zitnik, Boston, MA (US); Susan Ghiassian, Coquitlam (CA)

(73) Assignees: Northeastern University, Boston, MA (US); Scipher Medicine Corporation, Waltham, MA (US); The Brigham and Women's Hospital, Inc., Boston, MA (US); President and Fellows of Harvard College, Cambridge, MA (US)

( * ) Notice: Subject to any disclaimer, the term of this patent is extended or adjusted under 35 U.S.C. 154(b) by 1179 days.

(21) Appl. No.: 17/456,519

(22) Filed: Nov. 24, 2021

(65) Prior Publication Data

US 2022/0165352 A1     May 26, 2022

Related U.S. Application Data

(60) Provisional application No. 63/118,557, filed on Nov. 25, 2020.

(51) Int. Cl.
    *G16B 15/30*       (2019.01)
    *G16B 45/00*       (2019.01)
            (Continued)

(52) U.S. Cl.
    CPC ............. *G16B 15/30* (2019.02); *G16B 45/00* (2019.02); *G16H 20/10* (2018.01); *G16H 70/40* (2018.01)

(58) Field of Classification Search
    CPC .......... G16B 15/30; G16B 45/00; G16B 5/00; G16H 20/10; G16H 70/40; G16H 50/80
    See application file for complete search history.

(56) References Cited

U.S. PATENT DOCUMENTS

2016/0246919 A1*   8/2016   Wang ..................... G06Q 10/04
2017/0364630 A1*   12/2017   Rubin ................... C12Q 1/701
             (Continued)

FOREIGN PATENT DOCUMENTS

CN      112037856 A   *   12/2020   ............. G06N 3/047
CN      112216396 A   *   1/2021   ............. G16H 50/70
             (Continued)

OTHER PUBLICATIONS

Yue, X., Wang, Z., Huang, J., Parthasarathy, S., Moosavinasab, S., Huang, Y., Lin, S.M., Zhang, W., Zhang, P., Sun, H. (Jun. 12, 2019). Graph Embedding on Biomedical Networks: Methods, Applications, and Evaluations. arXiv preprint arXiv:1906.05017v1. (Year: 2019).*

(Continued)

*Primary Examiner* — Jesse P Frumkin

(74) *Attorney, Agent, or Firm* — Hamilton, Brook, Smith & Reynolds, P.C.

(57)        ABSTRACT

Methods and systems for generating drug repurposing predictions for a disease caused by a pathogen, such as a novel pathogen, are provided. A multi-modal system includes a (Continued)

SARS-CoV-2
Viral Interactome      Human Interactome

○   SARS-CoV-2 (Viral) Protein
   Host (Human) Protein
   Viral Target (Host Protein Targeted by Virus)
   Direct Target Drug
   Network-based Drug protein-protein interaction network (PPI), a graph neural network (GNN), a diffusion module, a proximity module, and an aggregation module. The GNN is configured to predict new edges between candidate drug nodes and disease nodes in an embedded representation of the PPI to produce a decoded embedding space. The diffusion module is configured to determine a proximity distance for pairs of nodes in the PPI, and the proximity module is configured to determine a proximity distance for pairs of nodes in the PPI, each pair comprising a pathogen-protein node and a drug-protein node. A ranked list of candidate drugs predicted to be effective in treatment of the disease based on candidate drug lists generated by the other modules is generated by the aggregation module.

18 Claims, 43 Drawing Sheets
(38 of 43 Drawing Sheet(s) Filed in Color)

(51) Int. Cl.
    *G16H 20/10* (2018.01)
    *G16H 70/40* (2018.01)

(56) References Cited

U.S. PATENT DOCUMENTS

| | | | | |
|---|---|---|---|---|
| 2020/0225242 | A1* | 7/2020 | Haas | G16B 5/00 |
| 2021/0081717 | A1* | 3/2021 | Creed | G06N 5/022 |
| 2021/0303536 | A1* | 9/2021 | Alesiani | G06F 16/9024 |
| 2022/0277813 | A1* | 9/2022 | Veselkov | G16B 5/00 |
| 2023/0117881 | A1* | 4/2023 | Sztyler | G16B 40/20 |
| | | | | 706/15 |

FOREIGN PATENT DOCUMENTS

| | | | | | |
|---|---|---|---|---|---|
| CN | 112331257 | A | * | 2/2021 | G06N 3/045 |
| CN | 111916145 | B | * | 3/2022 | G06N 3/045 |
| WO | WO-2020070485 | A1 | * | 4/2020 | G16B 5/00 |

OTHER PUBLICATIONS

Gysi, D.M., Valle, Í.D., Zitnik, M., Ameli, A., Gan, X., Varol, O., Sanchez, H., Baron, R.M., Ghiassian, S.D., Loscalzo, J., Barabási, A. (Apr. 15, 2020). Network Medicine Framework for Identifying Drug Repurposing Opportunities for COVID-19. arXiv preprint arXiv:2004.07229v1. (Year: 2020).*
Hu, Fan, et al. "Structure enhanced protein-drug interaction prediction using transformer and graph embedding." 2020 IEEE international conference on bioinformatics and biomedicine (BIBM). IEEE, 2020. (Year: 2020).*
CN112037856 WIPO Machine Translation (Year: 2020).*
CN112216396 WIPO Machine Translation (Year: 2021).*
CN112331257 WIPO Machine Translation (Year: 2021).*
CN111916145 WIPO Machine Translation (Year: 2022).*
Aggarwal, C. C. et al., "On the Surprising Behavior of Distance Metrics in High Dimensional Space," in *Database theory—ICDT*, 200, (Eds. den Bussche, J. & Vianu, V.) pp. 420-434 (Berlin: Springer, 2001).
Aguila, E. J. T. & I. H. Y. Cua, "Repurposed GI Drugs in the Treatment of COVID-19," *Digestive Diseases and Sciences*, 65: 2452-2453 (2020).
Ailon, N. et al., "Proofs of Conjectures in Aggregating Inconsistent Information: Ranking and Clustering," *Proceedings of the 37th Annual ACM Symposium on Theory of Computing*, pp. 684-693 (May 2005). doi:10.1145/1060590.1060692.
Alanis-Lobato, G. et al., "HIPPIE v2.0: enhancing meaningfulness and reliability of protein-protein interaction networks," *Nucleic Acids Research*, 45: D408-D414 (2016).

Alonso-López, D. et al., "APID database: redefining protein-protein interaction experimental evidences and binary interactomes," *Database*, 2019: 1-8 (2019).
Beigel, J. H. et al., "Remdesivir for the Treatment of Covid-19—Final Report," *The New England Journal of Medicine*, 383(19): 1813-1826 (2020) NEJMoa2007764. doi:10.1056/NEJMoa2007764.
Broucr, K. et al., "InnatcDB: systems biology of innate immunity and beyond-recent updates and continuing curation," *Nucleic Acids Research*, 41: D1228-1233 (2013).
Caldera, M. et al., "Interactome-based approaches to human disease," *Current Opinion in Systems Biology*, 3: 88-94 (2017).
Campillos, M. et al., "Drug Target Identification Using Side-Effect Similarity," *Science (New York, N.Y.)*, 321: 263-266 (2008).
Cao, M. et al., "Going the Distance for Protein Function Prediction: A New Distance Metric for Protein Interaction Networks," *PLoS One*, 8(10): e76339, 12 pages (2013). doi:10.1371/journal.pone. 0076339.
Casas, A. I. et al., "From single drug targets to synergistic network pharmacology in ischemic stroke," *Proceedings of the National Academy of Sciences of the United States of America*, 116(14): 7129-7136 (2019).
Casella, G. & E. Moreno, "Assessing Robustness of Intrinsic Tests of Independence in Two-Way Contingency Tables," *Journal of the American Statistical Association*, 104: 1261-1271 (2012).
Chatr-Aryamontri, A. et al., "The BioGRID interaction database: 2017 update," *Nucleic Acids Research*, 45: D369-D379 (2017).
Chen, N. et al., "Epidemiological and clinical characteristics of 99 cases of 2019 novel coronavirus pneumonia in Wuhan, China: a descriptive study," *Lancet*, 395: 507-513 (2020).
Cheng, F. et al., "Quantitative network mapping of the human kinome interactome reveals new clues for rational kinase inhibitor discovery and individualized cancer therapy," *Oncotarget*, 5(11): 3697-3710 (2014).
Cheng, F. et al., "Network-based approach to prediction and population-based validation of in silico drug repurposing," *Nature Communications*, 9, 1-12 (2018).
Cheng, F. et al., "Network-based prediction of drug combinations," *Nature Communications*, 10: 11 pages (2019).
Coppersmith, D. et al., "Ordering by weighted No. of wins gives a good ranking for weighted tournaments," *Proceedings of the Annual ACM-SIAM Symposium on Discrete Algorithms*, 776-782 (2006). doi:10.1145/1109557.1109642.
Corsello, S. M. et al., "The Drug Repurposing Hub: a next-generation drug library and information resource," *Nature Medicine*, 23(4): 405-408 (2017).
Cowley, M. J. et al., "PINA v2.0: mining interactome modules," *Nucleic Acids Research*, 40: D862-D865 (2012).
Dakshanamurthy, S. et al., "Predicting New Indications for Approved Drugs Using a Proteo- Chemometric Method," *Journal of Medicinal Chemistry*, 55(15): 6832-6848 (2012).
Dudley, J. T. et al., "Computational repositioning of the anticonvulsant topiramate for inflammatory bowel discasc," *Science Translational Medicine*, 3(96): 96ra76, 12 pages (2011).
Dwork, C. et al., "Rank Aggregation Methods for the Web," in *Proceedings of the 10th International Conference on World Wide Web*, WWW 2001: 613-622 (Association for Computing Machinery, Inc, 2001). doi:10.1145/371920.372165.
Eilbeck, K. et al., "Settling the score: variant prioritization and Mendelian disease," *Nature Rev Genet.*, 18(10): 599-612 (2017). https:/doi.org/10.1038/nrg.2017.52.
Ellinger, B. et al., "Identification of inhibitors of SARS-CoV-2 in-vitro cellular toxicity in human (Caco-2) cells using a large scale drug repurposing collection," *Research Square*: 1-19 (2020). doi:10. 21203/RS.3.RS-23951/V1.
Giacomelli, A. et al., "Self-reported Olfactory and Taste Disorders in Patients with Severe Acute Respiratory Coronavirus 2 Infection: A Cross-sectional Study," *Clin. Infect. Dis.*, 17(15): 888-889 (2020). doi:10.1093/cid/ciaa330.
Gilmer, J. et al., "Neural Message Passing for Quantum Chemistry," in *ICML*: 1263-1272 (2017).
Glorot, X. & Y. Bengio, "Understanding the difficulty of training deep feedforward neural networks," in *AISTATS*: 249-256 (2010).

(56) References Cited

OTHER PUBLICATIONS

Gordon, D. E. et al., "A SARS-CoV-2-Human Protein-Protein Interaction Map Reveals Drug Targets and Potential Drug-Repurposing," *bioRxiv* 2020.03.22.002386 (2020). doi:10.1101/2020.03.22.002386 (No Date Available).

Gordon, D. E. et al., "A SARS-CoV-2 protein interaction map reveals targets for drug repurposing," *Nature*, 583: 459-468 (2020).

Grasselli, G. et al., "Baseline Characteristics and Outcomes of 1591 Patients Infected With SARS-CoV-2 Admitted to ICUs of the Lombardy Region, Italy," *JAMA*, 8 pages (2020). doi:10.1001/jama.2020.5394.

Greene, C. S. & B. F. Voight, "Pathway and network-based strategies to translate genetic discoveries into effective therapies," *Human Molecular Genetics*, 25(R2): R94-R98 (2016).

Guala, D. & E. L. L. Sonnhammer, "A large-scale benchmark of gene prioritization methods," *Scientific Reports*, 7: 1-10 (2017).

Gulbahce, N. et al., "Viral Perturbations of Host Networks Reflect Disease Etiology," *PLoS Computational Biology*, 8(6): e1002531, 10 pages (2012).

Guney, E. et al., "Network-based in silico drug efficacy screening," *Nature Communications*, 7: 10331 (2016).

Gysi, D. M. et al., "Network Medicine Framework for Identifying 1 Drug Repurposing Opportunities for COVID-19," *PNAS*, vol. 118, No. 19, e2025581118, 11 pages (2021).

Hamilton, W. et al., "Embedding Logical Queries on Knowledge Graphs," in *NIPS*, 2026-2037 (2018).

Hamilton, W. et al., "Inductive Representation Learning on Large Graphs," in *NIPS*: 1024-1034 (2017).

Hidalgo, C. A. et al., "A Dynamic Network Approach for the Study of Human Phenotypes," *PLoS Comput. Biol.*, 5(4): e1000353, 11 pages (2009).

Honma, M. et al., "Effect of an oral gold compound, auranofin, on non-specific bronchial hyperresponsiveness in mild asthma," *Thorax*, 49: 649-651 (1994) https:/doi.org/10.1136/thx.49.7.649.

Hornbeck, P. V. et al., "PhosphoSitePlus, 2014: mutations, PTMs and recalibrations," *Nucleic Acids Research*, 43: D512-D520 (2015).

Huang, C. et al., "Clinical features of patients infected with 2019 novel coronavirus in Wuhan, China," *Lancet*, 395: 497-506 (2020).

Huang, K. & M. Zitnik, "Graph Meta Learning via Local Subgraphs," *34th Conference on Neural Information Processing Systems (NeurIPS 2020)*, Vancouver, CA, 13 pages.

Huttlin, E. L. et al., "Architecture of the human interactome defines protein communities and disease networks," *Nature*, 545(7655): 505-509 (2017).

Kass, R. E. & A. E. Raftery, "Bayes Factors," *Journal of the American Statistical Association*, 90(430): 773-795 (1995).

Keiser, M. J. et al., "Predicting new molecular targets for known drugs," *Nature*, 462(7270): 175-181 (2009).

Kingma, D. P. & J. L. Ba, "Adam: A Method for Stochastic Optimization," 15 pages, arXiv:1412.6980 (2014).

Lee, D.-S. et al., "The implications of human metabolic network topology for disease comorbidity," *Proc. Natl. Acad. Sci. U. S. A.*, 105(29): 9880-9885 (2008).

Li, T. et al., "A scored human protein-protein interaction network to catalyze genomic interpretation," *Nat. Methods*, 14(1): 61-64 (2016).

Licata, L. et al., "MINT, the molecular interaction database: 2012 update," *Nucleic Acids Res.*, 40: D857-D861 (2012).

Lin, K. & P. Gallay, "Curing a viral infection by targeting the host: The example of cyclophilin inhibitors," *Antiviral Research*, 99: 68-77 (2013).

Lonsdale, J. et al., "The Genotype-Tissue Expression (GTEx) project," *Nature Genetics*, 45(6): 580-585 (2013).

Luck, K. et al., "A reference map of the human binary protein interactome," *Nature*, 580(7803): 402-408 (2020).

Luck, K. et al., "Proteome-scale human interactomics," *Trends in Biochemical Sciences*, 42(5): 342-354 (2017).

Menche, J. et al., "Uncovering disease-disease relationships through the incomplete interactome," *Science (New York, N.Y.)*, 347(6224): 1257601, 15 pages (2015).

Meyer, M. J. et al., "INstruct: a database of high-quality 3D structurally resolved protein interactome networks," *Bioinformatics* 29(12): 1577-1579 (2013).

Meyer, M. J. et al., "Interactome INSIDER: a structural interactome browser for genomic studies," *Nat. Methods* 15(2): 107-114 (2018).

Paik, H. et al., "Repurpose terbutaline sulfate for amyotrophic lateral sclerosis using electronic medical records," *Scientific Reports*, 5: 8580, 8 pages (2015).

Park, J. et al., "The impact of cellular networks on disease comorbidity," *Mol. Syst. Biol., 5, Article* 262, 14 pages (2009).

Patten J. J. et al., "Multidose evaluation of 6,710 drug repurposing library identifies potent SARS-CoV-2 infection inhibitors in vitro and in vivo," bioRxiv [Preprint] (2021).

Pedregosa, F. et al., "Scikit-learn: Machine Learning in Python," *J. Mach. Learn. Res.*, 12: 2825-2830 (2011).

Reilly, B., "Social Choice in the South Seas: Electoral Innovation and the Borda Count in the Pacific Island Countries," *International Political Science Review*, 23(4): 355-372 (2002). doi:10.1177/0192512102023004002.

Ritz, C. & J. C. Streibig, "Bioassay Analysis using R," *J. Stat. Softw.*, 12(5): 22 pages (2005).

Ritz, C. et al., "Dose-Response Analysis Using R," *PLoS One*, 10: e0146021, 13 pages (2015).

Riva, L. et al., "Discovery of SARS-CoV-2 antiviral drugs through large-scale compound repurposing," *Nature*, 586: 113-119 (2020). doi:10.1038/s41586-020-2577-1.

Sadegh, S. et al., "Exploring the SARS-CoV-2 virus-host-drug interactome for drug repurposing," *Nature Communications*, 11: 1-9 (2020).

Schalekamp, F. et al., "Rank Aggregation: Together We're Strong," *Proc of 11th ALENEX*, 18: 38-51 (2009).

Silverman, E. K. et al., "Molecular networks in Network Medicine: Development and applications." *Wiley Interdisciplinary Reviews: Systems Biology and Medicine*, e1489, 38 pages (2020). doi:10.1002/wsbm.1489.

Sing, T. et al., "ROCR: visualizing classifier performance in R," *Bioinformatics*, 21(20): 3940-3941 (2005). https:/doi.org/10.1093/bioinformatics/bti623.

Srivastava, N. et al., "Dropout: A Simple Way to Prevent Neural Networks from Overfitting," *Journal of Machine Learning Research*, 15: 1929-1958 (2014).

Veličković, P. et al., "Graph Attention Networks," *ICLR*, 12 pages (2018).

Wan, C. et al., "Panorama of ancient metazoan macromolecular complexes," *Nature*, 525(7569): 339-344 (2015).

Wang, D. et al., "Clinical Characteristics of 138 Hospitalized Patients with 2019 Novel Coronavirus-Infected Pneumonia in Wuhan, China," *J. Am. Med. Assoc.*, 323(11): 1061-1069 (2020). doi:10.1001/jama.2020.1585.

Wang, M. et al., "Remdesivir and chloroquine effectively inhibit the recently emerged novel coronavirus (2019-nCoV) in vitro," *Cell Research*, 30: 269-271 (2020).

Wickham, H., *ggplot2. An implementation of the grammar of graphics*, Wiley Interdisciplinary Reviews: Computational Statistics, 48 pages (2011). https:/doi.org/10.1002/wics.147.

Wishart, D. S. et al., "DrugBank 5.0: a major update to the DrugBank database for 2018," *Nucleic Acids Research*, 46: D1074-D1082 (2018).

Ying, R. et al., "GNNExplainer: Generating Explanations for Graph Neural Networks," 33rd Conference on Neural Information Processing Systems (NeurIPS 2019), Vancouver, Canada, 12 pages (2019).

Zhou, Y. et al., "Network-based drug repurposing for novel coronavirus 2019-nCoV/SARS-CoV-2," *Cell Discovery*, 6: 1-18 (2020).

Zitnik, M. et al., "Machine Learning for Integrating Data in Biology and Medicine: Principles, Practice, and Opportunities," *An International Journal on Information Fusion*, 50: 71-91 (2019).

Zitnik, M. et al., "Modeling polypharmacy side effects with graph convolutional networks," *Bioinformatics*, 34: i457-i466 (2018).

Zitnik, M et al., "Prioritizing network communities," *Nature Communications*, 9: 2544 (2018).

Zolotareva, O. & M. Kleine, "A Survey of Gene Prioritization Tools for Mendelian and Complex Human Diseases," *Journal of Integrative Bioinformatics*, 16, 20 pages (2019).

(56)　　　　　　References Cited

OTHER PUBLICATIONS

Hoffman, et al., "SARS-CoV-2 Cell Entry Depends on ACE2 and TMPRSS2 and Is Blocked by a Clinically Proven Protease Inhibitor," CellPress, 181, 271-280, Apr. 16, 2020.

* cited by examiner

A1 —— A2 ---- A3 ---- A4 ——
D1 —— D2 —— D3 —— D4 —— D5 ——
P1 —— P2 —— P3 —— cRANK ——          Dowdall ----
Average rank ——          Union(top-K) ----
Borda count ——

| | | |
|---|---|---|
| FIG. 12A | FIG. 12B | FIG. 12G |
| FIG. 12C | FIG. 12D | |
| FIG. 12E | FIG. 12F | |
| FIG. 12H | FIG. 12I | |

FIG. 12

| | | |
|---|---|---|
| FIG. 13A | FIG. 13B | FIG. 13G |
| FIG. 13C | FIG. 13D | |
| FIG. 13E | FIG. 13F | |
| FIG. 13H | FIG. 13I | |

FIG. 13

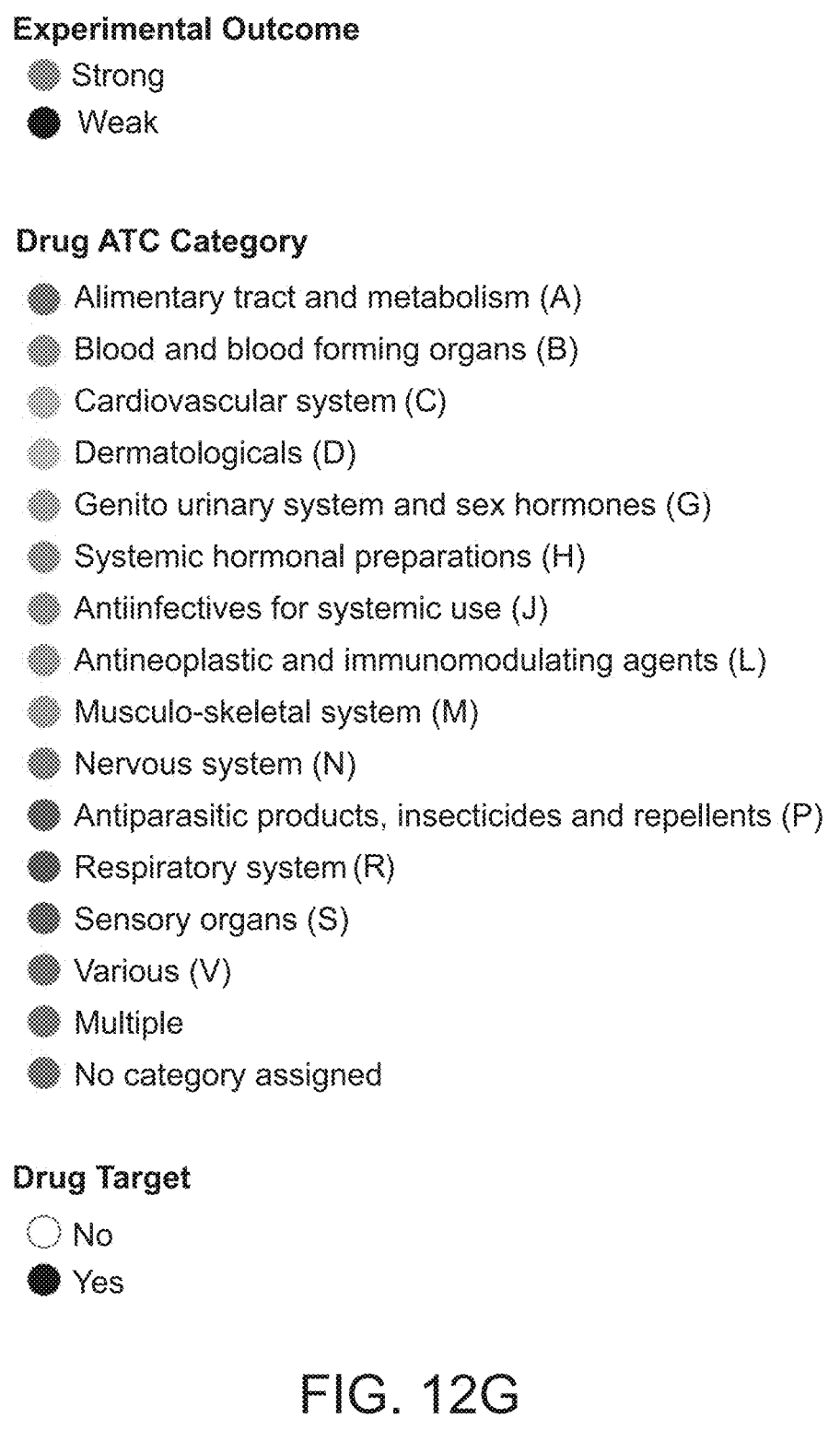

Experimental Outcome

⬤ Strong

⬤ Weak

Drug ATC Category

⬤ Alimentary tract and metabolism (A)

⬤ Blood and blood forming organs (B)

⬤ Cardiovascular system (C)

⬤ Dermatologicals (D)

⬤ Genito urinary system and sex hormones (G)

⬤ Systemic hormonal preparations (H)

⬤ Antiinfectives for systemic use (J)

⬤ Antineoplastic and immunomodulating agents (L)

⬤ Musculo-skeletal system (M)

⬤ Nervous system (N)

⬤ Antiparasitic products, insecticides and repellents (P)

⬤ Respiratory system (R)

⬤ Sensory organs (S)

⬤ Various (V)

⬤ Multiple

⬤ No category assigned

Drug Target

◯ No

⬤ Yes

FIG. 12G

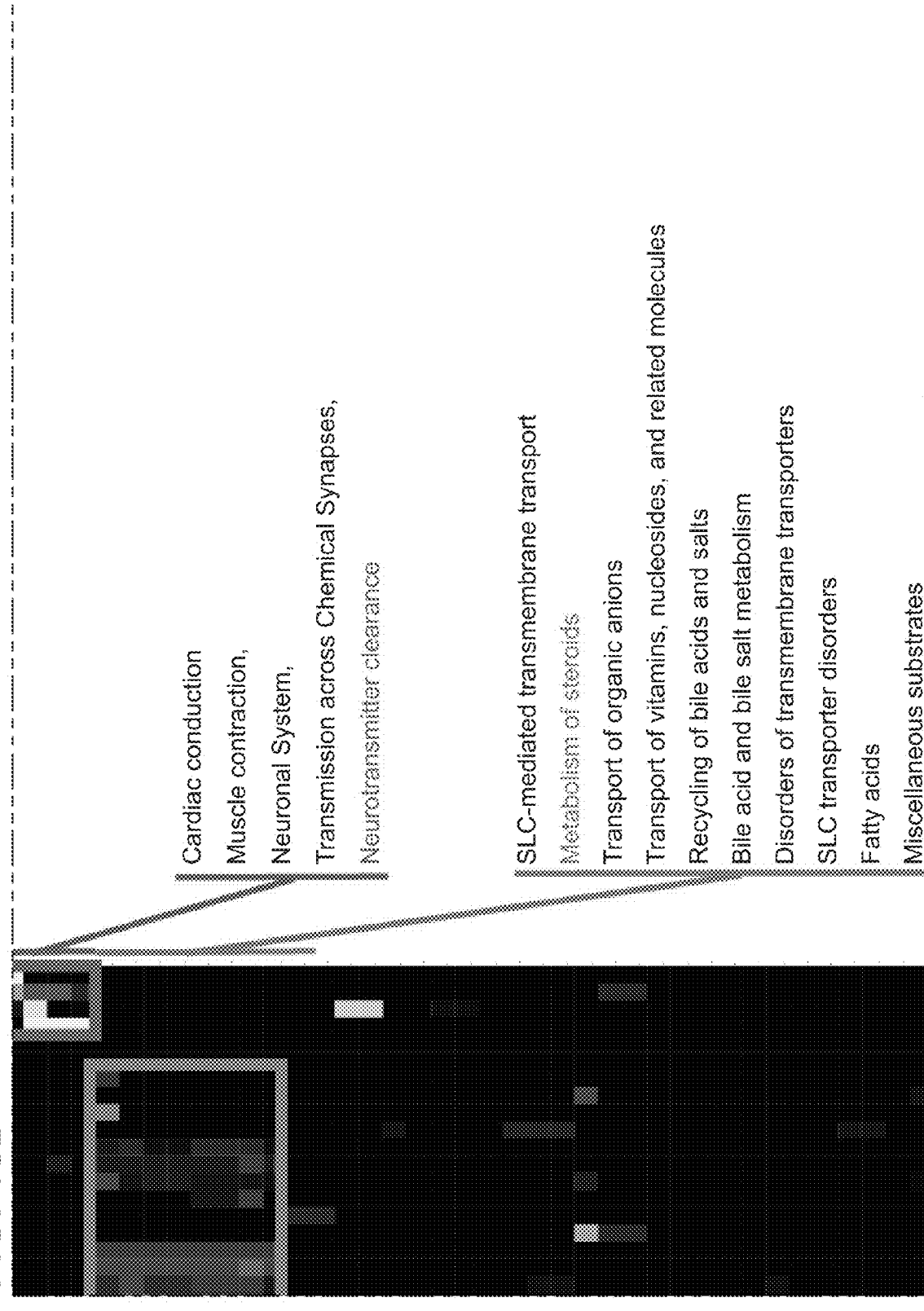

FIG. 13D

Cardiac conduction
Muscle contraction,
Neuronal System,
Transmission across Chemical Synapses,
Neurotransmitter clearance SLC-mediated transmembrane transport
Metabolism of steroids
Transport of organic anions
Transport of vitamins, nucleosides, and related molecules
Recycling of bile acids and salts
Bile acid and bile salt metabolism
Disorders of transmembrane transporters
SLC transporter disorders
Fatty acids
Miscellaneous substrates

Figure 13G:
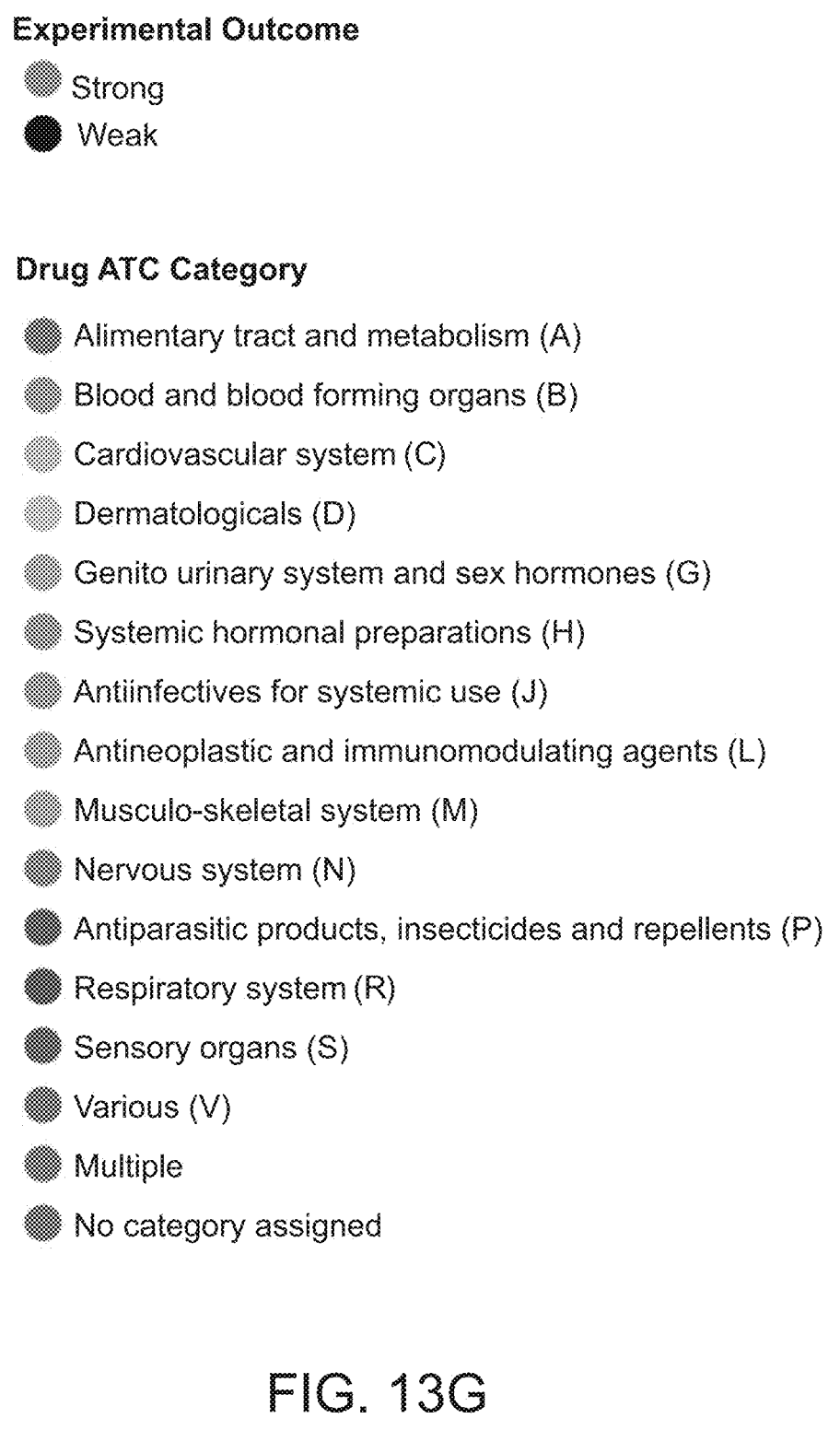

Experimental Outcome

⬤ Strong

⬤ Weak

Drug ATC Category

⬤ Alimentary tract and metabolism (A)

⬤ Blood and blood forming organs (B)

⬤ Cardiovascular system (C)

⬤ Dermatologicals (D)

⬤ Genito urinary system and sex hormones (G)

⬤ Systemic hormonal preparations (H)

⬤ Antiinfectives for systemic use (J)

⬤ Antineoplastic and immunomodulating agents (L)

⬤ Musculo-skeletal system (M)

⬤ Nervous system (N)

⬤ Antiparasitic products, insecticides and repellents (P)

⬤ Respiratory system (R)

⬤ Sensory organs (S)

⬤ Various (V)

⬤ Multiple

⬤ No category assigned

Table 1. Drugs with positive experimental outcomes

| CRank | Drug name | CRank | Drug name |
|---|---|---|---|
| 5 | Chloroquine | 569 | Amiodarone |
| 6 | Rifabutin | 577 | Duloxetine |
| 9 | Rifaximin | 585 | Toremifene |
| 10 | Azelastine | 586 | Afatinib |
| 16 | Folic acid | 601 | Amitriptyline |
| 32 | Methotrexate | 626 | Meclizine |
| 33 | Digoxin | 635 | Valsartan |
| 44 | Hydroxychloroquine | 651 | Eletriptan |
| 50 | Omeprazole | 673 | Sotalol |
| 113 | Clobetasol propionate | 678 | Thioridazine |
| 118 | Auranofin | 695 | Chlorcyclizine |
| 120 | Vinblastine | 707 | Omacetaxine mepesuccinate |
| 199 | Fluvastatin | 721 | Candesartan |
| 210 | Clomifene | 742 | Mianserin |
| 233 | Ibuprofen | 755 | Clofazimine |
| 235 | Ivermectin | 767 | Chlorpromazine |
| 243 | Atorvastatin | 772 | Imipramine |
| 253 | Pralatrexate | 830 | Promazine |
| 263 | Cobimetinib | 900 | L-Alanine |
| 269 | Hydralazine | 917 | Moxifloxacin |
| 297 | Propranolol | 933 | Tasimelteon |
| 317 | Osimertinib | 995 | Vandetanib |
| 348 | Vincristine | 1000 | Azilsartan medoxomil |
| 367 | Doxazosin | 1020 | Frovatriptan |
| 397 | Rosiglitazone | 1034 | Zolmitriptan |
| 398 | Aminolevulinic acid | 1035 | Procarbazine |
| 423 | Pitavastatin | 1093 | Asenapine |
| 431 | Tenoxicam | 1107 | Dyclonine |
| 438 | Quinidine | 1140.5 | Clemastine |
| 456 | Sertraline | 1194 | Prochlorperazine |
| 460 | Ingenol mebutate | 1222 | Miglustat |
| 463 | Norelgestromin | 1224 | Prenylamine |
| 493 | Sildenafil | 1276 | Dalfampridine |
| 499 | Eliglustat | 1314 | Cinchocaine |
| 518 | Ulipristal | 1355 | Methotrimeprazine |
| 553 | Cinacalcet | 1396 | Methylthioninium |
| 556 | Perphenazine | 1403 | Metixene |
| 558 | Idarubicin | 1443 | Trifluoperazine |
| 564 | Perhexiline | | |

FIG. 19

Table 2. CRank predictions for drug repurposing

| CRank | Drug name | CRank | Drug name | CRank | Drug name |
|---|---|---|---|---|---|
| 1 | Ritonavir | 34 | Gefitinib | 67 | Mebendazole |
| 2 | Isoniazid | 35 | Enzalutamide | 68 | Adenosine |
| 3 | Troleandomycin | 36 | Theophylline | 69 | Mesalazine |
| 4 | Cilostazol | 37 | Bicalutamide | 70 | Nevirapine |
| 5 | Chloroquine | 38 | Trabectedin | 71 | Belinostat |
| 6 | Rifabutin | 39 | Nelfinavir | 72 | Mitomycin |
| 7 | Flutamide | 40 | Beclomethasone dipropionate | 73 | Malathion |
| 8 | Dexamethasone | 41 | Fluconazole | 74 | Ixekizumab |
| 9 | Rifaximin | 42 | Aminoglutethimide | 75 | Vindesine |
| 10 | Azelastine | 43 | Ifosfamide | 76 | Secukinumab |
| 11 | Crizotinib | 44 | Hydroxychloroquine | 77 | Rifapentine |
| 12 | Urea | 45 | Acetic acid | 78 | Bilastine |
| 13 | Methylprednisolone | 46 | Cyclophosphamide | 79 | Clotrimazole |
| 14 | Dimethyl sulfoxide | 47 | Methimazole | 80 | Erlotinib |
| 15 | Cortisone acetate | 48 | Teniposide | 81 | Panobinostat |
| 16 | Folic acid | 49 | Ribavirin | 82 | Warfarin |
| 17 | Celecoxib | 50 | Omeprazole | 83 | Busulfan |
| 18 | Betamethasone | 51 | Chlorambucil | 84 | Goserelin |
| 19 | Prednisolone | 52 | Citalopram | 85 | Hydroxyurea |
| 20 | Mifepristone | 53 | Bortezomib | 86 | Temsirolimus |
| 21 | Budesonide | 54 | Leflunomide | 87 | Abiraterone |
| 22 | Prednisone | 55 | Dimethyl fumarate | 88 | Miconazole |
| 23 | Oxiconazole | 56 | Teriflunomide | 89 | Ketorolac |
| 24 | Megestrol acetate | 57 | Colchicine | 90 | Exemestane |
| 25 | Idelalisib | 58 | Phenylbutyric acid | 91 | Oxymetholone |
| 26 | Econazole | 59 | Progesterone | 92 | Pentamidine |
| 27 | Rabeprazole | 60 | Triamcinolone | 93 | Diclofenac |
| 28 | Quinine | 61 | Medroxyprogesterone acetate | 94 | Aminophylline |
| 29 | Ticlopidine | 62 | Tioguanine | 95 | Loratadine |
| 30 | Hydrocortisone | 63 | Quercetin | 96 | Fexofenadine |
| 31 | Lansoprazole | 64 | Clobetasol | 97 | Terbinafine |
| 32 | Methotrexate | 65 | Letrozole | 98 | Verapamil |
| 33 | Digoxin | 66 | Etoposide | 99 | Clopidogrel |
| | | | | 100 | Rivaroxaban |

NETWORK MEDICINE FRAMEWORK FOR IDENTIFYING DRUG REPURPOSING OPPORTUNITIES

RELATED APPLICATION

This application claims the benefit of U.S. Provisional Application No. 63/118,557, filed on Nov. 25, 2020, the entire teachings of which are incorporated herein by reference.

GOVERNMENT SUPPORT

This invention was made with government support under Grant Nos. HL132825, HG007690, HL108630, HL119145, HL155107 and HL155096 awarded by the National Institutes of Health, and Grant Nos. 2030459 and 2033384 awarded by the National Science Foundation. The government has certain rights in the invention.

BACKGROUND

The disruptive nature of the COVID-19 pandemic has unveiled the need for the rapid development, testing, and deployment of new drugs and cures. Given the compressed timescales of a pandemic as illustrated by the COVID-19 pandemic, the de novo drug development process, which typically lasts a decade or longer, may not be feasible for addressing future variants of COVID-19 or for addressing future pandemics. A time-efficient strategy relies on drug repurposing (or repositioning), helping identify among the compounds approved for clinical use the few that may also have a therapeutic effect in patients with COVID-19. Yet, the lack of reliable repurposing methodologies has resulted in a winner-takes-all pattern, where more than one-third of registered clinical trials focus on hydroxychloroquine or chloroquine, siphoning away resources from testing a wider range of potentially effective drug candidates. While a full unbiased screening of all approved drugs could identify all possible treatments, given the combination of its high cost, extended timeline, and exceptionally low success rate, there exists a need for efficient strategies that enable effective drug prioritization.

Existing drug repurposing algorithms rank drugs based on one or multiple streams of information, such as molecular profiles, chemical structures, adverse profiles, molecular docking, electronic health records, pathway analysis, genome wide association studies (GWAS), and network perturbations. Yet, typically, only a small subset of the top candidates is validated experimentally, hence a true predictive power of existing repurposing algorithms remains unknown.

There exists a need for improved drug repurposing methods and systems, with improved predictive power.

SUMMARY

Methods and systems for generating drug repurposing predictions for a disease caused by a pathogen and for improving the accuracy of drug repurposing predictions for a novel pathogen are provided.

A multi-modal system for generating drug repurposing predictions for a disease caused by a pathogen includes a protein-protein interaction network defining pathogen-protein interactions for the pathogen and drug-protein interactions for a plurality of candidate drugs. The system further includes a graph neural network comprising an embedded representation of the protein-protein interaction network, the embedded representation including candidate drug nodes and disease nodes. The graph neural network is configured to predict new edges between the candidate drug nodes and disease nodes to produce a decoded embedding space. A first list comprising a subset of the plurality of candidate drugs is identifiable from the decoded embedding space. The system further includes a diffusion module and a proximity module. The diffusion module is configured to determine a diffusion metric for pairs of nodes in the protein-protein interaction network, each pair comprising a pathogen-protein node and a drug-protein node. A second list comprising a subset of the plurality of candidate drugs is identifiable from the determined diffusion metrics. The proximity module is configured to determine a proximity distance for pairs of nodes in the protein-protein interaction network, each pair comprising a pathogen-protein node and a drug-protein node. A third list comprising a subset of the plurality of candidate drugs is identifiable from the determined proximity distances. The system further includes an aggregation module configured to generate a ranked list of candidate drugs predicted to be effective in treatment of the disease based on the first, second, and third lists.

The aggregation module can be configured to generate the ranked list based on a consensus ranking of the first, second, and third lists. Each of the first, second, and third lists can comprise at least two sub-lists. For example, the first list can include two or more sub-lists based on varying decoding parameters applied to the decoded embedding space. The second list can include two or more sub-lists based on varying distance or divergence parameters. The third list can include two or more sub-lists based on varying drug-inclusion criteria.

The graph neural network can be untrained for the pathogen. For example, the graph neural network can be a graph convolutional neural network trained by a zero-shot learning strategy or a few-shot learning strategy.

The diffusion metric can be a diffusion state distance between nodes, a divergence between vector representations of nodes, or a combination thereof.

The protein-protein interaction network can be a human interactome.

The pathogen can be a novel pathogen.

A multi-modal method for generating drug repurposing predictions for a disease related to a pathogen includes, with a protein-protein interaction network defining pathogen-protein interactions for the pathogen and drug-protein interactions for a plurality of candidate drugs, and, in a graph neural network comprising an embedded representation of the protein-protein interaction network, the embedded representation including candidate drug nodes and disease nodes: predicting new edges between the candidate drug nodes and disease nodes to produce a decoded embedding space, and identifying a first list comprising a subset of the plurality of candidate drugs being from the decoded embedding space. The method further includes, in a diffusion module: determining a diffusion metric for pairs of nodes in the protein-protein interaction network, each pair comprising a pathogen-protein node and a drug-protein node, and identifying a second list comprising a subset of the plurality of candidate drugs from the determined diffusion metrics. The method further includes, in a proximity module: determining a proximity distance for pairs of nodes in the protein-protein interaction network, each pair comprising a pathogen-protein node and a drug-protein node, and identifying a third list comprising a subset of the plurality of candidate drugs from the determined proximity distances.

The method further includes generating a ranked list of candidate drugs predicted to be effective in treatment of the disease based on the first, second, and third lists.

A method of improving accuracy of drug repurposing predictions for a novel pathogen includes, with a protein-protein interaction network defining pathogen-protein interactions for the pathogen and drug-protein interactions for a plurality of candidate drugs, and, in a graph neural network comprising an embedded representation of the protein-protein interaction network, the embedded representation including candidate drug nodes and disease nodes: predicting new edges between the candidate drug nodes and disease nodes to produce a decoded embedding space, and identifying a first list comprising a subset of the plurality of candidate drugs being from the decoded embedding space. The method further includes, in a diffusion module: determining a diffusion metric for pairs of nodes in the protein-protein interaction network, each pair comprising a pathogen-protein node and a drug-protein node, and identifying a second list comprising a subset of the plurality of candidate drugs from the determined diffusion metrics. The method further includes, in a proximity module: determining a proximity distance for pairs of nodes in the protein-protein interaction network, each pair comprising a pathogen-protein node and a drug-protein node, and identifying a third list comprising a subset of the plurality of candidate drugs from the determined proximity distances. The method further includes generating a consensus ranking of candidate drugs predicted to be effective in treatment of the disease based on the first, second, and third lists, the consensus ranking providing for improved predictive power over each of the first, second, and third lists.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a flow diagram of a study, and FIG. 1B is a representation of outputs produced at each phase of the study. FIG. 1C is an illustration of integration of pathogen-proteins and drug-proteins in a protein-protein interaction network. Following the publication of host-pathogen protein-protein interactions (D. E. Gordon et al., A SARS-CoV-2 protein interaction map reveals targets for drug repurposing. *Nature* 583, 459-468 (2020)), three drug repurposing algorithms, relying on artificial intelligence (AI) (pipelines A1-A4), network diffusion (D1-D5) and proximity (P1-P3), were combined, resulting in 12 predictive ranking lists (alternatively referred to herein as pipelines), shown in FIG. 1B. Each pipeline (A1-A4, D1-D5, P1-P3) offered predictions for a different number of drugs. We then identified 918 drugs for which all pipelines but P3 offered predictions, and experimentally validated their effect on the virus in VeroE6 cells. The experimental lists (E918, E74 in FIG. 1B) and clinical trial list (CT415 in FIG. 1B) offered the ground truth for validation and rank aggregation. Direct target drugs bind either to a viral protein (D1) or to a host protein target of the viral proteins (D2). Network drugs (D3), in contrast, bind to the host proteins and limit viral activity by perturbing the host subcellular network.

FIG. 2A is a schematic of the disease module in an interactome. Proteins targeted by SARS-CoV-2 are not distributed randomly in the human interactome, but form a large connected component (LCC) of 208 proteins, and multiple small subgraphs, shown in FIG. 2A. Almost all proteins in the SARS-CoV-2 LCC are also expressed in the lung tissue, potentially explaining the effectiveness of the virus in causing pulmonary manifestations of the disease. FIG. 2B is a graph of a random expectation of the LCC size. As illustrated in FIG. 2B, the observed COVID-19 LCC, whose size is indicated by the arrow, is larger than expected by chance (Z-score=1.65). FIG. 2C is a heatmap of the Kendall $\tau$ statistic showing that the ranking list predicted by the different methods (AI, Diffusion, Proximity, shown in FIG. 1B) are not correlated. However, high correlations among the individual ranking list predicted by the same predictive method were observed.

FIG. 3A is a compound graph of examples of dose-response curves for eight of the 918 experimentally validated drugs (see J. J. Patten et al., Multidose evaluation of 6,710 drug repurposing library identifies potent SARS-CoV-2 infection inhibitors in vitro and in vivo. bioRxiv [Preprint] (2021)), illustrating the four observed outcomes (strong (S), weak (W), cytotoxic (C) and no-effect (N)). VeroE6 cells were challenged in vitro with SARS-CoV-2 virus and treated with the drug over a range of doses (from 8 nM to 8 μM). A two-step drug-response model (see Example 18, herein) was used to classify each drug into Strong, Weak, Cytotoxic or No-Effect categories, according to their response to the drug in different doses and cell and viral reduction. FIG. 3B illustrates the sub-network formed by the targets of the 77 S&W drugs within the interactome. The link corresponds to binding interactions. Proteins identified in purple are targeted by S drugs only; proteins identified in orange are targeted by W drugs only; and proteins targeted by both S&W drugs are shown as pie charts, proportional to the number of targets in each category. FIG. 3C is a graph of proximity scores. The targets of N drugs have a positive proximity Z-Score to the COVID-19 module, meaning they are further from the COVID-19 module than random expectation. In contrast, the targets of S&W drugs are more proximal (closer) to the COVID-19 module than expected by chance, suggesting that their COVID-19 vicinity contribute to their ability to alter the virus's ability to infect the cells.

FIGS. 4A and 4B are plots of AUC (Area under the Curve) results, FIGS. 4C and 4D are plots of precision at 100, and FIGS. 4E and 4F are plots of recall at 100, for the twelve pipelines tested for drug repurposing, using as a gold standard the S&W drugs in E918 (left column) and drugs under clinical trials for treating COVID-19 as of Apr. 15, 2020 (CT415, right column). FIGS. 4G and 4H are graphs of the top K precision and recall for the different rank aggregation methods (connected points), compared to the individual pipelines (empty symbols) documenting the consistent predictive performance of CRank. Similar results are shown for two other datasets in FIGS. 14A-14H.

FIG. 7 provides a visualization of the learned embedding space. The points each represent a drug (in blue) or a disease (in orange). If a drug and a disease are embedded close together in this space, this means the local interaction neighborhoods of the drug and the disease in the multimodal graph are predictive of whether the drug can treat the disease.

FIG. 8A is graph of distributions of the sizes of the subnetworks' (A1-A4, D1-D5, and P1-P3) predictions. The sizes vary according to the method. The AI methods have a smaller variance in size, while methods based on proximity tend to have higher variances. FIG. 8B is a diagram illustrating gene overlap of the methods involved with subgraphs for each method. Proximity and Diffusion based methods explore the protein-protein interaction network (PPI) in a vaster and diverse way than the AI methods. FIG. 8C is a graph illustrating that methods inside the same pipeline tend to select similar genes, the similarity of selected genes across methods is different (Jaccard Index), those genes also do not lie in similar neighborhoods (similarity), meaning that not only do the genes not overlap across methods, but the vicinity the methods explored are also different. FIG. 8D is a plot of another measure used to understand methods similarity involved using a Principal Component Analysis (PCA) of gene drug pairs, showing that AI methods are fairly consistent in in what they observe, and, similarly, P1 and P2. Diffusion methods have a higher variance in gene-drug pair predictions and have a larger spread of their module; as expected, P3 is far from other proximity measures.

FIG. 9A is a schematic showing the network pattern represented by each quadrant; FIGS. 9B, 9C, and 9D are plots for subgraphs in the AI, Diffusion, Proximity pipelines, respectively. Each method's subgraphs locate in different regions in the plot, suggesting that they use complimentary regions of the PPI to make predictions.

FIGS. 14A and 14B are plots of AUC (Area under the Curve) results, FIGS. 14C and 14D are plots of precision at 100, and FIGS. 14E and 14F are plots of recall at 100, for the twelve pipelines tested for drug repurposing, using as a gold standard the S&W drugs in E74 (left panel figures, experimentally validated dataset from expert curation and drug selection) and CT615 (right panel figures, drugs in clinical trials as of Jul. 15, 2020). FIGS. 14G and 14H are graphs of the top precision and recall for the different rank aggregation methods (connected points), compared to the individual pipelines (empty symbols) documenting the consistent predictive performance of CRank. CT06 presents, in most cases, higher hit rates, precision and recalls when compared to E74.

FIG. 18 is a table of drugs with positive experimental outcomes. The list includes 77 drugs with a positive outcome (S&W) from in vitro screen. Drug response classification was obtained by a two-step model for drug response (see Example 18, herein). Drugs in purple show strong effect (S), and in orange show weak effect (W).

FIG. 19 is a table of CRank predictions for drug repurposing. The list includes the top 100 consensus predictions of the drug-repurposing pipelines aggregated using the CRank algorithm. The top 100 drugs contain 9 drugs with positive experimental outcomes (S&W), 3 of which are among the top 10 drugs. Drugs in purple correspond to strong outcomes (S), in orange to weak outcomes (W), in green to cytotoxic drugs, and nonhighlighted drugs have shown no effect (N) in VeroE6 cells.

DETAILED DESCRIPTION

A description of example embodiments follows.

Systems and methods are provided for generating drug repurposing predictions for a disease caused by a pathogen. The provided systems and methods can provide for improved accuracy over existing drug repurposing prediction methods and can be used to generate predictions for a novel pathogen.

Figure 15:
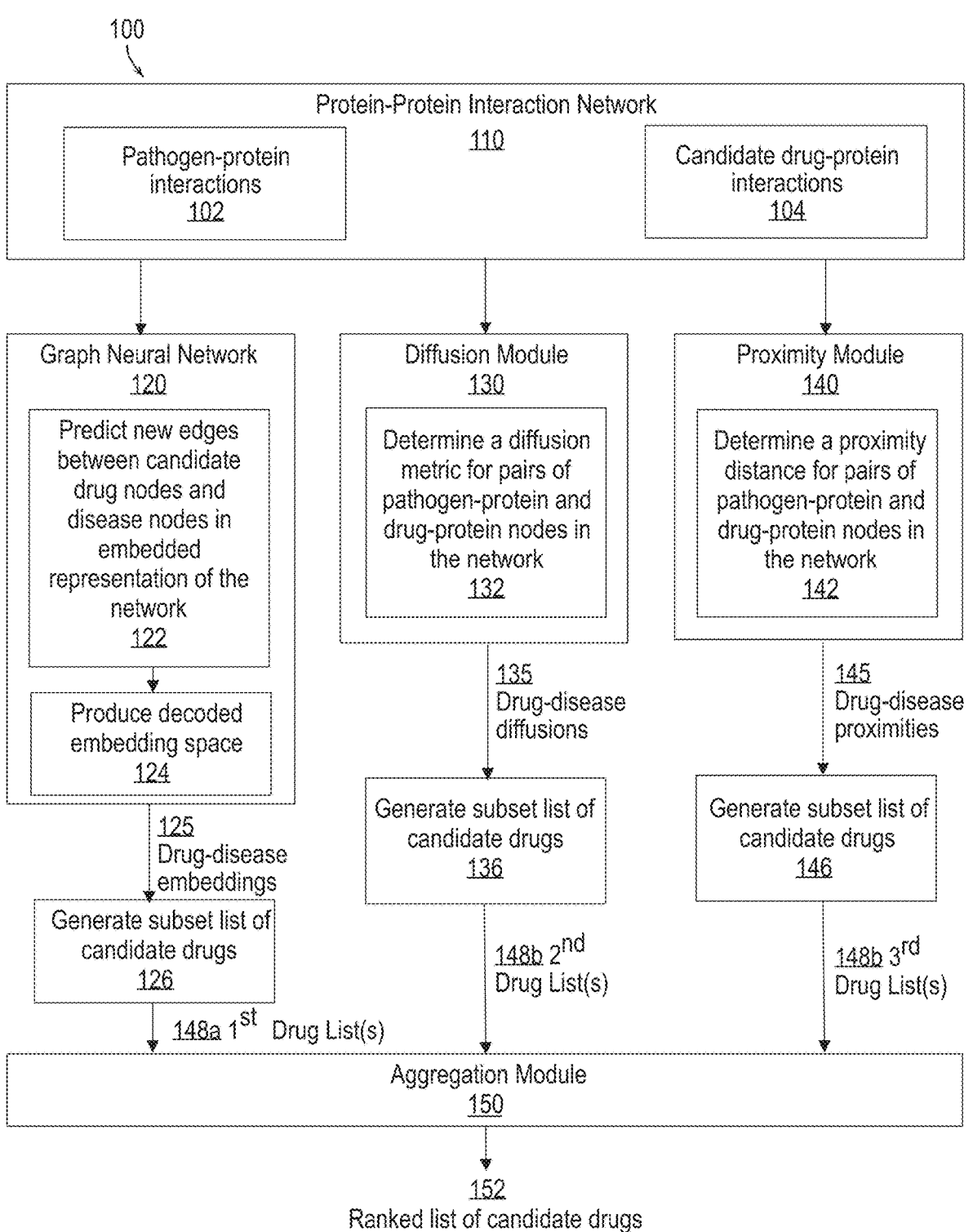
FIG. 15 is a diagram of a multi-modal method for generating drug repurposing predictions for a disease caused by a pathogen and for improving the accuracy of drug repurposing predictions for a novel pathogen.

An example method 100 is shown in FIG. 15. A protein-protein interaction network 110 includes a model of pathogen-protein interactions 102 for a pathogen and a model of drug-protein interactions 104 for a plurality of candidate drugs. The protein-protein interaction network can be, for example, a human interactome. An example of a protein-protein interaction network (PPI) and human interactome is further described in Example 7, herein.

With the protein-protein interaction network 110, a multi-modal process is performed with use of a graph neural network 120, a diffusion module 130, and a proximity module 140.

The graph neural network 120 includes an embedded representation of the protein-protein interaction network (not shown), the embedded representation including candidate drug nodes and disease nodes. The graph neural network 120 is configured to predict (122) new edges between the candidate drug nodes and disease nodes to produce (124) a decoded embedding space Based on drug-disease embeddings 125 from the decoded embedding space 124, the method 100 generates a first list 148a of a subset of the plurality of candidate drugs (126).

The graph neural network 120 can be, for example, a graph convolutional neural network. The pathogen can be a novel pathogen. Under such circumstances, a training dataset for the neural network can lack labelled samples for a class for which the neural network is expected to make predictions. The graph neural network can be trained to meta-learn on an incomplete or scarcely-labeled protein-protein interaction network to provide for predictions for a new, unseen class (e.g., a class of drugs predicted to be effective in treatment for a novel pathogen, such as COVID-19). The graph neural network can be trained by a zero-shot learning strategy or a few-short learning strategy. As used herein, the term "zero-shot learning strategy" means a strategy in which machine learning occurs with no labelled samples for a class, and "few-shot learning strategy" means a strategy in which machine learning occurs with few labelled samples for a class. A description of an example zero-shot learning strategy for a graph neural network is described in Example 11, herein. Additional examples and description of zero-shot learning and few-shot learning strategies for graph neural networks are described in Huang K and Zitnik M, Graph Meta Learning via Local Subgraphs, 34th Conference on Neural Information Processing Systems (NeurIPS 2020), Vancouver, CA.

The diffusion module 130 is configured to determine (132) a diffusion metric for pairs of nodes in the protein-protein interaction network. Each pair of nodes includes a pathogen-protein node and a drug-protein node. Based on determined drug-disease diffusions 135, the method 100 generates a second list 148b of a subset of the plurality of candidate drugs (136). The diffusion metric can be, for example, a diffusion state distance between nodes, a divergence between vector representations of nodes, or a combination thereof. A description of example methods of determining diffusion metrics for pairs of nodes is described in Example 12, herein.

The proximity module 140 is configured to determine a proximity distance for pairs of nodes in the protein-protein interaction network (142). Each pair of nodes includes a pathogen-protein node and a drug-protein node. Based on determined drug-disease proximities 145, the method 100 generates a third list 148c of a subset of the plurality of candidate drugs (146). A description of example methods of determining proximity distances for pairs of nodes is described in Example 13, herein.

An aggregation module 150 is configured to generate a ranked list 152 of candidate drugs predicted to be effective in treatment of the disease based on the first, second, and third lists 148a-c. For example, the aggregation module 150 can be configured to generate the ranked list 152 based on a consensus ranking of the first, second, and third lists 148a-c. A description of example methods of aggregating lists generated from a graph neural network, diffusion module, and proximity module is described in Examples 22-26, herein. The aggregation module 150 can output a list of candidate drugs, for example, as shown in FIG. 19.

The aggregated ranking can provide for improved predictions of drugs that may be effectively repurposed, particularly for novel pathogens, over existing drug repurposing methods.

Each of the first, second, and third lists 148a-c can include two or more sub-lists (not shown), or pipelines, of candidate drugs based on varying parameters applied in each module. For example, the first list 148a, as identified from the graph neural network 120, can include sub-lists based on varying decoding parameters applied to the decoded embedding space 125. Examples of varying decoding parameters and multiple pipelines are described in Example 11, herein. As further examples, the second list 148b, as identified from the diffusion module 130, can include sub-lists based on varying distance or divergence parameters; and, the third list 148c, as identified from the proximity module 140, can include sub-lists based on varying drug-inclusion criteria. Examples of varying distance and divergence parameters, of varying drug-inclusion criteria, and of multiple pipelines are described in Examples 12 and 13, herein. The terms "first," "second," and "third" are provided to distinguish the lists 148a-c generated by each of the respective modules 120, 130, 140 and do not impart any meaning with regard to timing or priority of list generation or consideration.

The COVID-19 pandemic has demanded the rapid identification of drug-repurposing candidates. Network medicine provides a framework for a series of quantitative approaches and predictive tools to study host-pathogen interactions, unveil molecular mechanisms of infection, and identify comorbidities. The systems and methods described herein adapt and improve upon network-based toolsets toward providing for a rapid identification of drug repurposing candidates. Example systems and methods are further described in the Exemplification section herein, where the systems and methods were applied to identify drug repurposing candidates for COVID-19.

The provided systems and methods make use of three network-based drug repurposing strategies, including network proximity, diffusion, and AI-based metrics, which, in an example use, allowed for a ranking of all approved drugs based on their likely efficacy for COVID-19 patients. The provided systems and methods aggregate predictions from the three strategies, and, in the example use, arrived at 81 promising repurposing candidates for COVID-19. The accuracy of the predictions was validated using drugs currently in clinical trials, and an expression-based validation of selected candidates suggests that these drugs, with known toxicities and side effects, can be moved to clinical trials rapidly.

The provided systems and methods advantageously provide for a unique combination approach to derive a list of ranked drugs that potentially have a therapeutic effect for treating a disease caused by a novel pathogen, such as COVID-19. The combination of network methods advantageously provides for improved predictive power over individual and pre-existing network methods.

In the past decade, network medicine has developed and validated multiple predictive algorithms for drug repurposing, exploiting the sub-cellular network-based relationship between a drug's targets and disease genes. As further described in the Exemplification section herein, a multimodal method including artificial intelligence, network diffusion, and network proximity methods was created. Initially, each method (i.e., artificial intelligence, network diffusion, and network proximity methods) was tasked with ranking 6,340 drugs for their expected efficacy against SARS-CoV-2. To test the predictions, 918 drugs that we experimentally screened in VeroE6 cells were used as ground truth, as well as a list of drugs under clinical trial, which captured the medical community's assessment of drugs with potential COVID-19 efficacy. It was found that, while most algorithms have predictive power, no single method offered consistently reliable outcomes across all datasets and metrics.

A multi-modal approach that fuses the predictions of all algorithms was created, and it was found that a consensus among the different predictive methods consistently exceeds the performance of the best individual pipelines. It was also found that 76 of the 77 drugs that successfully reduced viral infection do not bind the proteins targeted by SARS-CoV-2, indicating that these drugs rely on network-based mechanisms that cannot be identified using docking-based strategies. These advances offer a methodological pathway to identify repurposable drugs for future pathogens and neglected diseases underserved by the costs and extended timeline of de novo drug development.

Figure 16:
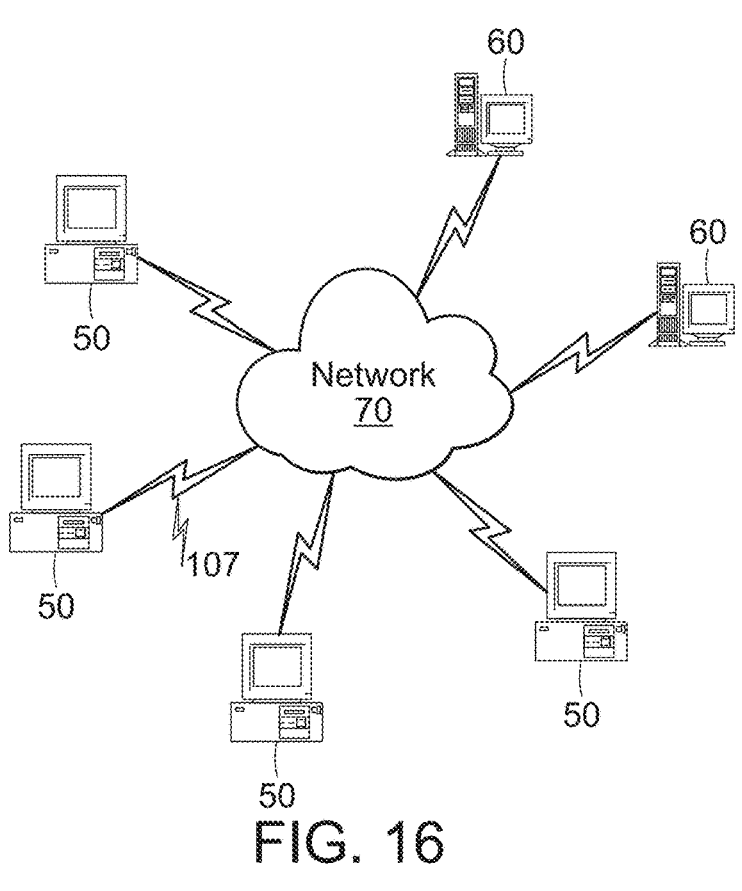
FIG. 16 is a schematic view of a computer network environment in which embodiments of the present invention may be deployed.

FIG. 16 illustrates a computer network or similar digital processing environment in which the systems and methods described may be implemented. Client computer(s)/devices/exercise apparatuses 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, cloud computing servers or service, Local area or Wide area networks, and gateways that currently use respective protocols (TCP/IP, Bluetooth, etc.) to communicate with one another. Other electronic device/computer network architectures are suitable.

Figure 17:
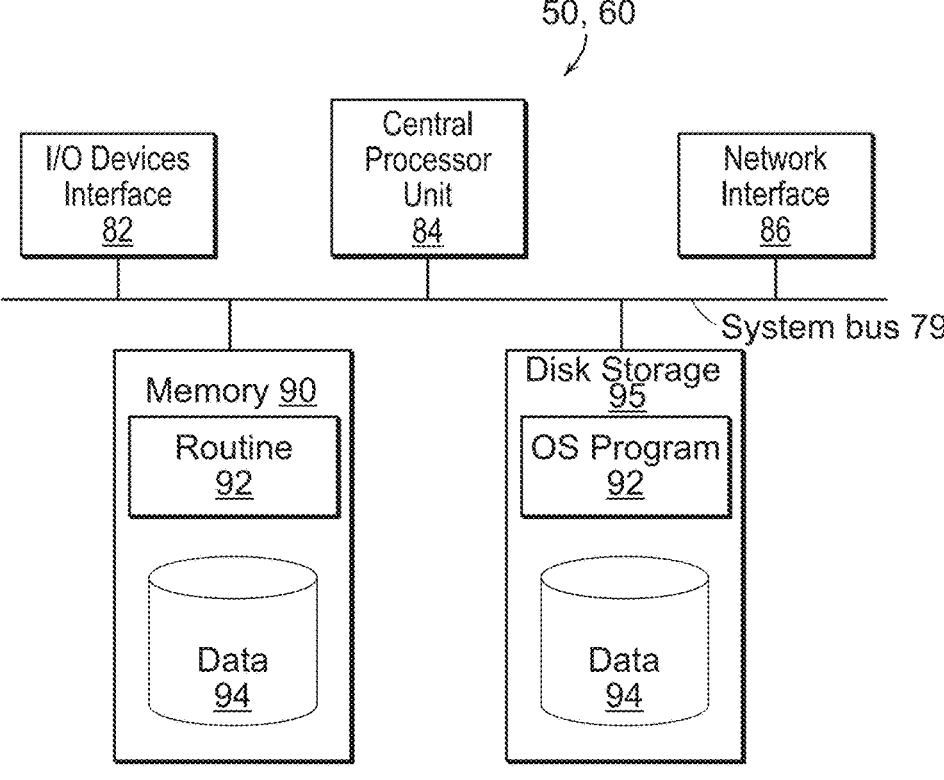
FIG. 17 is a block diagram of computer nodes or devices in the computer network of FIG. 16.

FIG. 17 is a diagram of the internal structure of a computer (e.g., client processor/device 50 or server computers 60) in the computer network of FIG. 3. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 16). Memory 90 provides volatile storage for computer software instructions 92 and data 94 used to implement embodiments of the present invention. Disk storage 95 provides nonvolatile storage for computer software instructions 92 and data 94 used to implement an embodiment of the present invention. Central processor unit 84 is also attached to system bus 79 and provides for the execution of computer instructions.

In particular, embodiments of the present invention execute processor routines for the method 100 of FIG. 15. In one embodiment, the processor routines 92 and data 94 are a computer program product (generally referenced 92), including a non-transitory computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternative embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, other mediums and the like.

In other embodiments, the computer program product 92 provides Software as a Service (SaaS) or similar operating platform.

Alternative embodiments can include or employ clusters of computers, parallel processors, or other forms of parallel processing, effectively leading to improved performance, for example, of generating a computational model. Given the foregoing description, one of ordinary skill in the art understands that different portions of processor routine 100 and different iterations operating on respective sequence reads may be executed in parallel on such computer clusters or parallel processors.

EXEMPLIFICATION

Example 1. Network-Based Drug Repurposing

Repurposing strategies often prioritize drugs approved for (other) diseases whose molecular manifestations are similar to those caused by the pathogen or disease of interest. To search for diseases whose molecular mechanisms overlap with the COVID-19 disease, we first mapped the experimentally identified 332 host protein targets of the SARS-CoV-2 proteins to the human interactome, a collection of 332,749 pairwise binding interactions between 18,508 human proteins (see Example 7, herein). Additional examples of protein-protein interaction networks and human interactomes can be found in the following references: K. Luck, G. M. Sheynkman, I. Zhang, M. Vidal, Proteome-scale human interactomics. *Trends Biochem. Sci.* 42, 342-354 (2017); M. Caldera, P. Buphamalai, F. Müller, J. Menche, Interactome-based approaches to human disease. *Curr. Opin. Syst. Biol.* 3, 88-94 (2017); E. K. Silverman et al., Molecular networks in network medicine: Development and applications. *Wiley Interdiscip. Rev. Syst. Biol. Med* 12, e1489 (2020); and M. Buchanan, G. Caldarelli, P. De Los Rios, F. Rao, M. Vendruscolo, Eds., *Networks in Cell Biology,* (Cambridge University Press, 2010).

Figure 5:
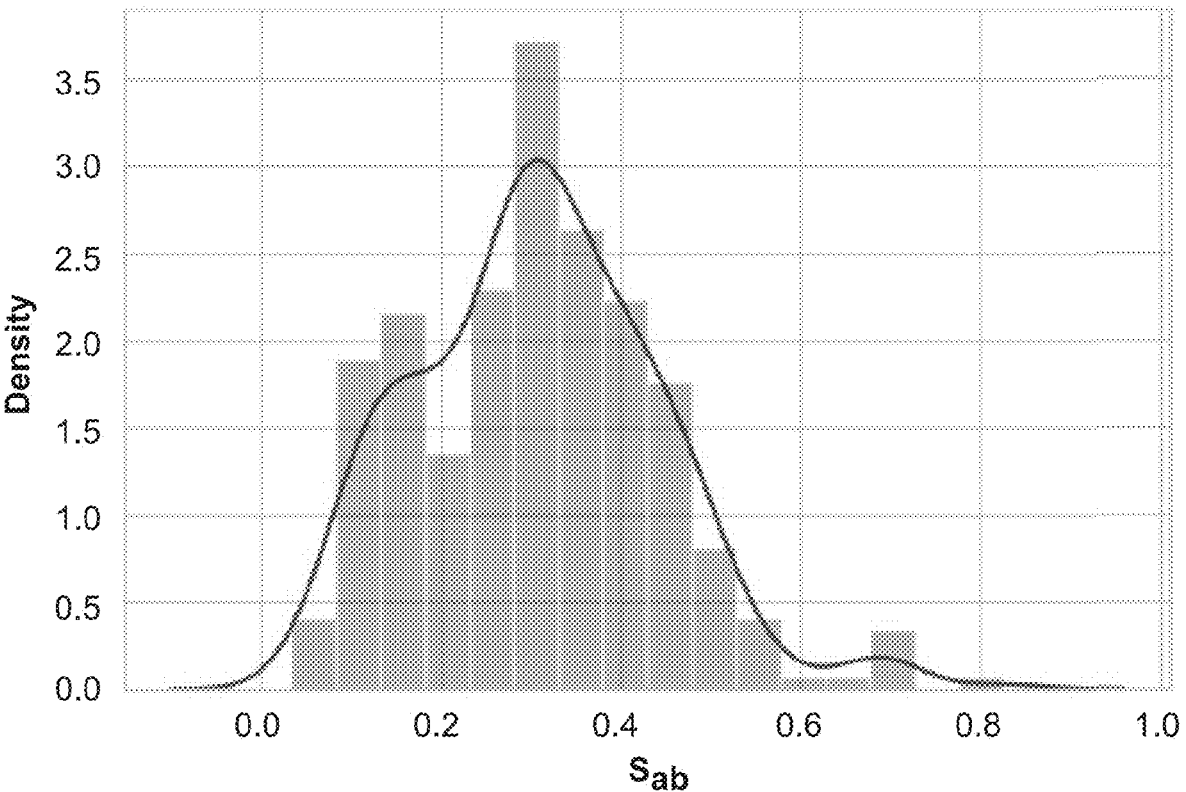
FIG. 5 is a graph of a distribution of the network overlap measure $S_{vb}$ between 299 diseases and COVID-19 targets. The $S_{vb}$ values represent the network-based overlap between SARS-COV2 targets v and the genes associated with each disease b.
Figure 6:
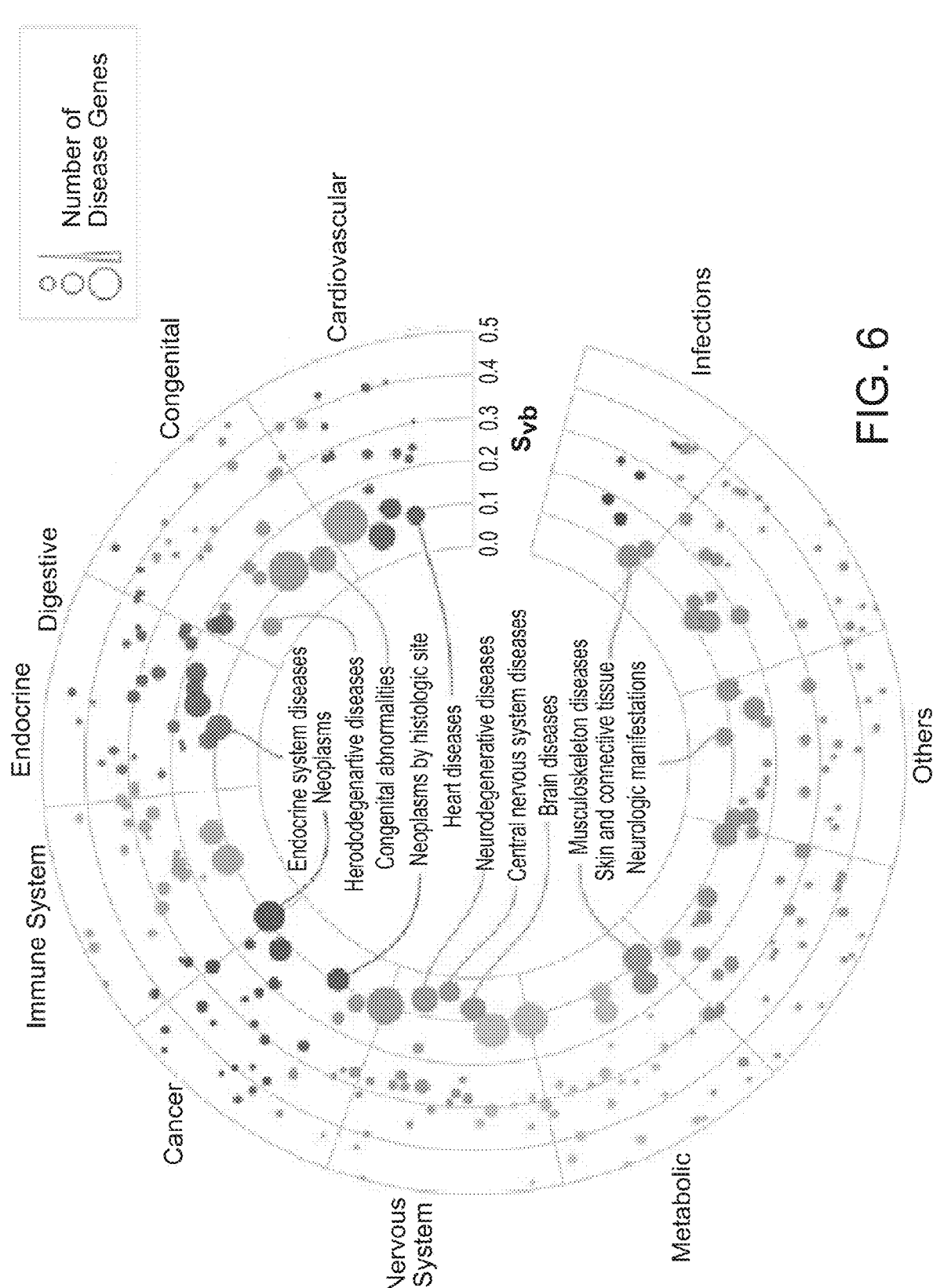
FIG. 6 is a chart of disease comorbidity measured by the network overlap between COVID-19 targets and 299 diseases. The figure represents each disease as a circle whose radius reflects the number of disease genes associated with it. The diseases closest to the center, whose names are marked, are expected to have higher comorbidity with the COVID-19 outcome. The farther a disease is from the center, the more distant are its disease proteins from the COVID-19 viral targets.

We found that 208 of the 332 viral targets form a large connected component (hereinafter, COVID-19 disease module, see FIG. 2B), indicating that the SARS-CoV-2 targets aggregate in the same network vicinity. Next, we evaluated the network-based overlap between proteins associated with 299 diseases (d) and the host protein targets of SARS-CoV-2 (v) using the $S_{vd}$ metric, finding $S_{vd}>0$ for all diseases, implying that the COVID-19 disease module does not directly overlap with the disease proteins associated with any single disease (FIGS. 5, 6). In other words, a potential COVID-19 treatment cannot be derived from the arsenal of therapies approved for a specific disease, arguing for a network-based strategy that can identify repurposable drugs without regard for their established disease indication. Additional description and examples of evaluation of networks in an interactome can be found in J. Menche et al., Disease networks. Uncovering disease-disease relationships through the incomplete interactome. *Science* 347, 1257601 (2015)).

Figure 1A:
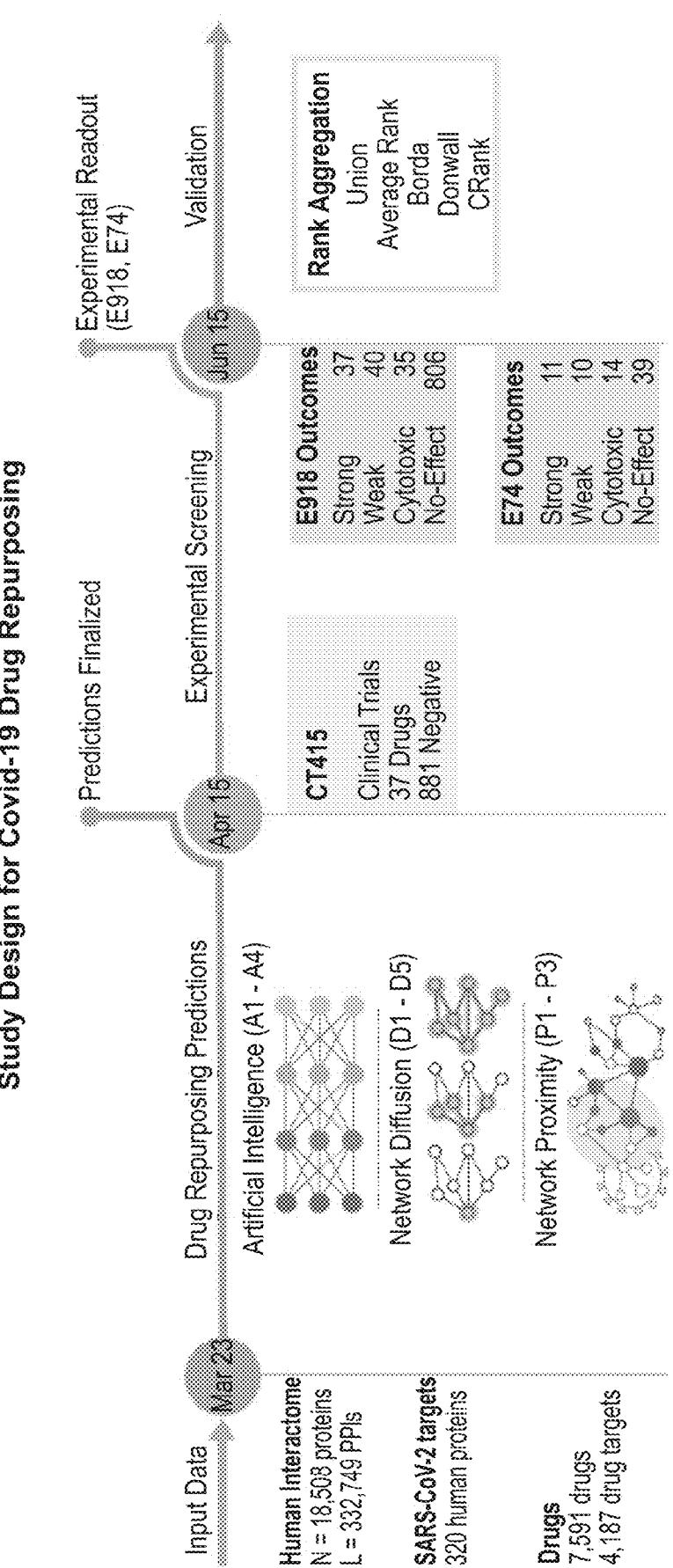
FIGS. 1A-1C illustrate a network medicine framework for drug repurposing.
Figure 1B:
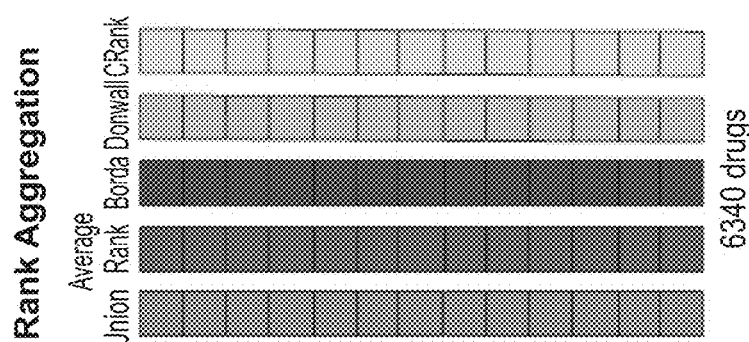
Figure 1B:
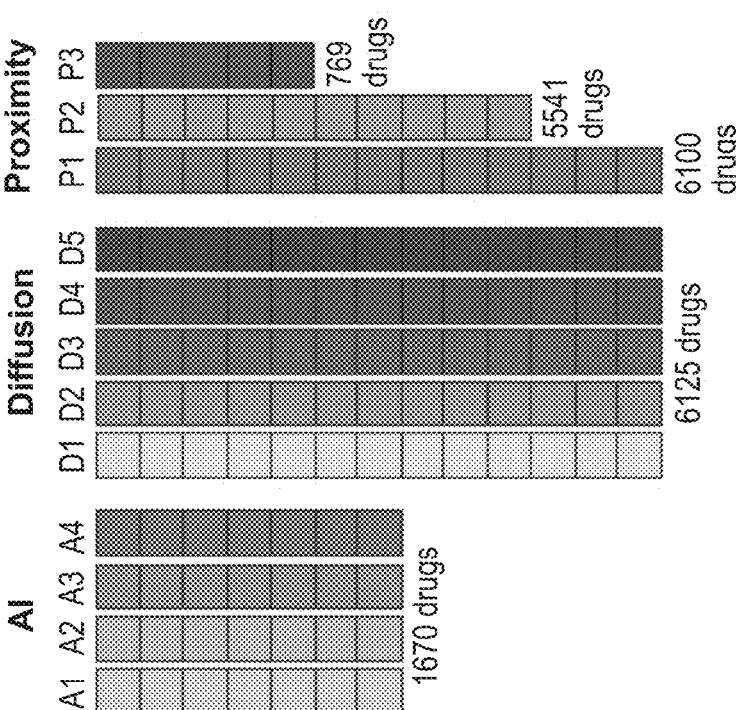

We implemented three competing network repurposing methodologies (FIG. 1A-1B and further described in Examples 10-13, herein).

1) An artificial intelligence-based algorithm maps drug protein targets and disease-associated proteins to points in a low-dimensional vector space, resulting in four predictive pipelines A1-A4, that rely on different drug-disease embeddings. The AI module is further described in Example 11, herein. Additional description and examples of AI methods can be found in M. Zitnik et al., Machine learning for integrating data in biology and medicine: Principles, practice, and opportunities. *Inf Fusion* 50, 71-91 (2019); and M. Zitnik, R. Sosic, J. Leskovec, Prioritizing network communities. *Nat. Commun.* 9, 2544 (2018).

2) A diffusion algorithm is inspired by diffusion state distance, and ranks drugs based on capturing network similarity of a drug's protein targets to the SARS-CoV-2 host protein targets. Powered by distinct statistical measures, the algorithm offers five ranking pipelines (D1-D5). The diffusion module is further described in Example 12, herein. Additional description and examples of diffusion methods can be found in M. Cao et al., Going the distance for protein function prediction: A new distance metric for protein interaction networks. *PLoS One* 8, e76339 (2013).

Figures 2A, 2B, 2C:
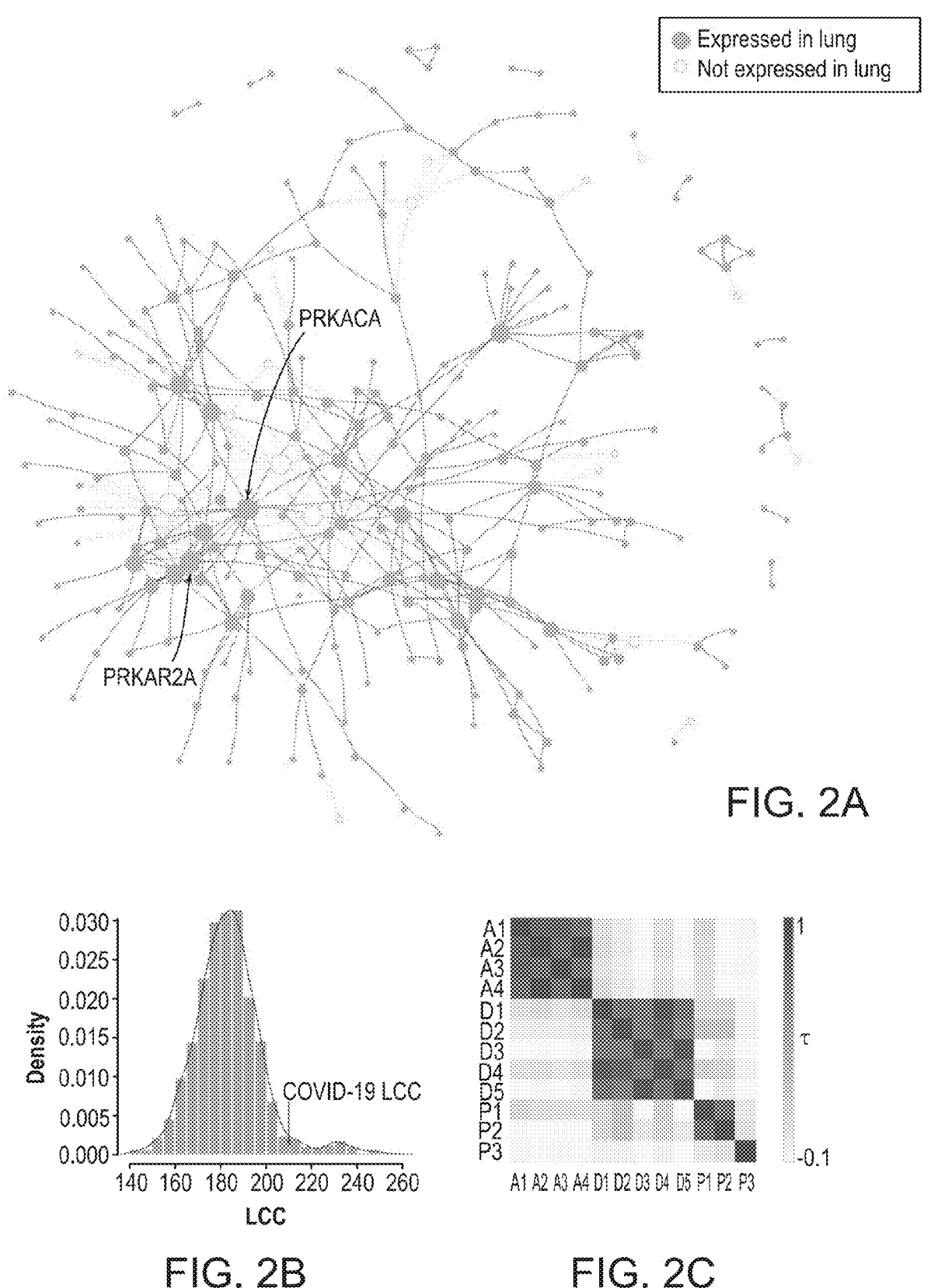
FIGS. 2A-2C illustrate a COVID-19 disease module.

3) A proximity algorithm ranks drugs based on the distance between the host protein targets of SARS-CoV2 and the closest protein targets of drugs, resulting in three predictive pipelines of which: P1 relies on all drug targets; P2 tests the hypothesis that removing the protein targets involved in drug delivery and drug metabolism, shared by multiple drugs, can improve the specificity of the proximity measure; and P3 tests if drug-induced differentially expressed genes can offer additional predictive power. The low correlations across the three algorithms indicate that the methods extract complementary information from the network (FIG. 2C, and Example 15, herein). The proximity module is further described in Example 13, herein. Additional description and examples of proximity measures can be found in E. Guney, J. Menche, M. Vidal, A.-L. L. Baribasi, Network-based in silico drug efficacy screening. *Nature Communications* 7, 10331 (2016).

Example 2. Experimental and Clinical Validation of Drug-Repurposing Pipelines

We implemented the 12 pipelines to predict the expected efficacy of 6,340 drugs in Drugbank (D. S. Wishart et al., DrugBank 5.0: A major update to the DrugBank database for 2018. *Nucleic Acids Res.* 46, D1074-D1082 (2018)) against SARS-CoV-2 and extracted and froze the predictions in the form of 12 ranked lists on Apr. 15, 2020. All pipelines rely on the same input data and to maintain the prospective nature of the study, all subsequent analyses rely on this initial prediction list. As the different pipelines make successful predictions of a different subset of drugs, we identified 918 drugs for which all pipelines (except for P3, which predicts the smallest number of drugs) offer predictions and whose compounds were available in the Broad Institute drug repurposing library (see S. M. Corsello et al., The drug repurposing hub: A next-generation drug library and information resource. *Nat. Med.* 23, 405-408 (2017)) (FIG. 1); we used two independent datasets to quantify the predictive power of each pipeline over the same set of drugs.

Figure 3A:
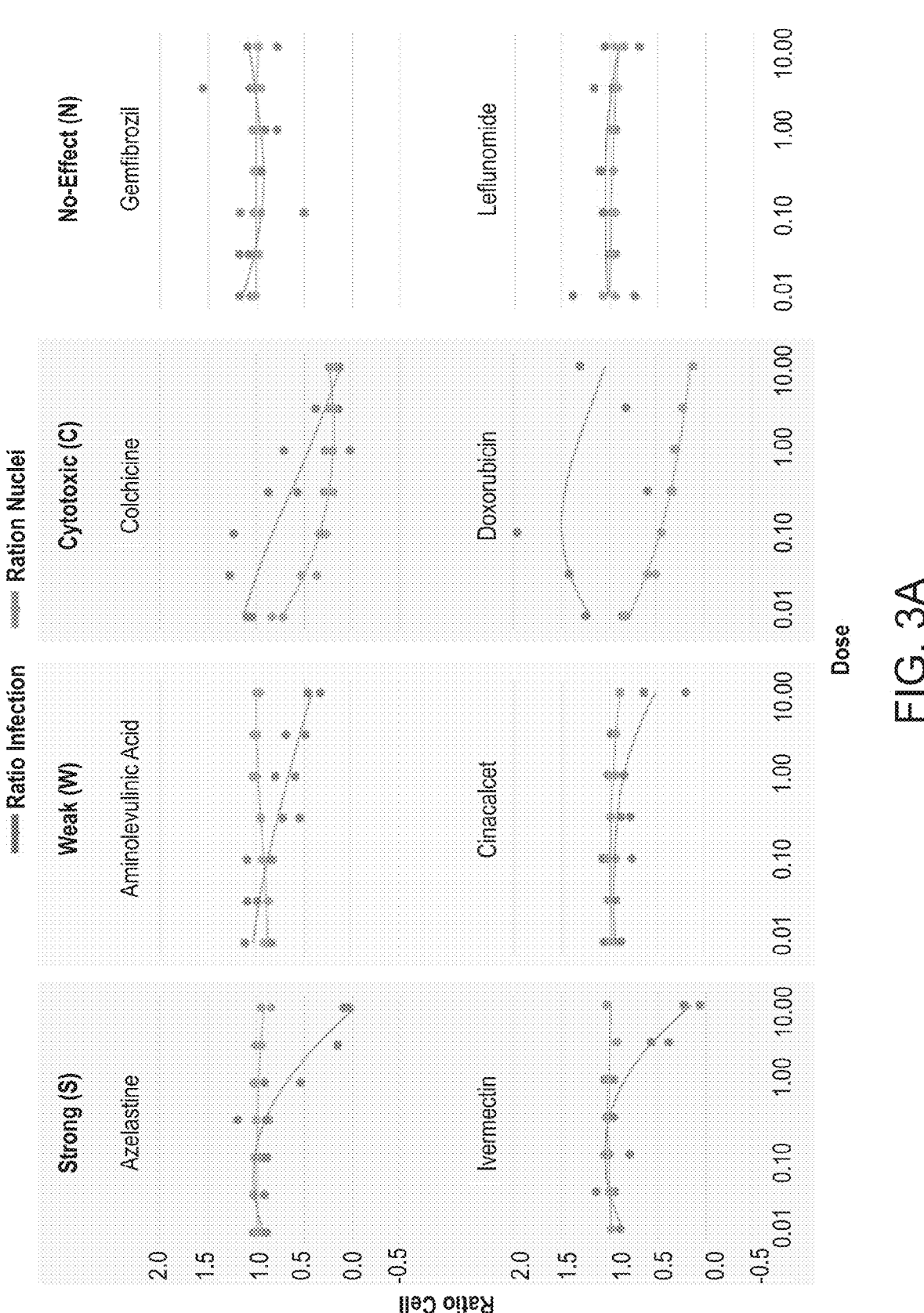
FIGS. 3A-3C illustrate experimental outcomes and network origins.
Figures 3B, 3C:
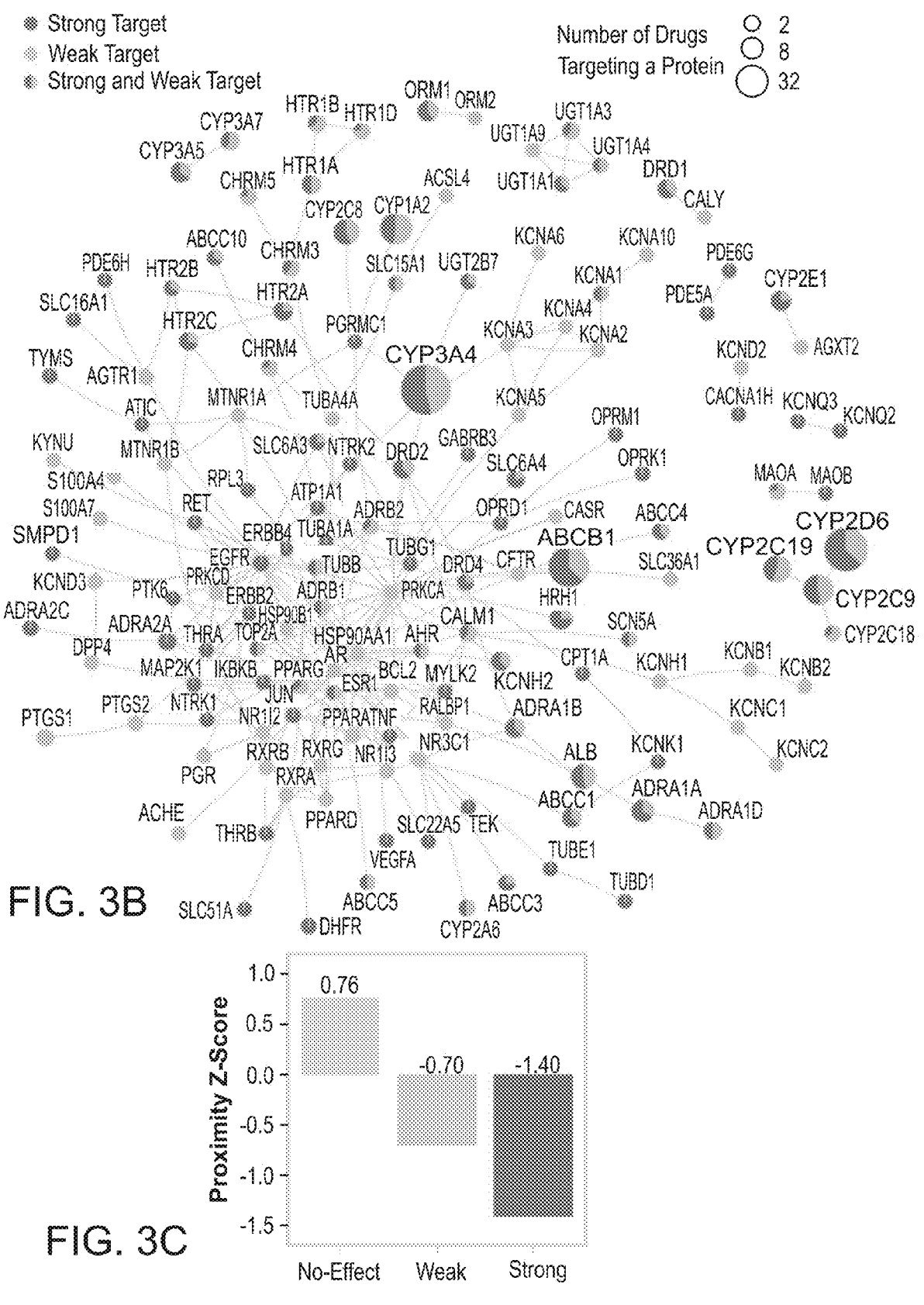

As the first ground truth, we compare our predictions against the 918 compounds that had been experimentally screened for their efficacy against SARS-CoV-2 in VeroE6 cells, kidney epithelial cells derived from African green monkey (see Examples, 16-20, herein), experiments performed after the predictions were finalized (FIG. 1A). Briefly, the VeroE6 cells were pre-incubated with the drugs (from 8 μM down to 8 nM) and then challenged with wild type SARS-CoV-2 strain USA-WA1/2020. Of the 918 drugs, 806 had no detectable effect on viral infectivity (N drugs, 87.8% of the tested list); 35 were cytotoxic to the host cells (C drugs); 37 had a strong effect (S drugs), being active over a broad range of concentrations; and 40 had a weak effect (W drugs) on the virus (FIG. 3A). As the prediction pipelines offer no guidance on the magnitude of the in vivo effect, we considered as positive outcomes drugs that had a strong or a weak effect on the virus (S&W, 77 drugs, FIG. 18), and as negative outcomes the drugs without detectable effect (N, 806 drugs).

Second, on Apr. 15, 2020 (prediction date), we scanned clinicaltrials.gov, identifying 67 drugs in 134 clinical trials for COVID-19 (CT415 dataset). To compare outcomes across datasets, we limit our analysis to the experimentally tested 918 drugs, considering as positive the 37 drugs in clinical trial on the E918 list, and negative the remaining 881 drugs. As the outcomes of these trials are largely unknown, validation against CT415 dataset tests each pipeline's ability to predict the pharmacological consensus of the medical community on drugs with expected potential efficacy for COVID-19 patients.

For the E918 experimental outcomes (FIG. 4A), the best area under the curve (AUC) of 0.63 is provided by P1, followed by D2 (AUC=0.58) and P3 (AUC=0.58). For CT415 (FIG. 4B), we observe particularly strong predictive power for the four AI-based pipelines (AUC of 0.73-0.76), followed by proximity P1 (AUC=0.57) and P2 (AUC=0.56).

Figures 4A, 4B, 4C, 4D, 4E, 4F:
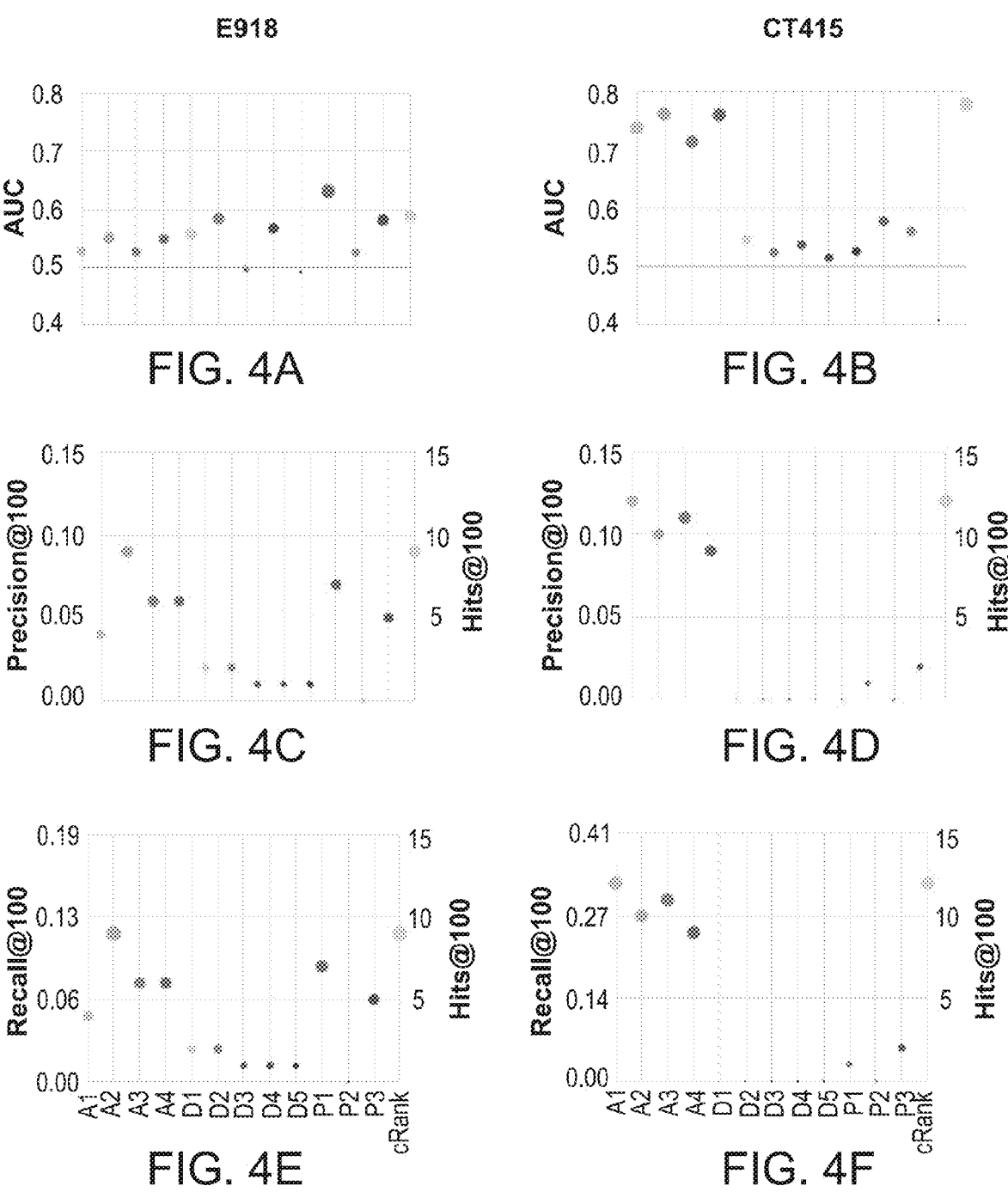
FIGS. 4A-4H are graphs of the results of performance of the predictive pipelines.

The goal of drug repurposing is to prioritize all available drugs, allowing us to limit experimental efforts only to the top-ranked compounds: hence, improve efficiency and resource utilization. Therefore, measuring the number of positive outcomes at the top of the list offers a better measure to evaluate the predictive power than the AUC. Thus, the most appropriate performance metric is the number of positive outcomes among the top K-ranked drugs (precision at K), and the fraction of all positive outcomes among the top K-ranked drugs (recall at K). For the E918 dataset (FIG. 4C), A2 ranks 9 S&W drugs among the top 100, followed by P1 (7 drugs), and A3 and A4 (6 drugs). We observe similar trends for recall (FIG. 4E): the A2 pipeline ranks 11.7% of all positive drugs in the top 100, while P1 selects 9%. Finally, A1 ranks 12 drugs currently in clinical trials among the top 100 in CT415, followed by A3 (11 drugs) and A2 (10 drugs), trends that are similar for recall (FIG. 4F).

Taken together, our first key results have the finding that while most algorithms show statistically significant predictive power (see Example 21), they have different performance on the different ground truth datasets: the A1 pipeline offers strong predictive power for the drugs selected for clinical trials, while proximity offers better predictive power for the E918 experimental outcomes. While together the twelve pipelines identify 22 positive drugs among the top 100, none of the pipelines offer consistent superior performance for all outcomes, prompting us to develop a multi-modal approach that can extract the joint predictive power of all pipelines.

Example 3. Multimodal Approach for Drug Repurposing

Predictive models for drug repurposing are driven by finite experimental resources that limit downstream experiments to those involving a finite number (K) of drugs. How do we identify these K drugs to maximize the positive outcomes of the tested list? With no initial knowledge as to which of the $N_p$=12 predictive pipelines offer the best predictive power, we could place equal trust in all, by selecting the top $K/N_p$ drugs from each pipeline (Union list). We compared this scenario with an alternative strategy that combines the predictions of the different pipelines.

A widely used approach is to calculate the average rank of each drug over the $N_p$ pipelines (Average Rank list). The alternative is to search for consensus ranking that maximizes the number of pairwise agreements between all pipelines. As the optimal outcome, called the Kemeny consensus, is NP-hard to compute, we implemented three heuristic rank aggregation algorithms (RAAs) that approximate the Kemeny consensus: Borda's count, the Dowdall method, and CRank. For example, if the resources allow us to test K=120 drugs, we ask which ranked list offers the best precision and recall at 120 the Union list collecting the top 10 predictions from the 12 pipelines; or the top 120 predictions of Average Rank, Borda, Dowdall, or CRank; or the top 120 drugs ranked by an individual pipeline.

Figure 4G:
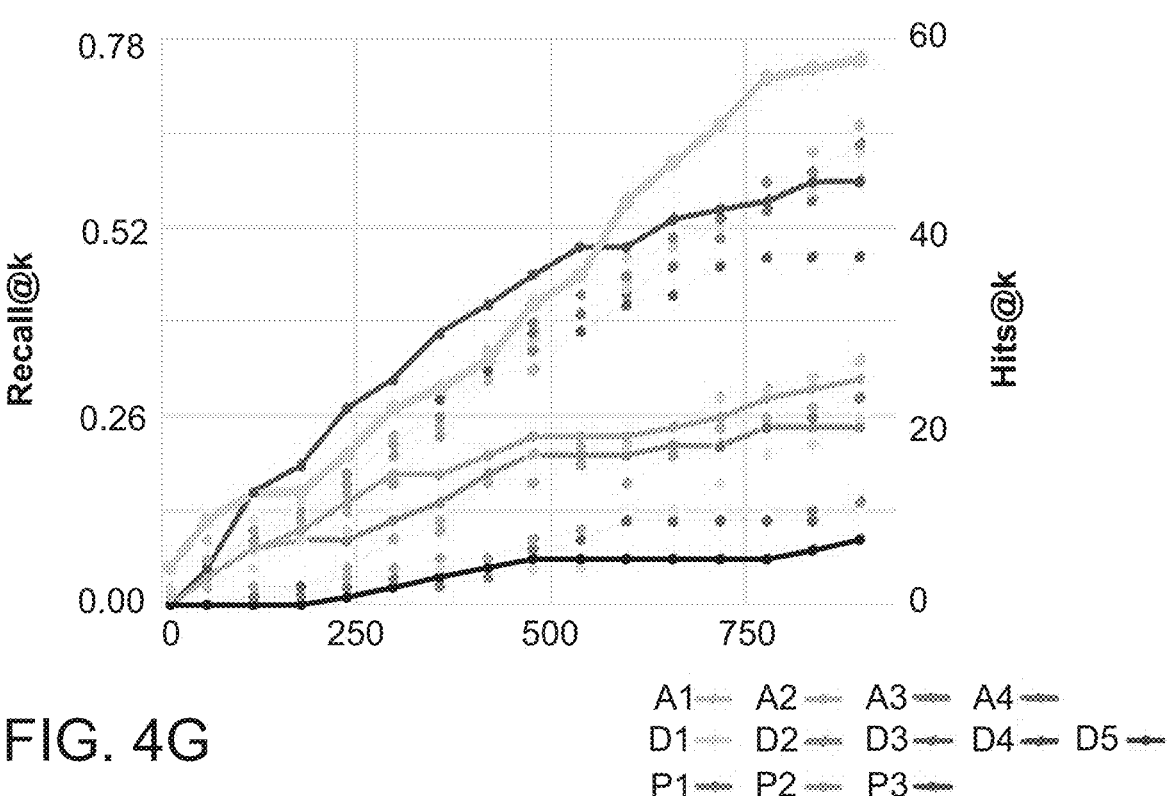
Figure 4H:
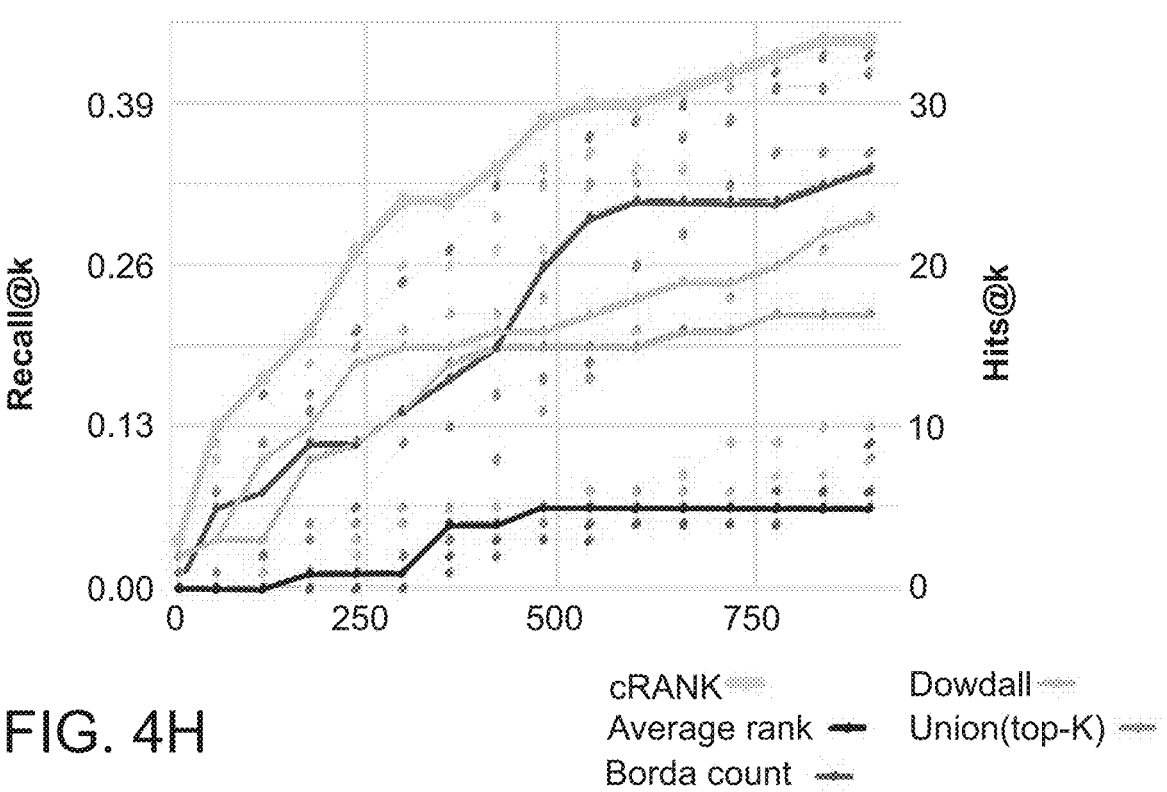

We found that Average Rank offers the worst performance, trailing the predictive power of most individual pipelines (FIGS. 4G, 4H). The Union List and Dowdall offer better outcomes, but trail behind the best performing individual pipelines (E918, CT415). Borda has a strong predictive performance for E918, but not for CT415. In contrast, CRank, which relies on Bayesian factors, offers a consistently high predictive performance for all datasets and most K values. CRank performs equally well for two other datasets: a manually curated prospective list E74 (described below) and the list of clinical trials updated on Jun. 15, 2020 (C615, FIG. 12). In other words, we found that CRank extracts the cumulative predictive power of all methods, matching or exceeding the predictive power of the individual pipelines across all datasets, representing our second key result. Its persistent performance indicates that an unsupervised multimodal approach can significantly improve the hit rate over individual prediction algorithms. It also suggests that in the absence of a ground truth, the Kemeny consensus, which seeks a ranking with the smallest number of pairwise disagreements between the individual pipelines, represents an effective and theoretically principled strategy when each pipeline carries some predictive power.

Example 4. Confirmation in Human Cell Lines

Figure 10:
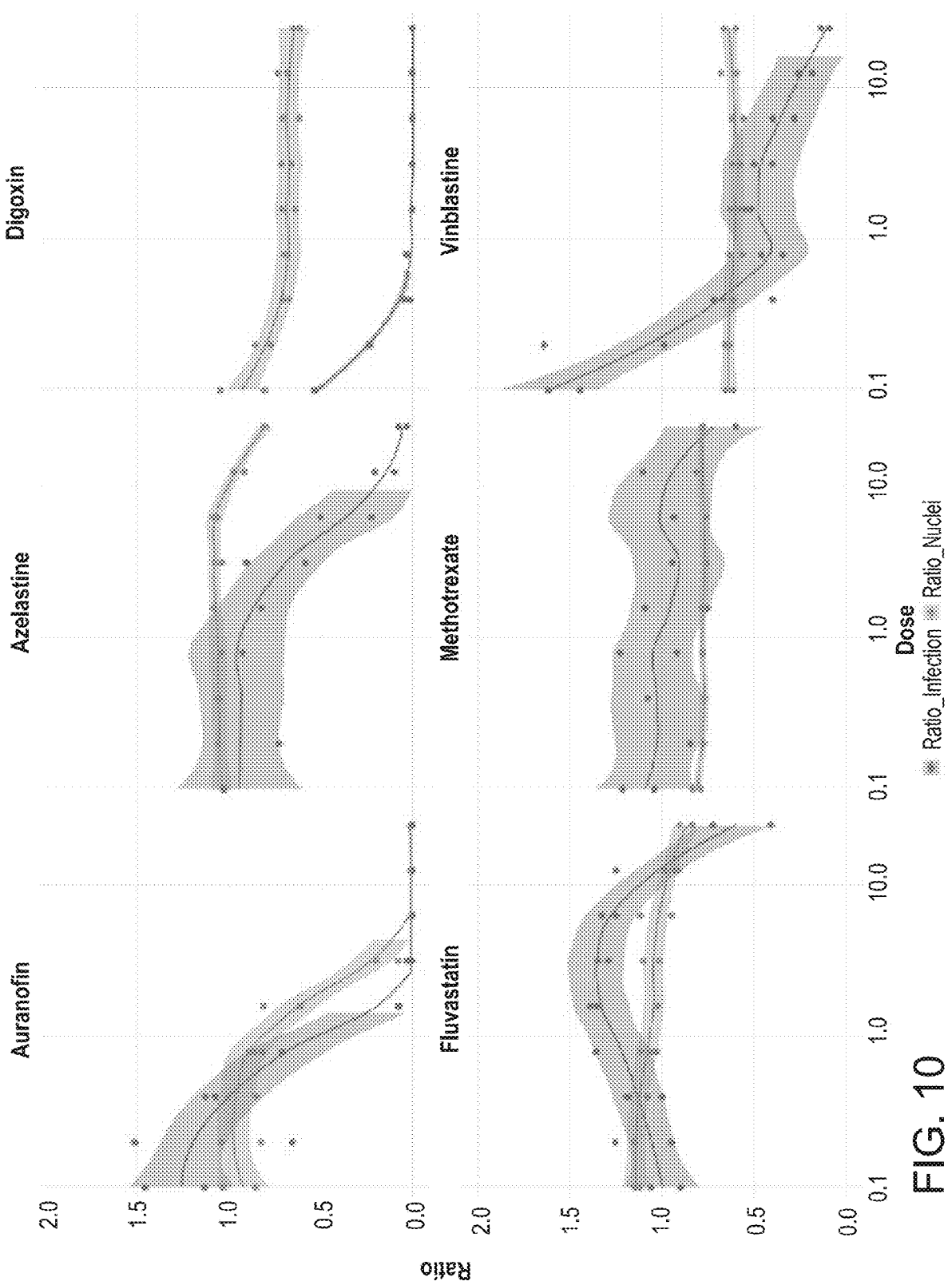
FIG. 10 is a compound graph of drug response curves for S&W drugs validated in the human cell line. From the top 200 drugs, the ones that showed viral load deduction in the first screening using Huh7 cells were re-screened, challenged in vitro with SARS-CoV-2 virus and treated with the drug at a nine-point dilution series from 25 μM to 100 nM. The result shows that Auranofin, Azelastine, Vinblastine, Fluvastatin, Methotrexate and Digoxin are able to reduce the viral load, with particularly strong effect observed for auranofin. Note that, methodextrate is effective only in the last dose, and therefore, still classified as effective, while the other drugs can be effective in multiple dose points. The ratio nuclei is the ratio of nuclei count in the treated cells, normalized by the nuclei count in the controls; the ratio infection is the infected cell ratio normalized by the nuclei count in control.
Figure 11:
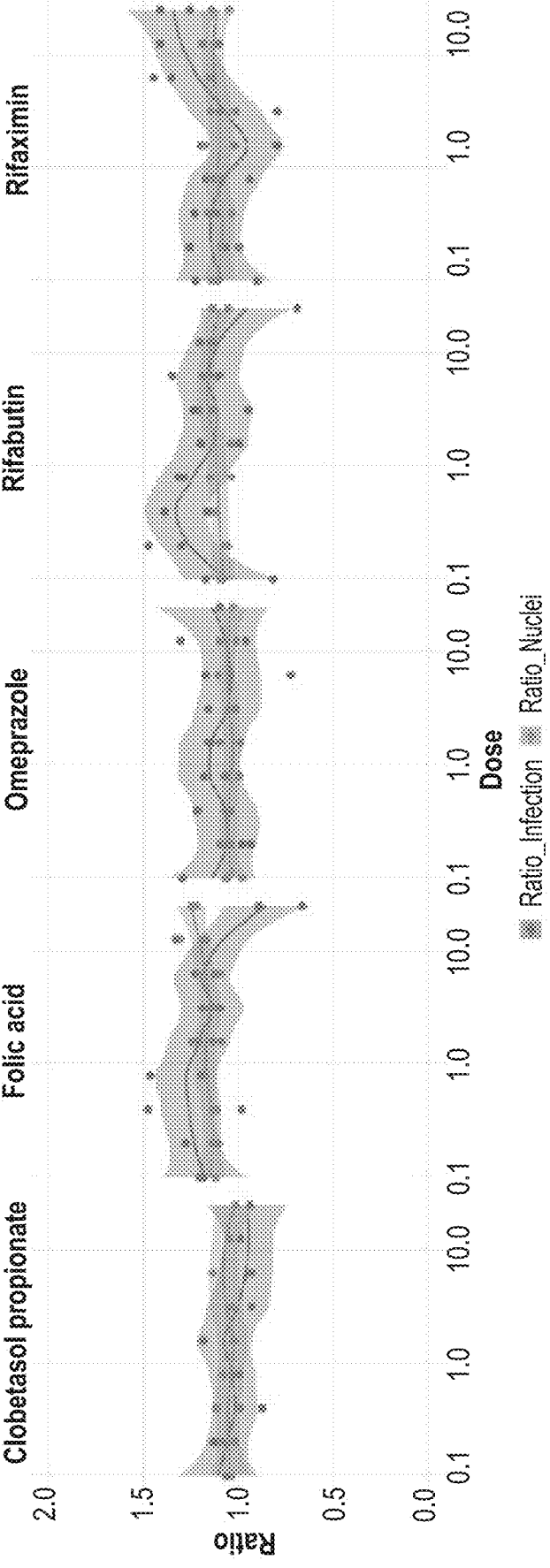
FIG. 11 is a compound graph of drug response curves for N drugs validated in the human cell line. By re-screening the drugs that showed viral load deduction from top 200 ranked ones in the first screening using Huh7 cells, we were able to capture that five (out 11 drugs) did not show significant reduction on the viral load. The ratio nuclei is the ratio of nuclei count in the treated cells, normalized by the nuclei count in the controls; the ratio infection is the infected cell ratio normalized by the nuclei count in control.
Figure 12A:
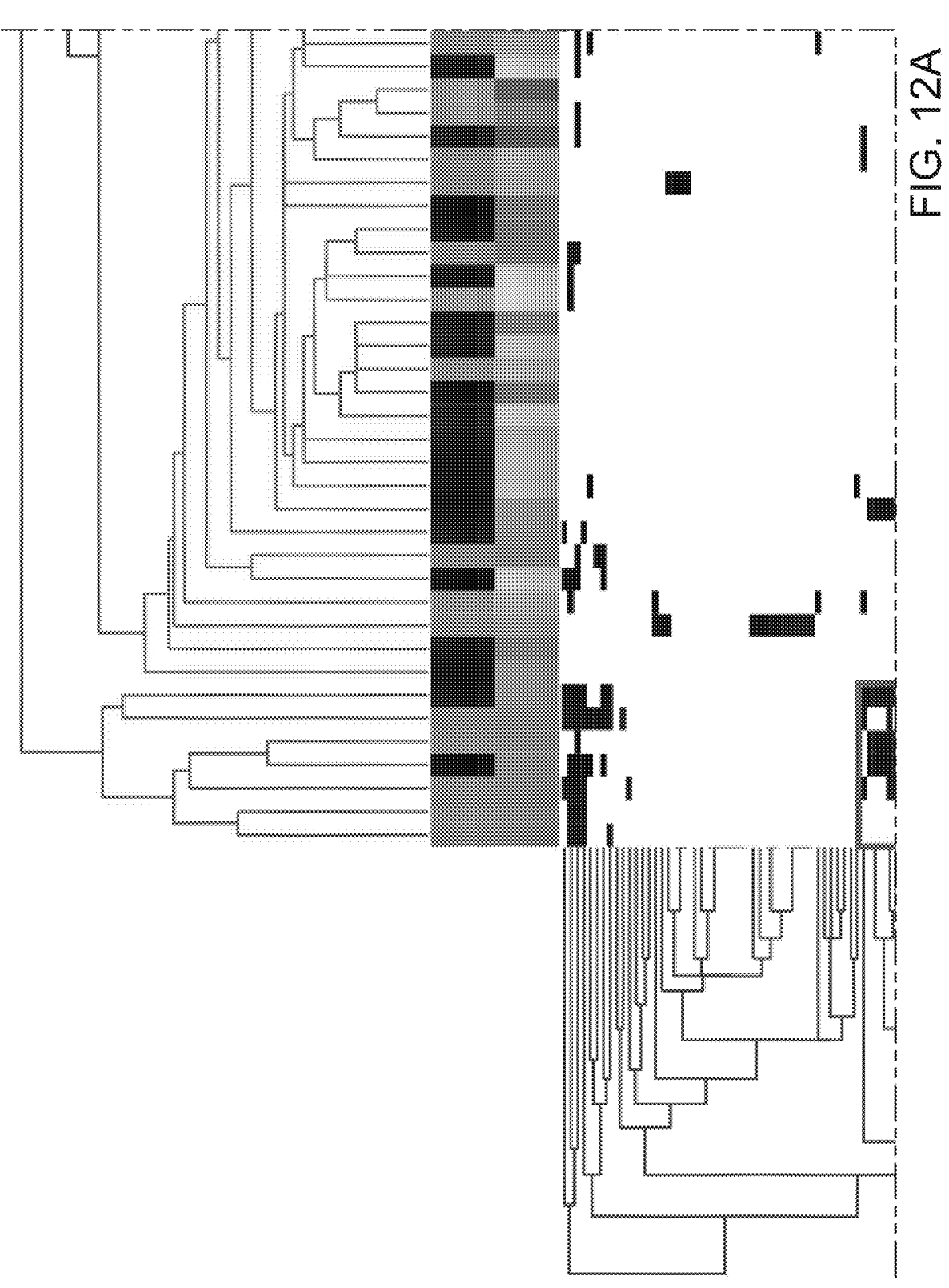
FIG. 12 illustrates a hierarchical clustering. The hierarchical clustering highlights groups of drugs with similar target profiles. The heatmap shows 77 S&W drugs from the E918 dataset and their respective targets (colored cells). Clustering was performed using Euclidean distance and single linkage.
Figure 12B:
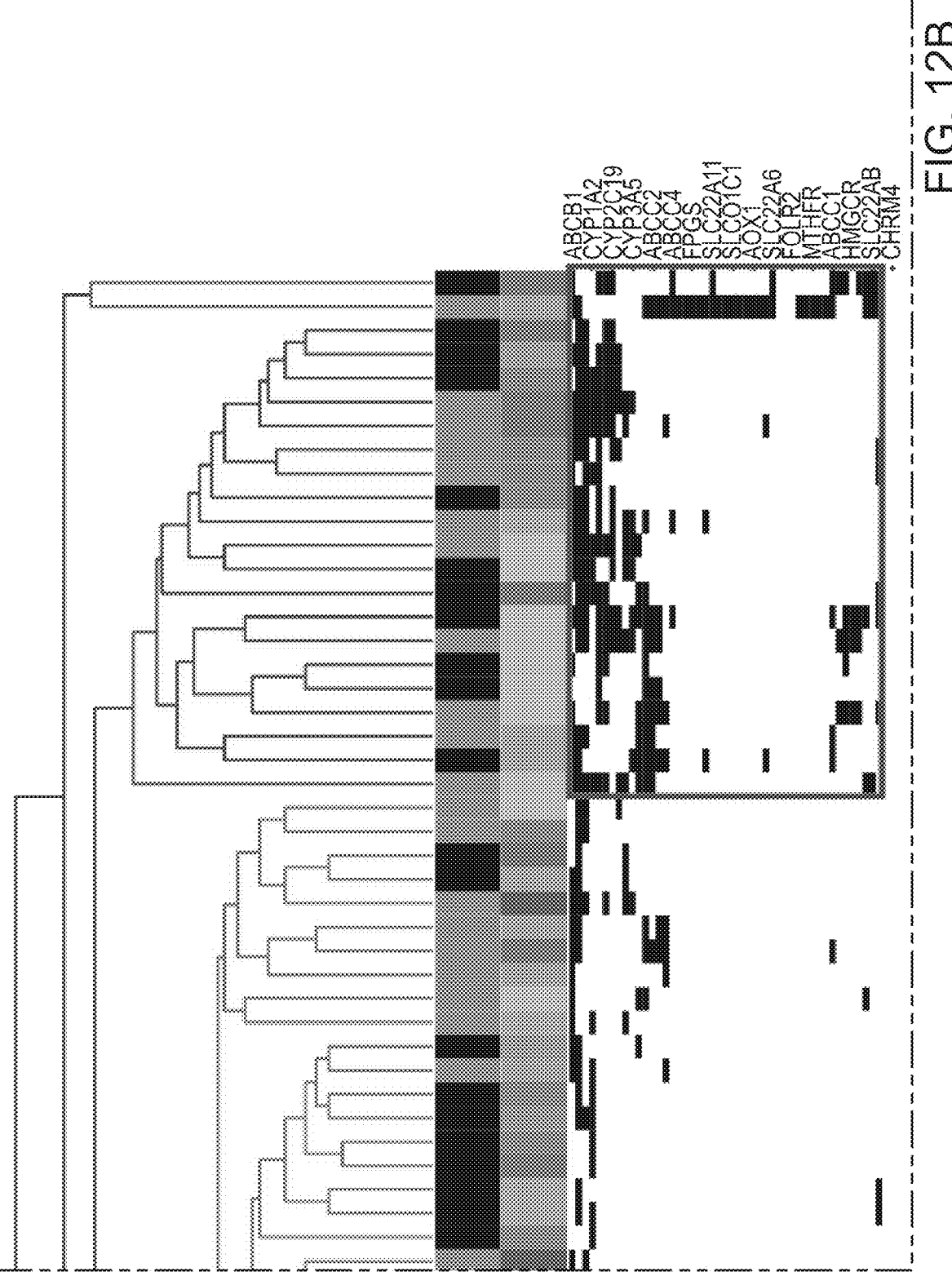
Figure 12C:
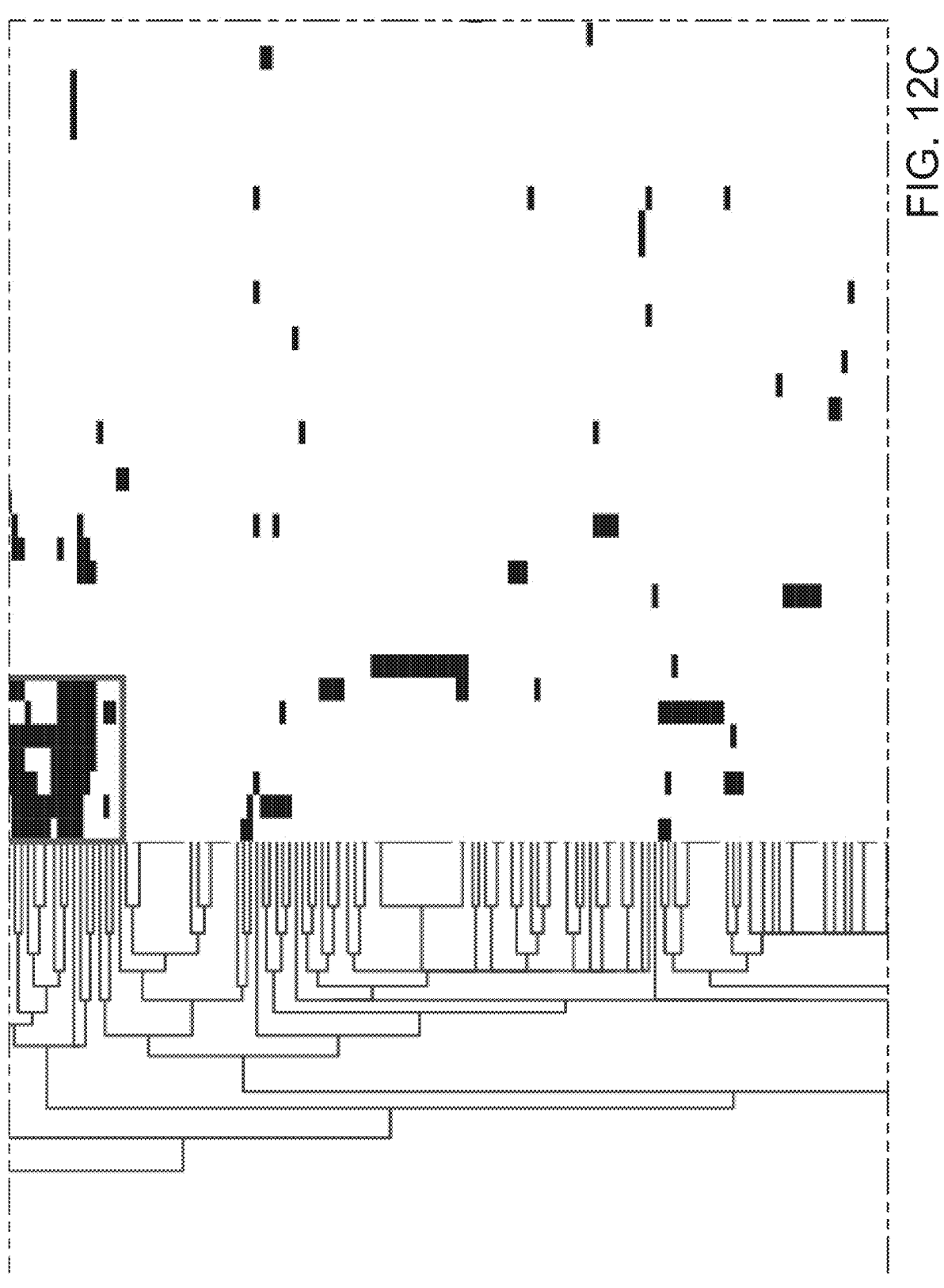
Figure 12D:
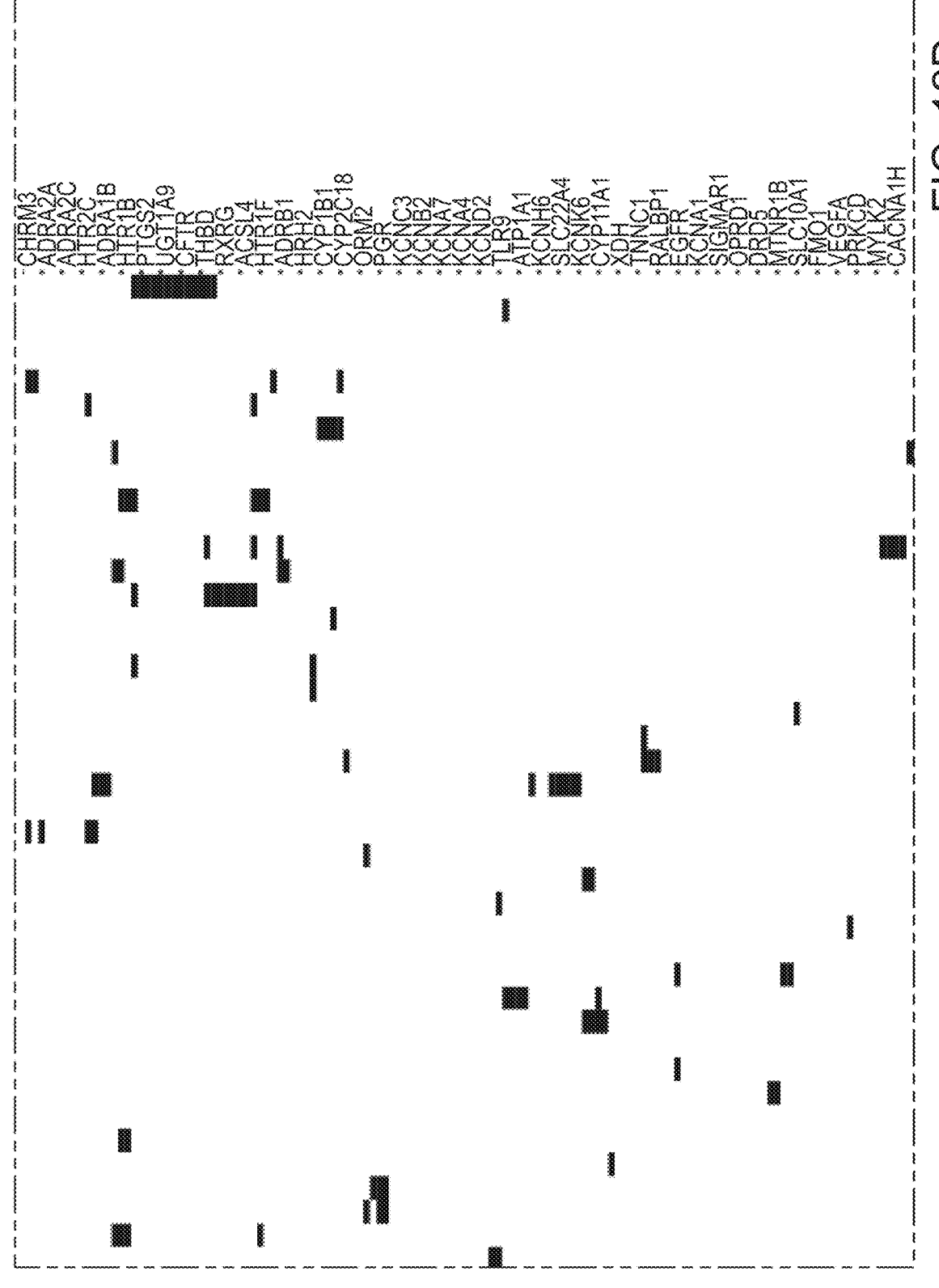
Figure 12E:
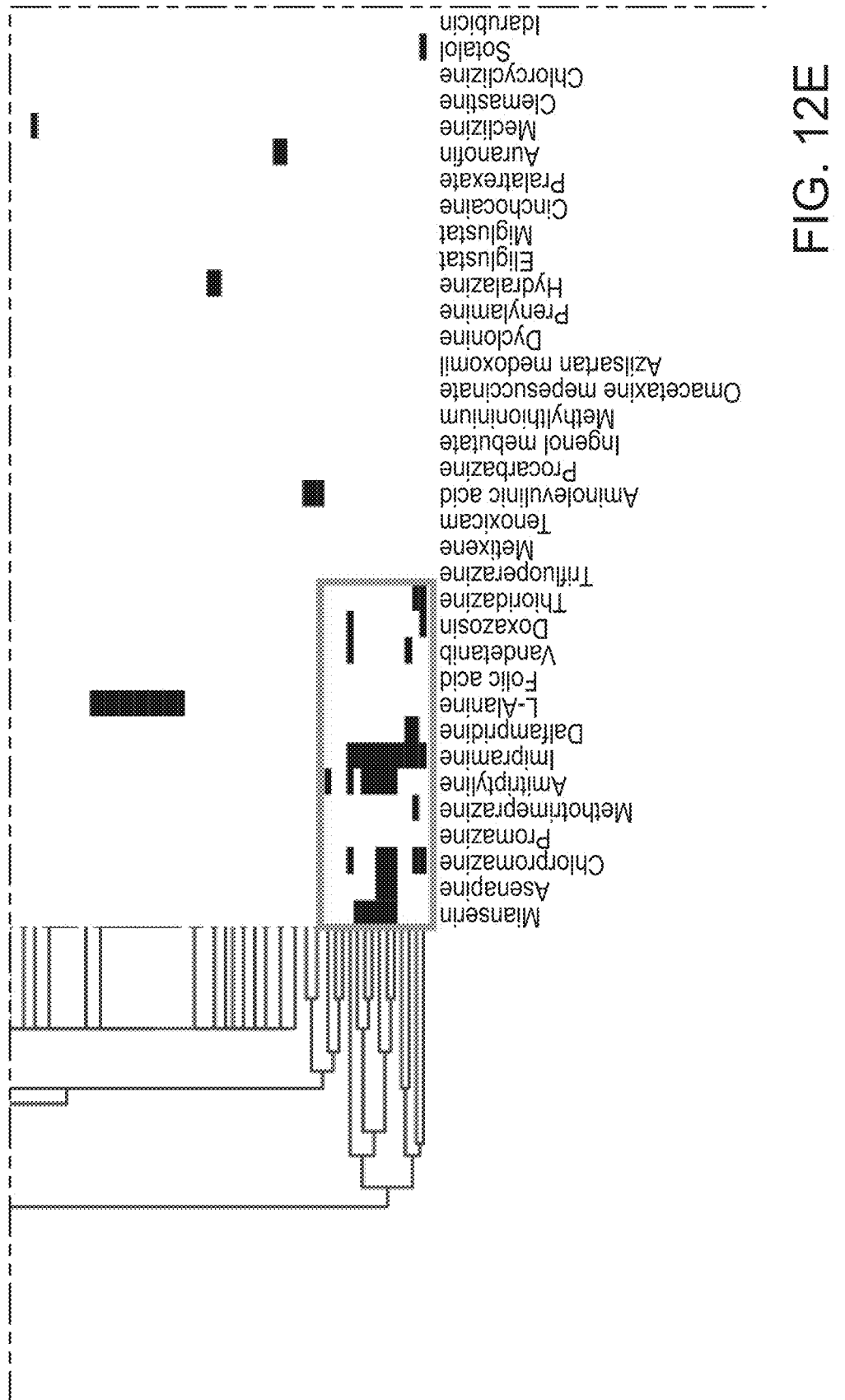
Figure 12F:
Figure 12H:
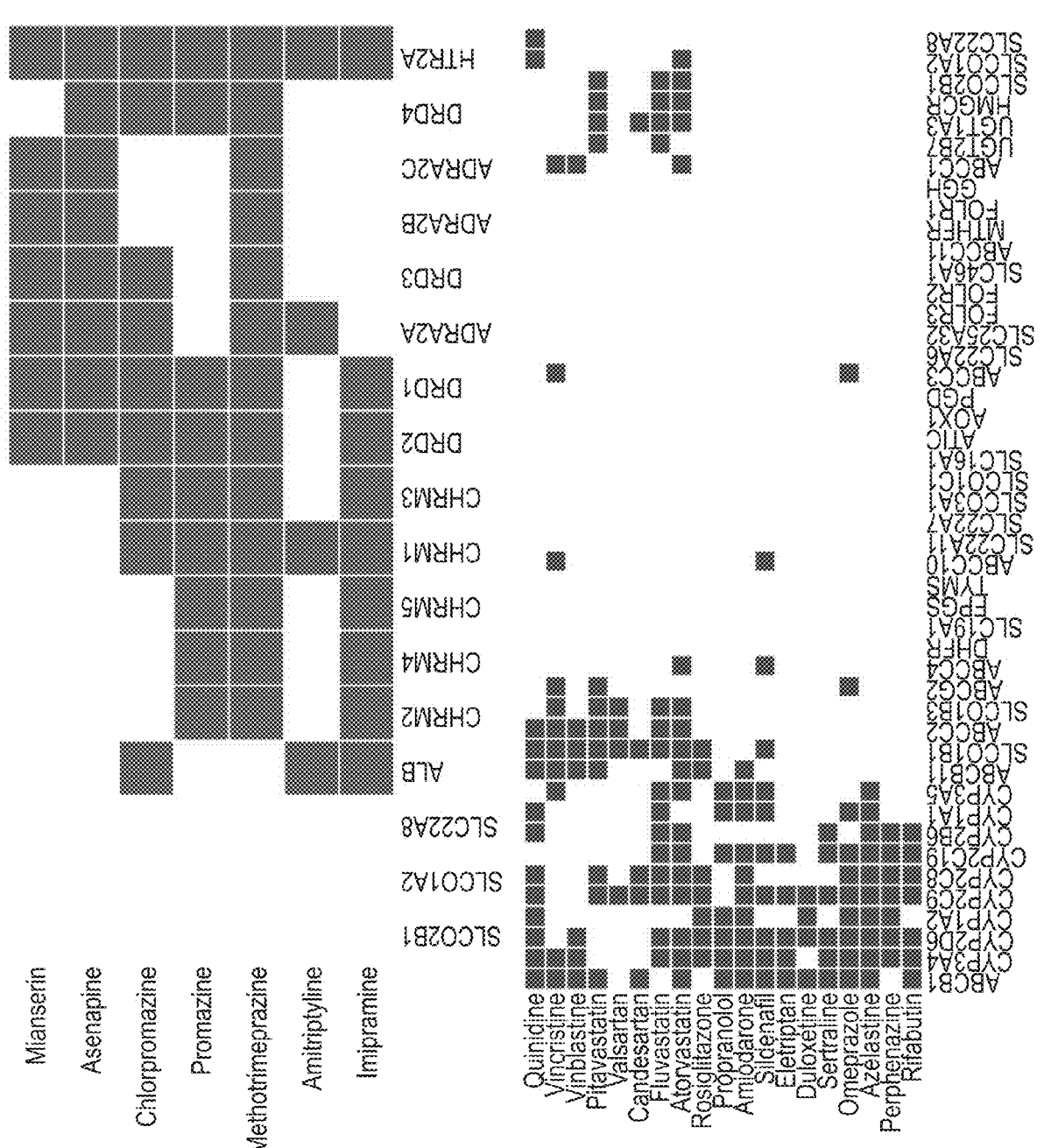
Figure 12I:
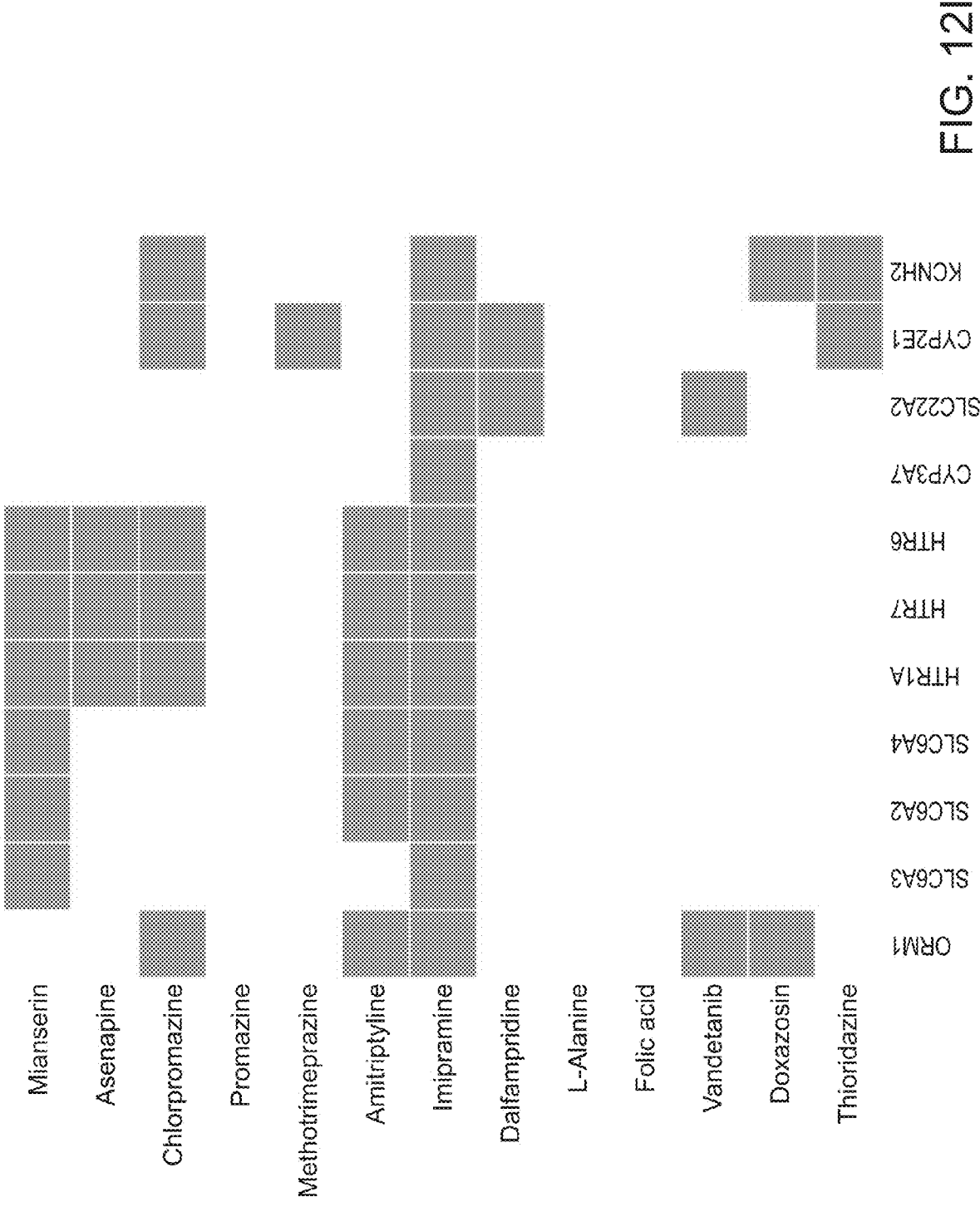
Figure 13A:
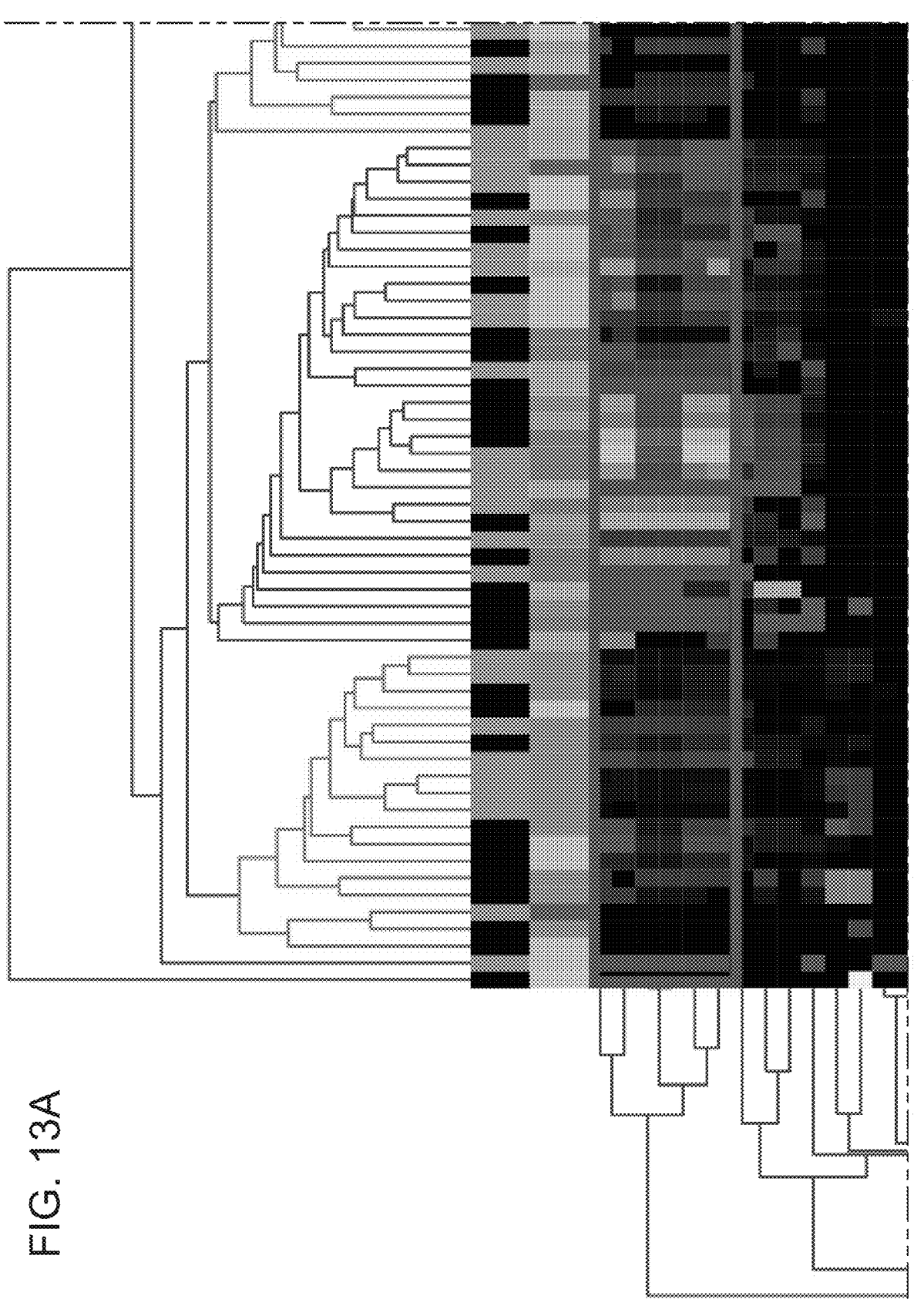
FIG. 13 illustrates pathway enrichment. The heatmap shows successful (S&W) drugs in the E918 dataset and their respective Reactome pathways in which their targets are enriched. Hierarchical clustering (Euclidean, single linkage) highlights different groups of drugs with similar pathway profiles. We highlight the pathways for three drug clusters, emphasizing the proteins targeted in one example pathway for each cluster.
Figure 13B:
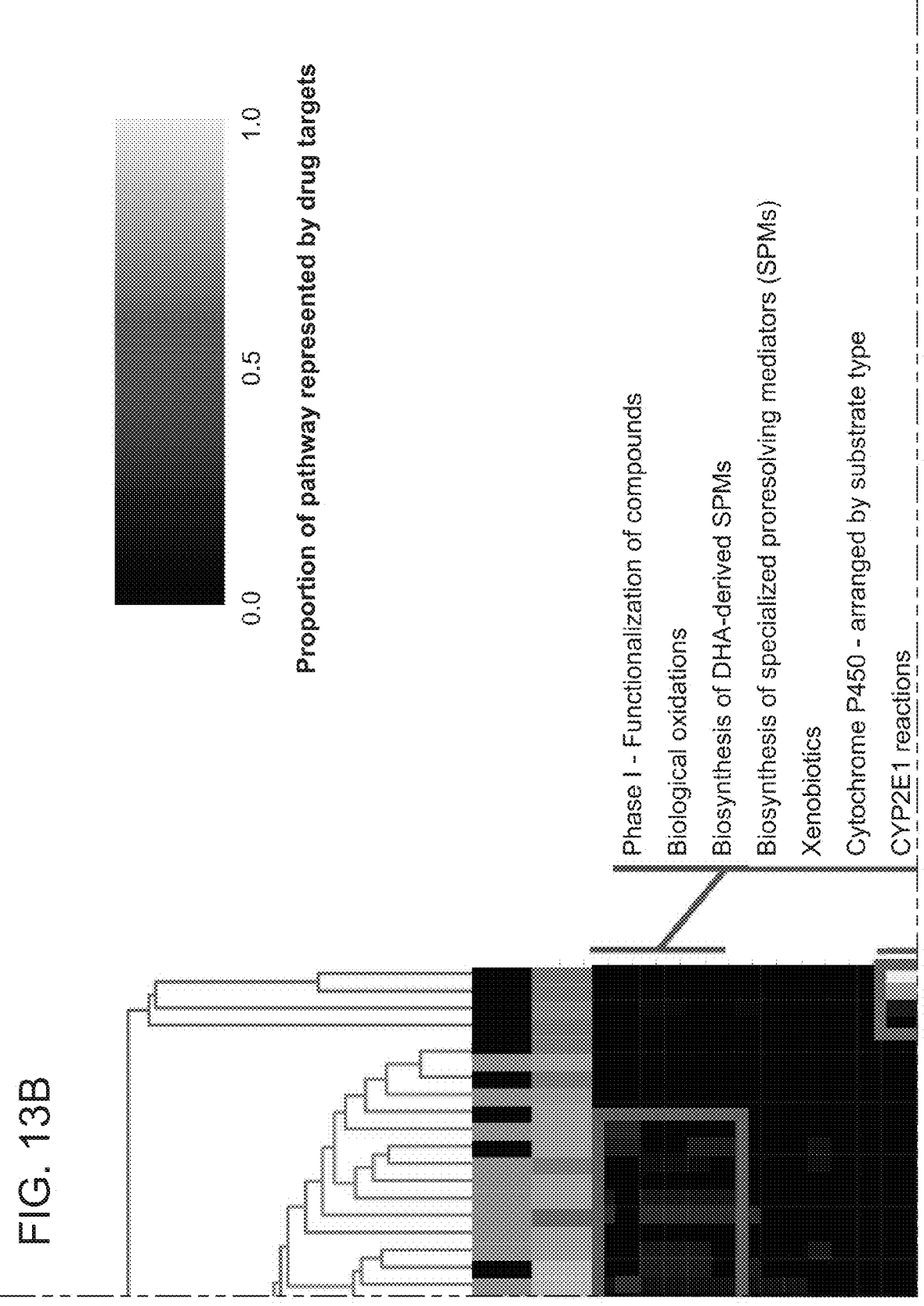
Figure 13C:
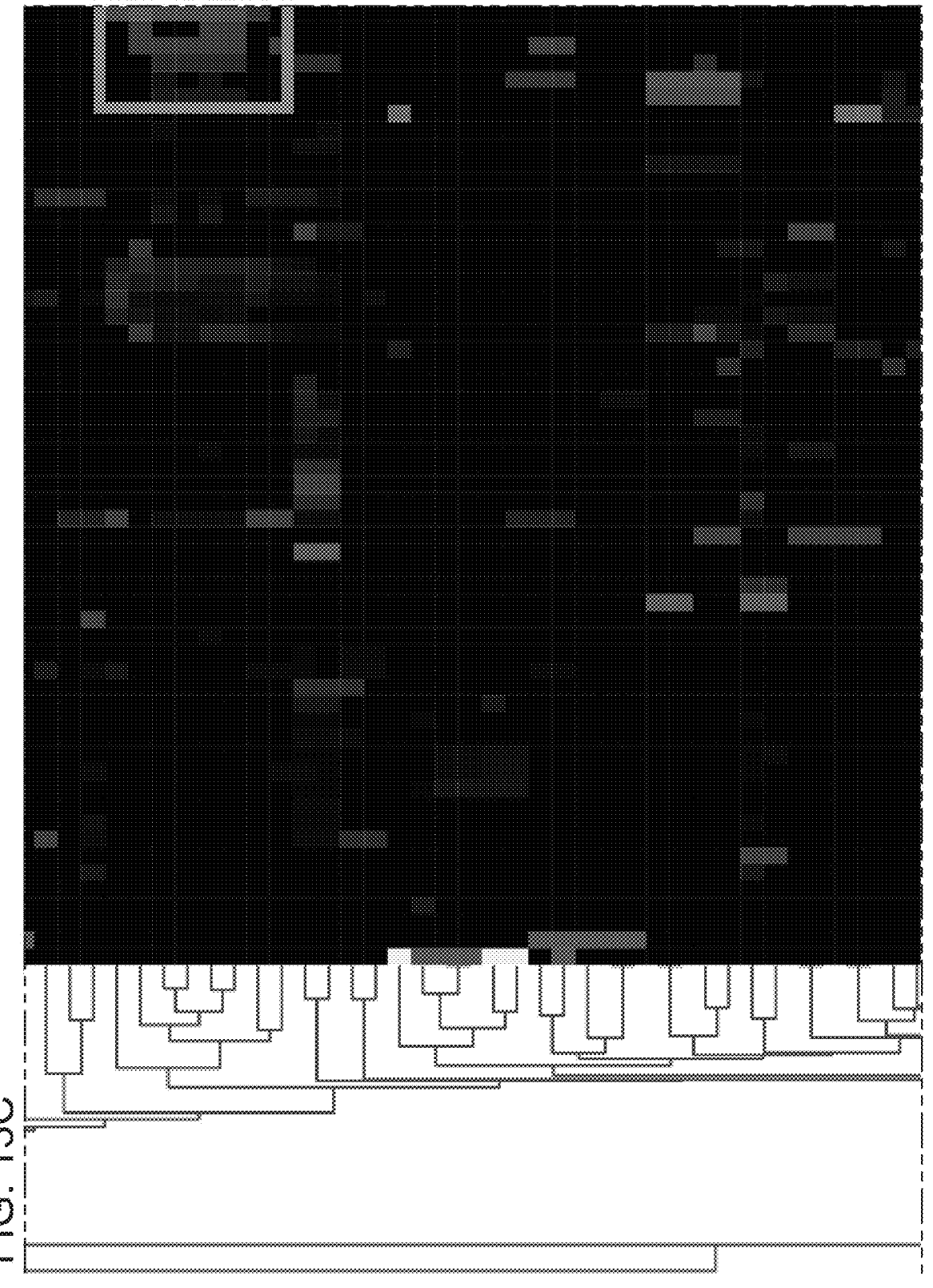
Figure 13E:
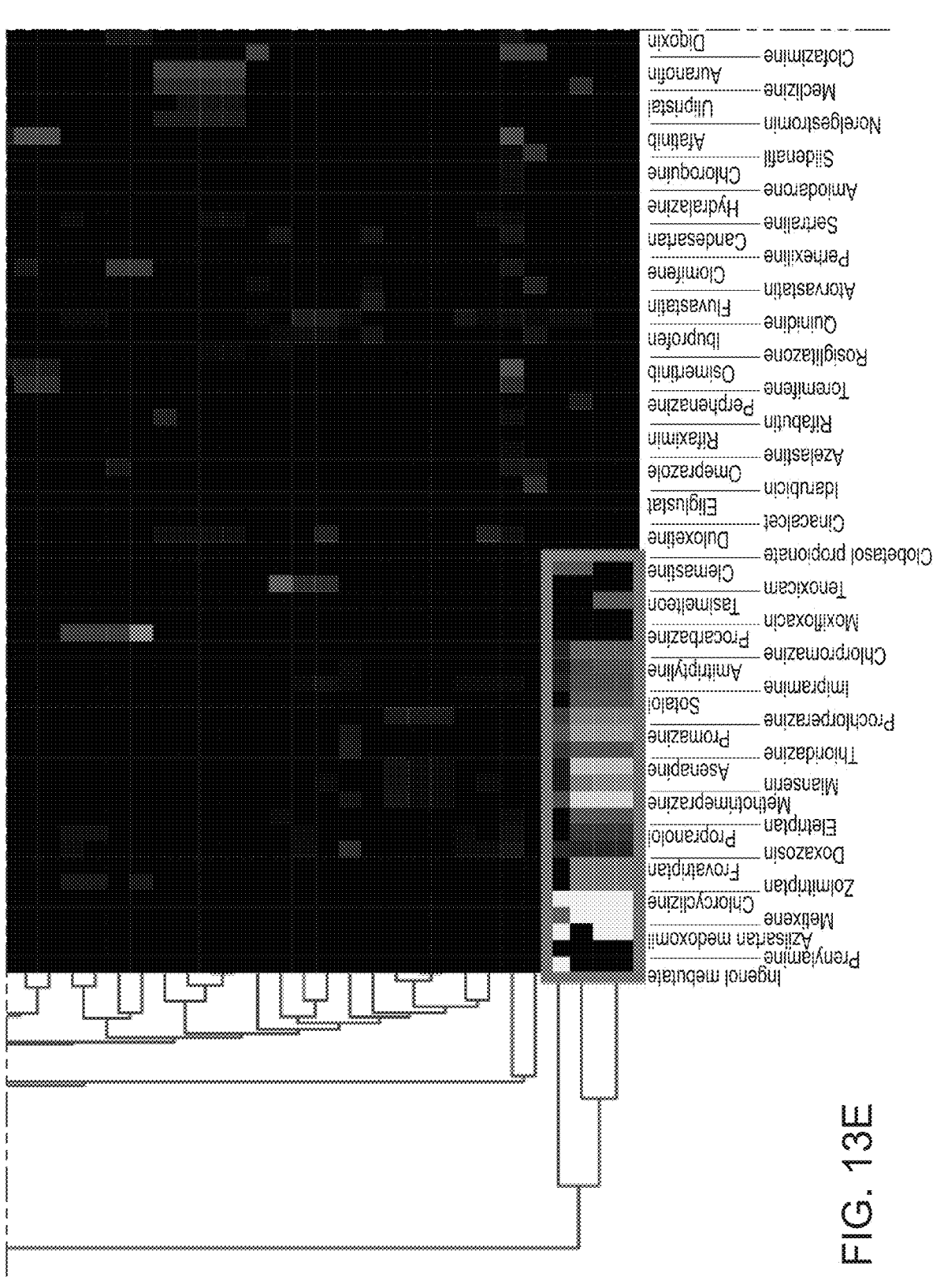
Figure 13F:
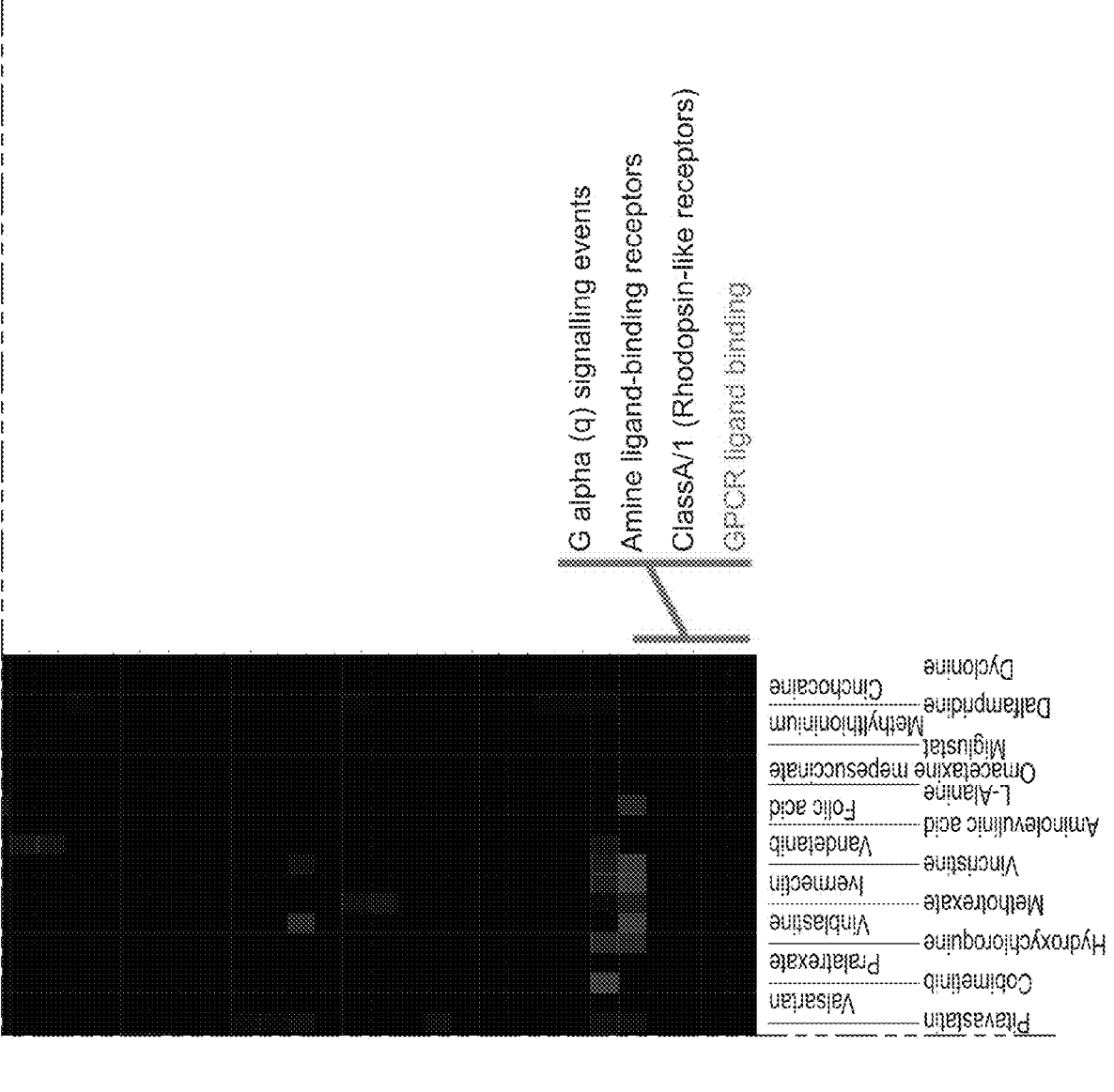
Figure 13H:
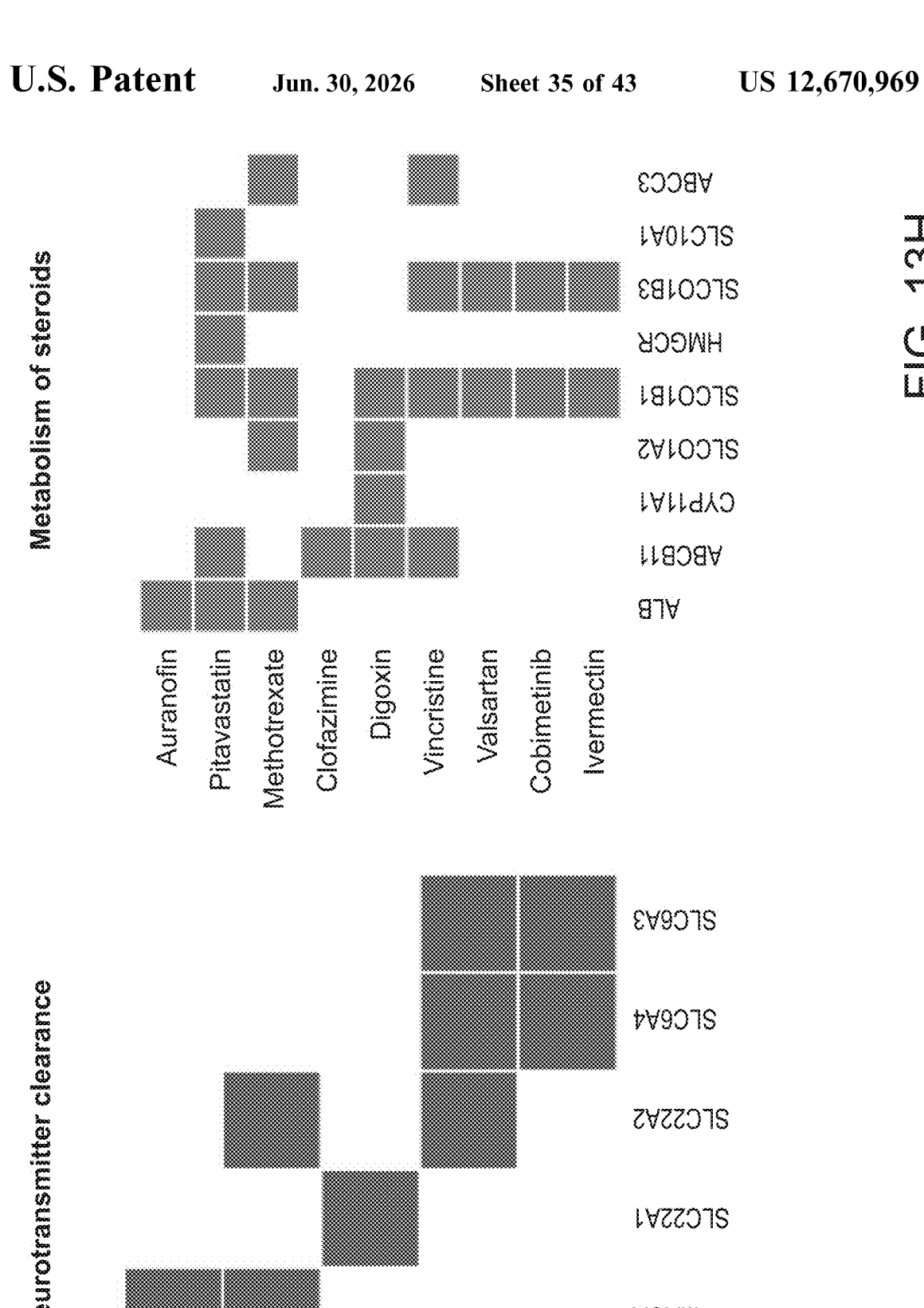
Figure 13I:
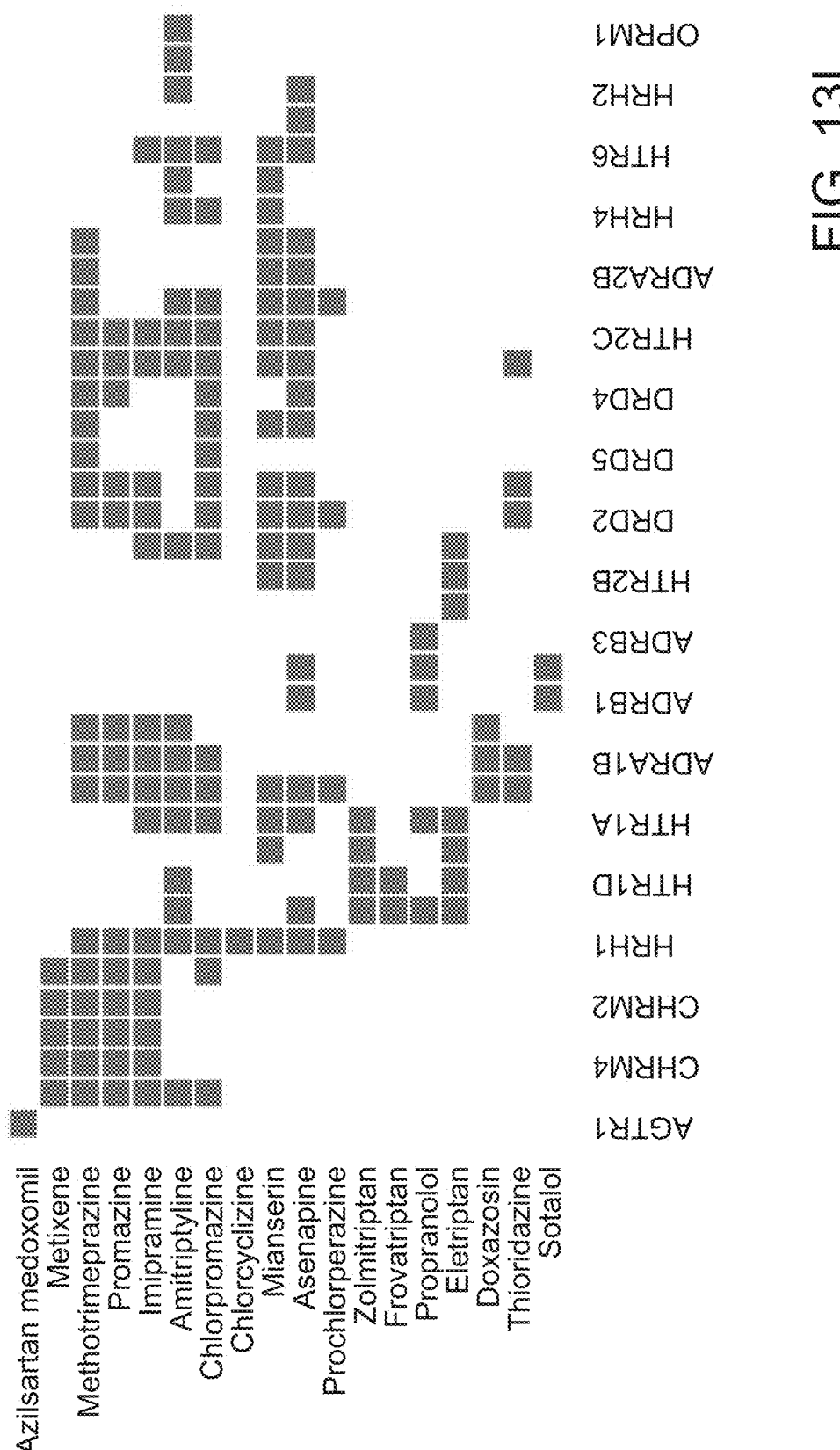
Figures 14A, 14B, 14C, 14D:
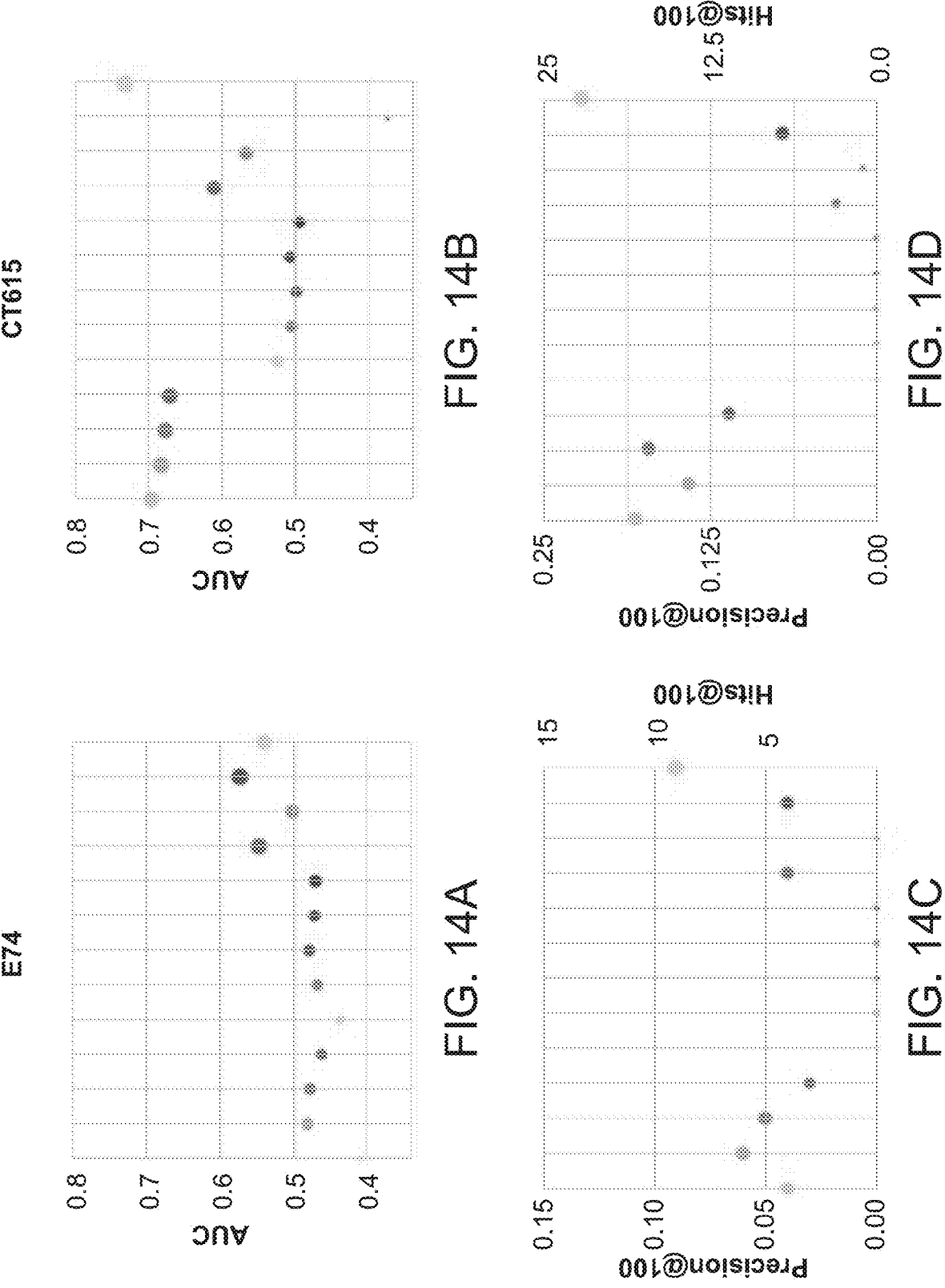
FIGS. 14A-14H are graphs of the performance of different predictive pipelines.
Figure 14F:
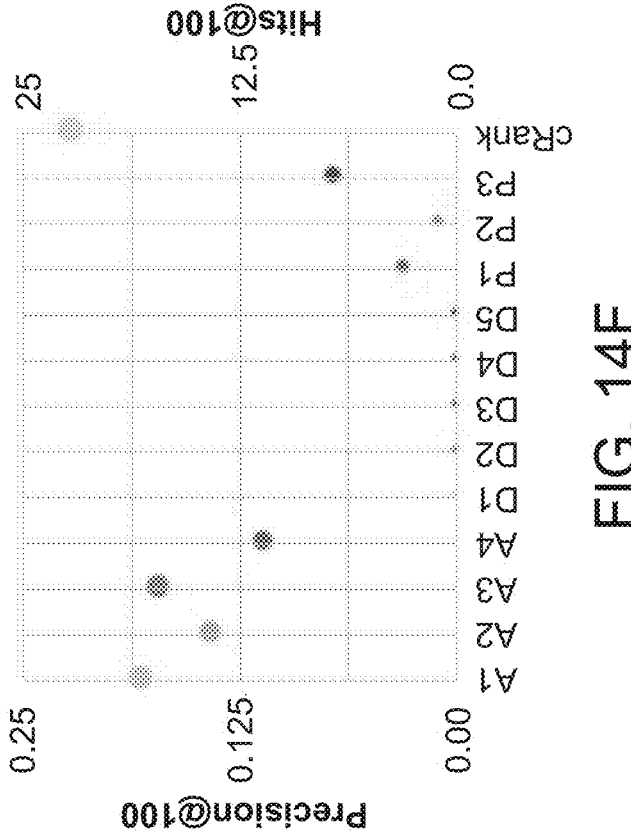
Figure 14E:
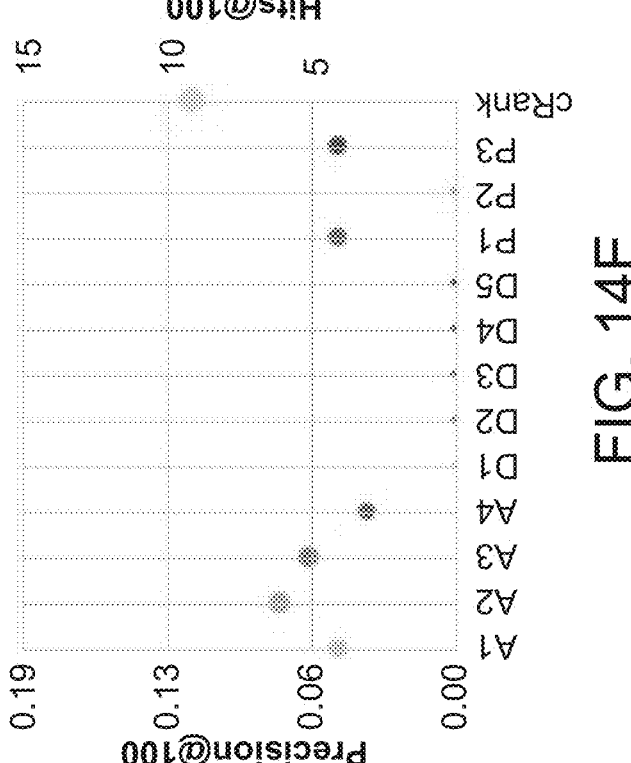
Figure 14H:
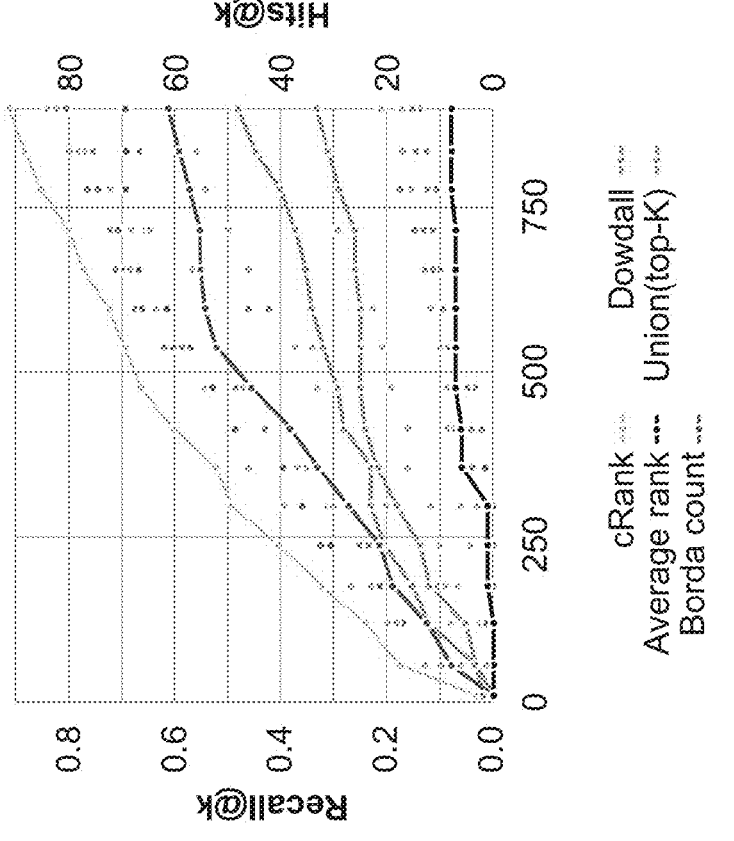
Figure 14G:
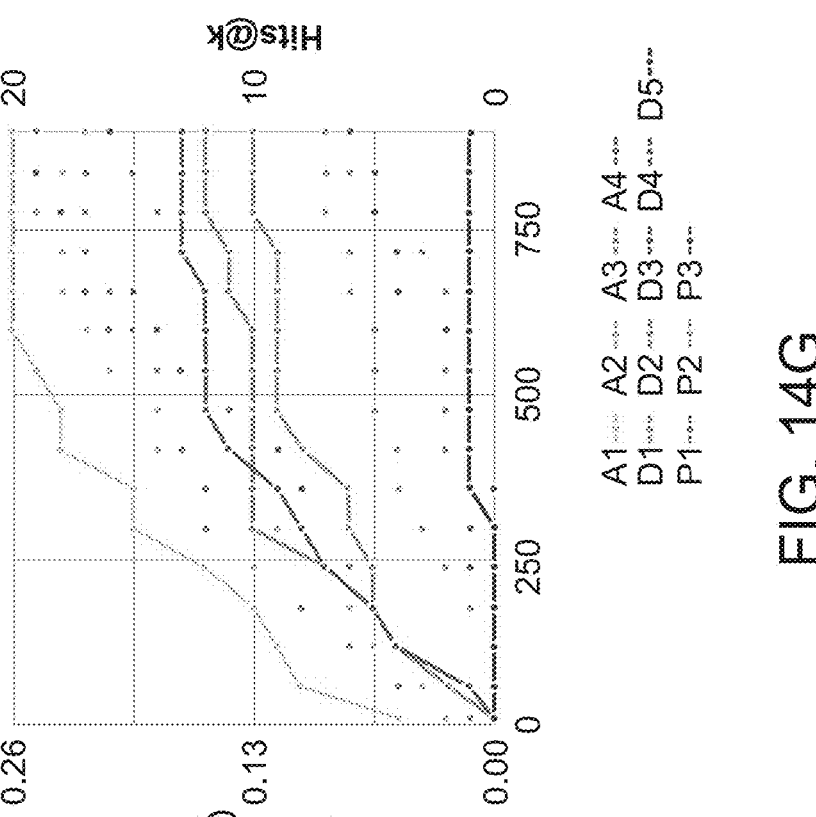

Of the 200 drugs ranked by CRank, 13 had positive outcomes in VeroE6 cells, representing promising drugs candidates that need to be tested further in human cells to confirm their clinical relevance. As chloroquine and hydroxychloroquine have been tested repeatedly in the literature, we experimentally tested the remaining 11 drugs in Huh7 cells, in a nine-point dilution series from 25 μM to 100 nM. Of the 11 compounds tested, auranofin, azelastine, digoxin, and vinblastine show very strong anti-SARS-CoV-2 response; fluvastatin displays a weaker response; and methodextrate is effective only at the highest concentration. Altogether, we found that 6 of the 11 drugs show potential for treating SARS-CoV2 infection (FIGS. 10 and 11).

Inspecting the CRank list and the experimental outcomes, we found three highly ranked drugs with strong outcomes, but not yet in clinical trials (FIG. 19): azelastine (CRank #10, S), an antihistamine used to treat allergic upper airway symptoms; and digoxin (CRank #33, S), used to treat heart failure and atrial fibrillation. Finally, in particular, auranofin (CRank #118, S), used to treat rheumatoid arthritis, also shown to reduce several microbial infections by altering cell redox state and used to treat asthma, shows exceptionally strong response in human cells at clinically relevant concentrations. Our findings, coupled with extensive experience in their use in the clinical community, argue for their consideration in clinical trials. Other highly ranked candidates include methotrexate (CRank #32, S), which impairs folate metabolism and attenuates host inflammatory response in autoimmune diseases. This latter mechanism argues that methotrexate is likely to be effective at the other end of the disease spectrum (i.e., in the face of profound hyperimmune response to the infection).

Example 5. Network Effects

Figure 1C:
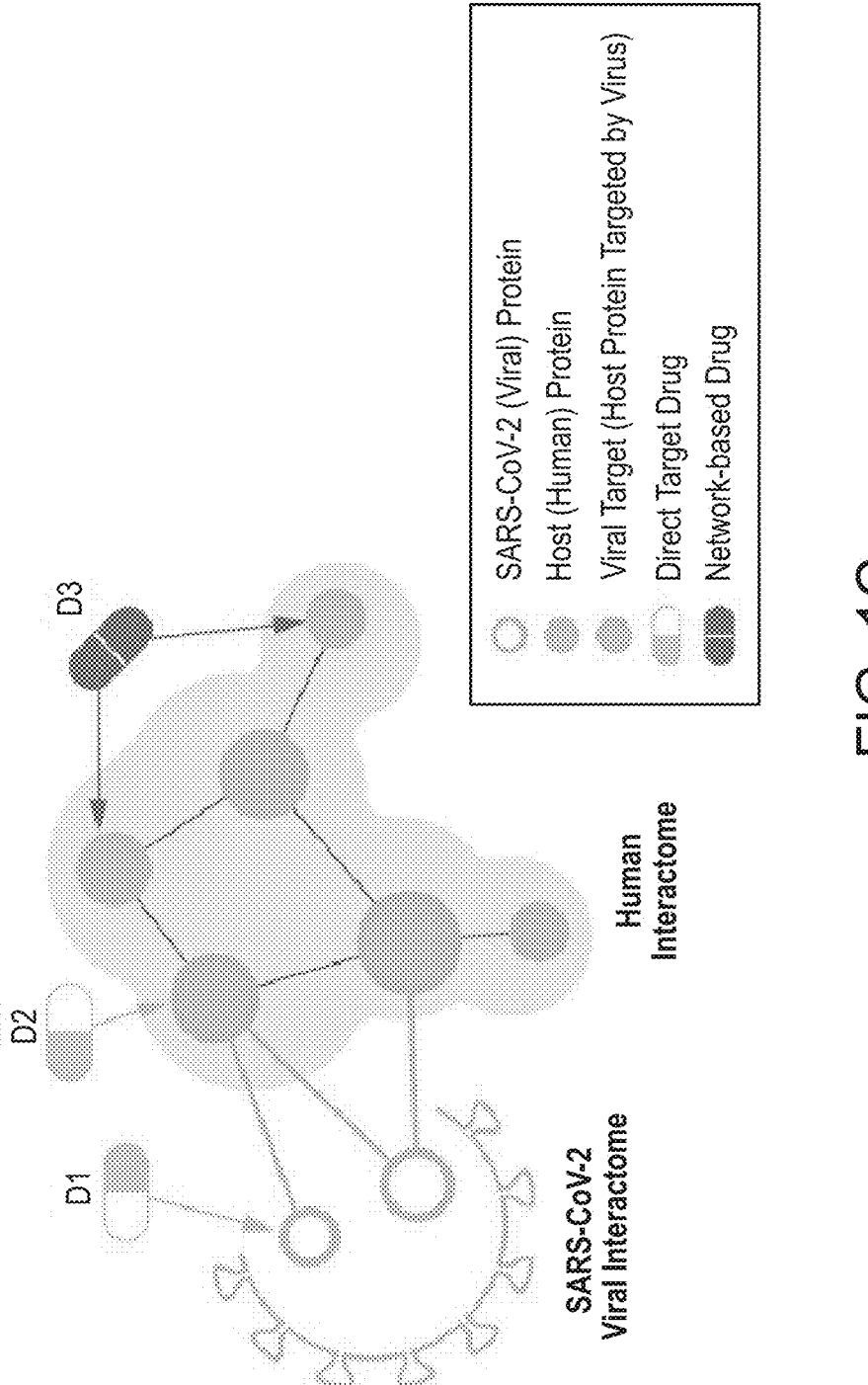

Most computationally informed drug repurposing methods rely on docking patterns and, hence, are limited to compounds that bind either to viral proteins or to the host targets of the viral proteins (FIG. 1C). A good example is remdesivir, a direct-acting antiviral that inhibits viral RNA polymerase. In contrast, our pipelines can also identify drugs that target host proteins to induce network-based perturbations, some of which are likely to alter the virus's ability to enter the cell or replicate within it. In the intact host, these drugs may also act via other mechanisms (such as the anti-inflammatory effects of corticosteroids like dexamethasone), which can only be assessed in animal models or in human trials.

We find that only one of the 77 S&W drugs are known to directly target a viral protein binding target: amitriptyline, which targets SIGMAR1, the target of the NSP6 SARS-CoV-2 protein. In other words, 76 of the 77 drugs that show efficacy in our experimental screen are "network drugs", achieving their effect by perturbing the host subcellular network, representing our third key finding. Indeed, as network drugs do not target viral proteins or their host targets, they cannot be identified using traditional binding-based methods; yet, they are successfully prioritized by network-based methods.

Searching for common mechanistic or structural patterns that could account for the efficacy of the 77 S&W drugs, we explored their target and pathway enrichment profiles (FIGS. 10, 11), as well as their reported mechanisms of action, failing to identify statistically significant features shared by most S&W drugs. This failure is partly explained by the diversity of the S&W drugs, containing antipsychotics (9S & 4W), serotonin receptor agonists (3W), non-steroidal anti-inflammatory drugs (2W), angiotensin receptor blockers (2W), tyrosine kinase inhibitors (5S), statins (1W & 2S), and others.

We did, however, find a connected component formed by the targets of the drugs that were effective viral inhibitors (FIG. 3B), suggesting that even though we failed to find a strong mechanistic pattern common to most drugs, we did find a neighborhood in the interactome that may be implicated with the inhibition of viral replication. Note also that each pipeline relies on different network features, and therefore, captures different reasons as to why a drug may alter the outcome of a disease. Indeed, the proximity pipeline identifies the physical interactions that connect the drug targets to the disease module (see Examples 14-15, herein), offering specific, experimentally testable predictions of the drug's mechanism in the context of the disease. While the A1 and the Diffusion pipelines are not explicit about why they make their predictions, we were able to extract the predictive subgraphs that collect the interactions that may contribute to the therapeutic a mechanism.

As CRank extracts its predictive power from the network, we hypothesized that network-based patterns may help distinguish the S&W drugs from the N drugs. Indeed, we found that the targets of the 37 S drugs form a statistically significant large connected component (Z-Score=2.05), indicating that these targets agglomerate in the same network neighborhood. We observe the same pattern for the targets of the 40 W drugs (Z-Score=3.42). The negative network separation between the S and W drug targets ($S_{SW}$=−0.69) indicates that, in fact, the S and the W drugs target the same network neighborhood. To characterize this neighborhood, we measured the network-based proximity of the targets of the S, W, and N drug classes to the SARS-CoV-2 targets. We found that compared to random expectation, the N drug targets are far from the COVID-19 module (FIG. 3C), while the S and W drug targets are closer to the COVID-19 disease module than expected by chance. The magnitude of the effect is also revealing: the S drug targets are closer than the W drug targets, suggesting that network proximity is a positive predictor of a drug's efficacy.

Taken together, our analyses suggest that S&W drugs are diverse, and lack pathway-based or mechanistic signatures that distinguish them. We did find, however, that S&W drug target the same interactome neighborhood, located in the network vicinity of the COVID-19 disease module, potentially explaining their ability to influence viral effects on host cells, and the effectiveness of network-based methodologies to identify them.

Example 6. Results

A recent in vitro screen of 12,000 compounds in VeroE6 cells identified 100 compounds that inhibit viral infectivity. (See L. Riva et al., Discovery of SARS-CoV-2 antiviral drugs through large-scale compound repurposing. *Nature* 586, 113-119 (2020).) Yet, only 39% of the 12,000 compounds tested are FDA approved, the rest being in the preclinical or experimental phase, years from reaching patients. In contrast, 96% of the 918 drugs prioritized and screened here are FDA approved, and, hence could be moved rapidly to clinical trials. Brute force screening does, however, offer an important benchmark: Its low hit rate of 0.8% highlights the value in prioritizing resources towards the most promising compounds. Indeed, the unsupervised CRank offers an order of magnitude higher (9%) hit rate among the top 100 drugs, and the top 800 of the 6,340 drugs prioritized by CRank contains 58 of the 77 S&W drugs (FIGS. 4G-H). The hit rate can be further increased by expert knowledge and curation. To demonstrate this point, we mimicked the traditional drug repurposing process whereby a physician-scientist manually inspected the top 10% of the CRank consensus ranking on April 15, removing drugs with known significant toxicities in vivo and lower-ranked members of the same drug class, and arrived at 74 drugs available for testing. Using the experimental design described above but over a wider range of doses (0.625-20 μM, 0.2 multiplicity of infection (MOI)), we screened these 74 compounds separately from the E918 list, and found 39 N, 10 W, and 11 S outcomes. The resulting 28% enrichment of S&W drugs suggests that in the case of limited resources, outcomes are maximized by combining algorithmic consensus ranking with expert knowledge. Finally, value of the predictive approach is demonstrated after selecting drugs that in the nonhuman primate screen had a positive outcome for a second human screen, resulting in a success rate of 62%, helping us identify six drugs could be easily repurposed for treating the SARS-CoV2 infection.

Taken together, the methodological advances presented here not only suggest potential drug candidates for COVID-19, but offer a principled algorithmic toolset to identify future treatments for diseases underserved by the cost and the timelines of conventional de novo drug discovery processes. As only 918 of the 6,340 drugs prioritized by CRank were screened, a selection driven by compound availability, many potentially efficacious FDA-approved drugs remain to be tested. Finally, it is also possible that some drugs that lacked activity in VeroE6 cells may nevertheless show efficacy in human cells, like loratadine (rank #95, N), which inhibited viral activity in the human cell line Caco-2 (38). Ritonavir, our top-ranked drug, also showed no effect in our screen, despite the fact that over 42 clinical trials are exploring its potential efficacy in patients. In other words, some of the drugs highly ranked by CRank may show efficacy, even if they are not among the 77 S&W drugs with positive outcomes. Note that a drug can have inhibitory effect in vitro that might not replicate in vivo, as observed for chloroquine and hydroxychloroquine. Moreover, drug combinations could increase the potency of some drugs, and given a synergistic effect, could also improve outcomes.

COVID disease is the product of damage by the virus itself and damage by immune overreaction (cytokine storm). As the assay used for the experimental screening only detects the inhibition of the viral replication cycle, an immunomodulatory drug that reduces the cytokine storm without interfering with virus replication would not show up as a hit in our screen. However, we identify drugs that reduce the viral load enough such that the immune system is not overstimulated, potentially lowering the chance of a cytokine storm.

Example 7. Human Interactome and SARS CoV-2 and Drug Targets

The human interactome was assembled from 21 public databases that compile experimentally derived protein-protein interaction (PPI) data: 1) binary PPIs, derived from high-throughput yeast-two hybrid (Y2H) experiments (HI-Union), three-dimensional (3D) protein structures (Interactome3D, INstruct, Insider), or literature curation (PINA, MINT, LitBM17, Interactome3D, Instruct, Insider, BioGrid, HINT, HIPPIE, APID, InWeb); 2) PPIs identified by affinity purification followed by mass spectrometry present in BioPlex, QUBIC, CoFrac, HINT, HIPPIE, APID, LitBM17, and InWeb; 3) kinase substrate interactions from KinomeNetworkX and PhosphoSitePlus; 4) signaling interactions from SignaLink and InnateDB; and 5) regulatory interactions derived by the ENCODE consortium. We used the curated list of PSI-MI IDs provided by Alonso-López, et al. (see Di. Alonso-López, et al., APID database: Redefining protein-protein interaction experimental evidences and binary interactomes. *Database* 2019, 1-8 (2019)) for differentiating binary interactions among the several experimental methods present in the literature-curated databases. For InWeb, interactions with curation scores <0.175 (75th percentile) were not considered. All proteins were mapped to their corresponding Entrez ID (NCBI) and the proteins that could not be mapped were removed. The final interactome used in our study contains 18,505 proteins, and 327,924 interactions. We retrieved interactions between 26 SARS-CoV-2 proteins and 332 human proteins reported by Gordon, et. al. (2020) (see D. E. Gordon, et al., A SARS-CoV-2-Human Protein-Protein Interaction Map Reveals Drug Targets and Potential Drug-Repurposing. bioRxiv, 2020.03.22.002386 (2020)). We retrieved drug target information from the DrugBank database, which contains 24,609 interactions between 6,228 drugs and their 3,903 targets, and drug target interaction data curated from the literature for 25 drugs. We also obtained from the DrugBank database differentially expressed genes (DEGs) identified by exposure of drugs to different cell lines. The Largest Connected Component (LCC) of human proteins that bind to SARS-CoV-2 proteins was calculated using a degree-preserving approach, which prevents the repeated selection of the same high degree nodes, setting 100 degree bins in 1,000 realizations.

Example 8. Lung Gene Expression (FIG. 2A)

We evaluated gene expression in the lung by using the GTEX database, considering genes with a median count lower than 5 transcripts (raw counts) as not expressed.

Example 9. Disease Comorbidities

Pre-existing conditions worsen prognosis and recovery of COVID-19 patients. Previous work showed that the disease relevance of human proteins targeted by a virus can predict the signs, symptoms, and diseases caused by that pathogen. This prompted us to identify diseases whose molecular mechanisms overlap with cellular processes targeted by SARS-CoV-2, allowing us to predict potential comorbidity patterns. We retrieved 3,173 disease-associated genes for 299 diseases, finding that 110 of the 332 proteins targeted by SARS-CoV-2 are implicated in other human diseases; however, the overlap between SARS-CoV-2 targets and the pool of the disease-associated genes was not statistically significant (Fisher's exact test; FDR-BH $p_{adj}$–value>0.05). We evaluated the network-based overlap between the proteins associated with each of the 299 diseases and the host protein targets of SARS-CoV-2 using the $S_{vb}$ metric, where $S_{vb}<0$ signals a network-based overlap between the SARS-CoV-2 viral targets v and the gene pool associated with disease b. We Found that $S_{vb}>0$ for each disease, indicating that COVID-19 disease module does not directly overlap with any major disease module (FIG. 5). The diseases closest to the COVID-19 disease module (smallest $S_{vb}$) included several cardiovascular diseases and cancers, whose comorbidity in COVID-19 patients is well documented (FIG. 6). The same metric predicted comorbidity with neurological diseases, in line with our observation that the host protein targets are expressed in the brain.

In summary, we found that the SARS-CoV-2 host protein targets do not overlap with proteins associated with any major diseases, indicating that a potential COVID-19 treatment cannot be derived from the arsenal of therapies approved for a specific disease. These findings argue for a strategy that maps drug targets without regard to their localization within a particular disease module. However, the disease modules closest to the SARS-CoV-2 viral targets are those with noted comorbidity for COVID-19 infection, such as pulmonary and cardiovascular diseases. We also found multiple network-based evidences linking the virus to the nervous system, a less explored comorbidity, consistent with the observations that many infected patients initially lose olfactory function and taste, and 36% of patients with severe infection who require hospitalization have neurological manifestations.

Example 10. Drug Repurposing Prediction Algorithms

To obtain drug repurposing predictions we implemented three algorithmic approaches: i) Artificial Intelligence Based Algorithm (A1-A4); ii) Diffusion-Based Algorithms (D1-D5) and iii) Proximity Based Algorithms (P1-P3). The AI algorithm is a graph neural network (GNN) architecture that takes as input a multimodal graph with three types of nodes (representing drugs, proteins, and diseases) and edges capturing different types of interactions between these nodes. The algorithm generates embedding vectors of drug and disease nodes, which are then used to predict drug scores, representing how promising a given drug is for COVID-19. The diffusion-based algorithms are inspired by the diffusion state distance (DSD). They use a diffusion property to define a similarity metric for node pairs, taking into account how similar the nodes are in terms of how they affect the rest of the network. Once pairwise similarity scores between all nodes are obtained, we calculate how similar drug targets are to the pool of SARS-CoV-2 proteins. This indicates how likely drug targets reverse the impact of the SARS-CoV-2 proteins. Finally, the proximity measure is based on the average shortest path from a drug target to a SARS-CoV-2 target.

Example 11. Artificial Intelligence Based Algorithm (A1-A4)

Figure 7:
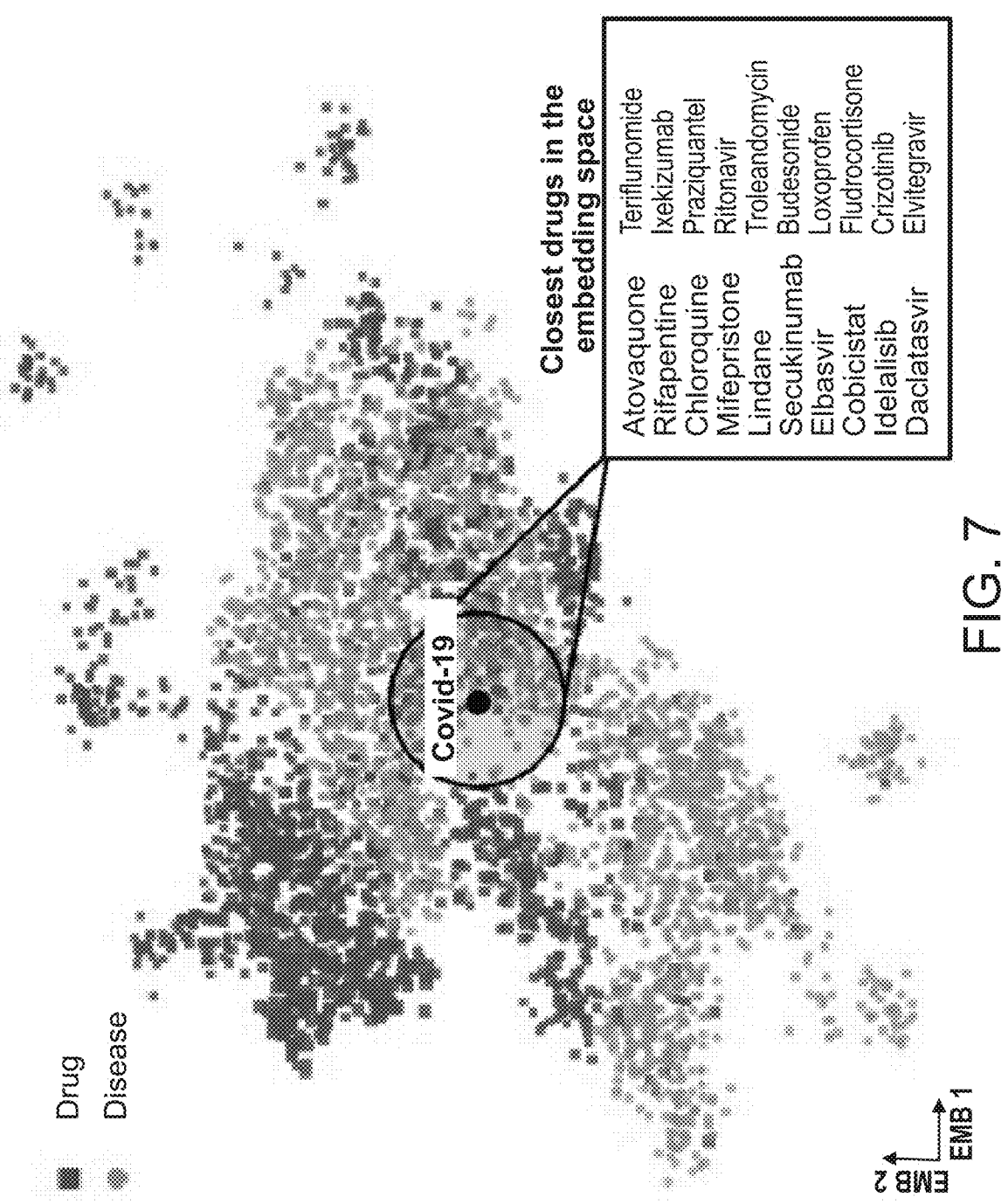
FIG. 7 is a visualization of drug and disease embeddings in an AI-based strategy for drug repurposing.
Figures 8A, 8B:
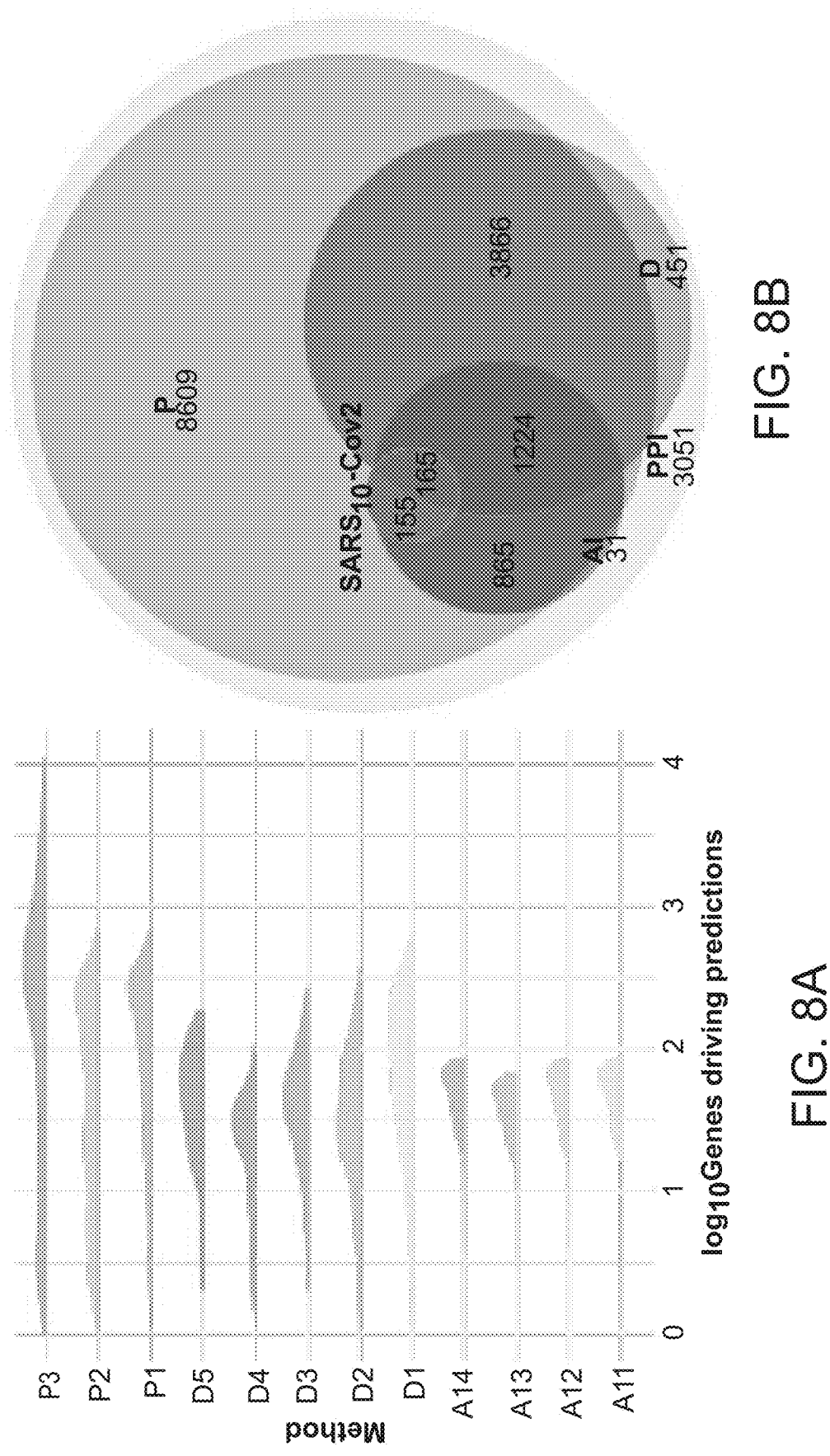
FIGS. 8A-8D illustrate similarities and differences of the explanatory subgraphs.
Figures 8C, 8D:
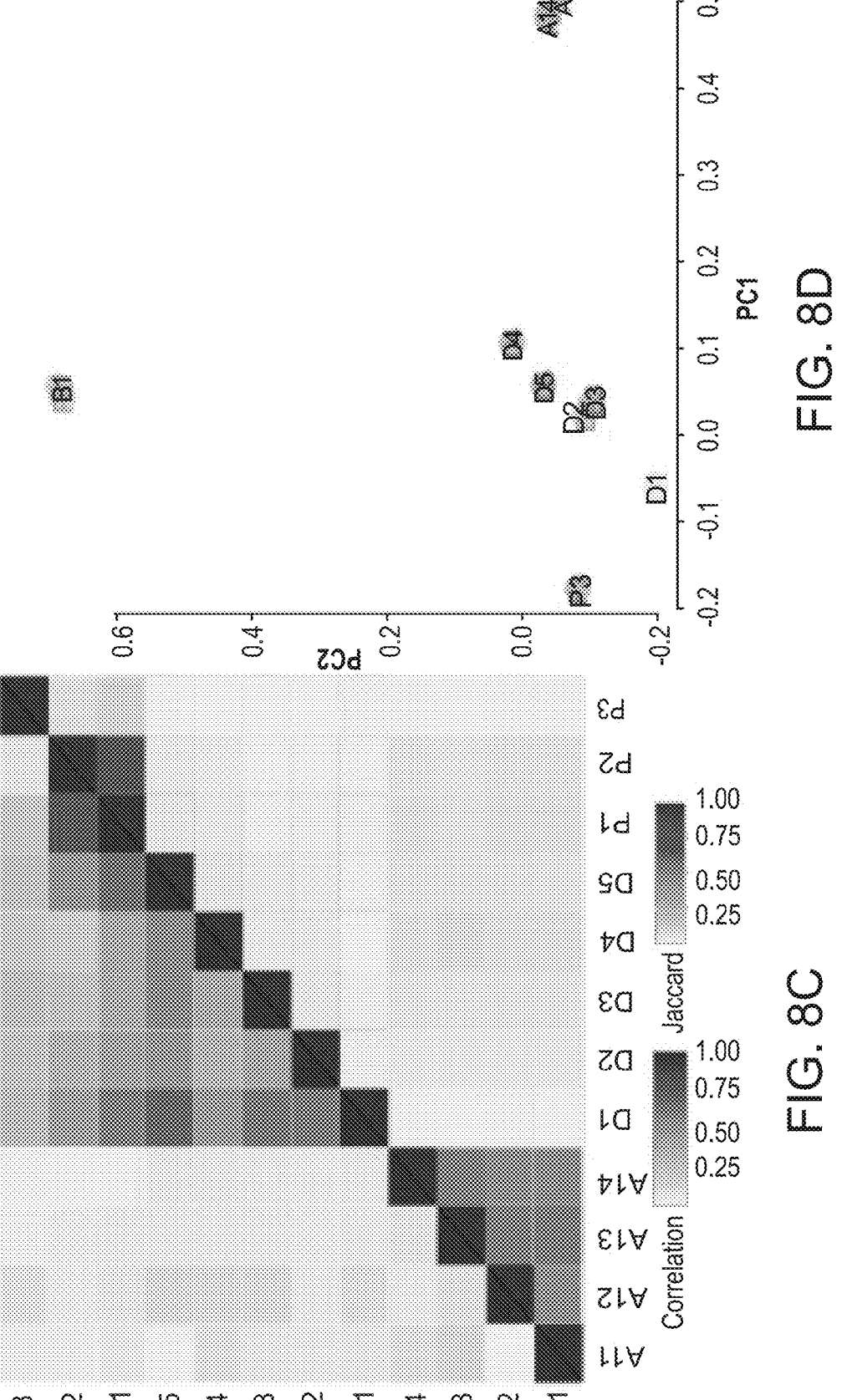
Figure 9A:
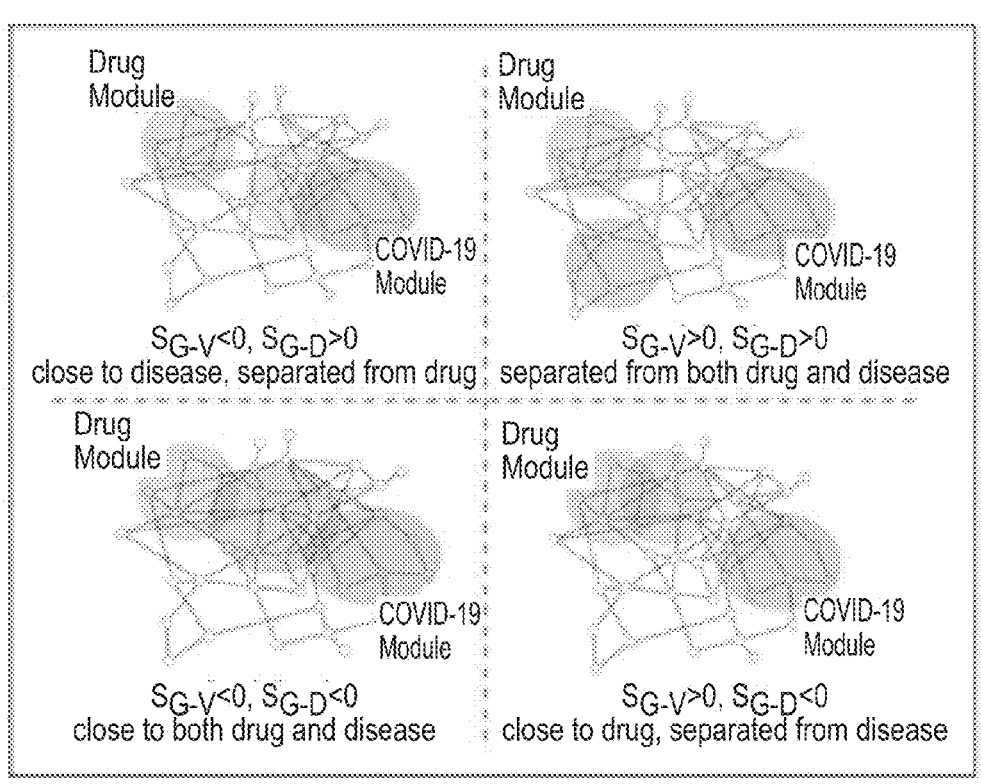
FIGS. 9A-9D illustrate separation plots for 320 drugs. For each drug, the predictive subgraph for each predictive pipeline was identified. For each subgraph G, the separation between the subgraph G and drug targets was computed as $S_{G-D}$, and separation between the subgraph and SARS-CoV-2 targets as $S_{G-V}$. Each subgraph was plotted as a dot with the two separation values as coordinates.
Figure 9B:
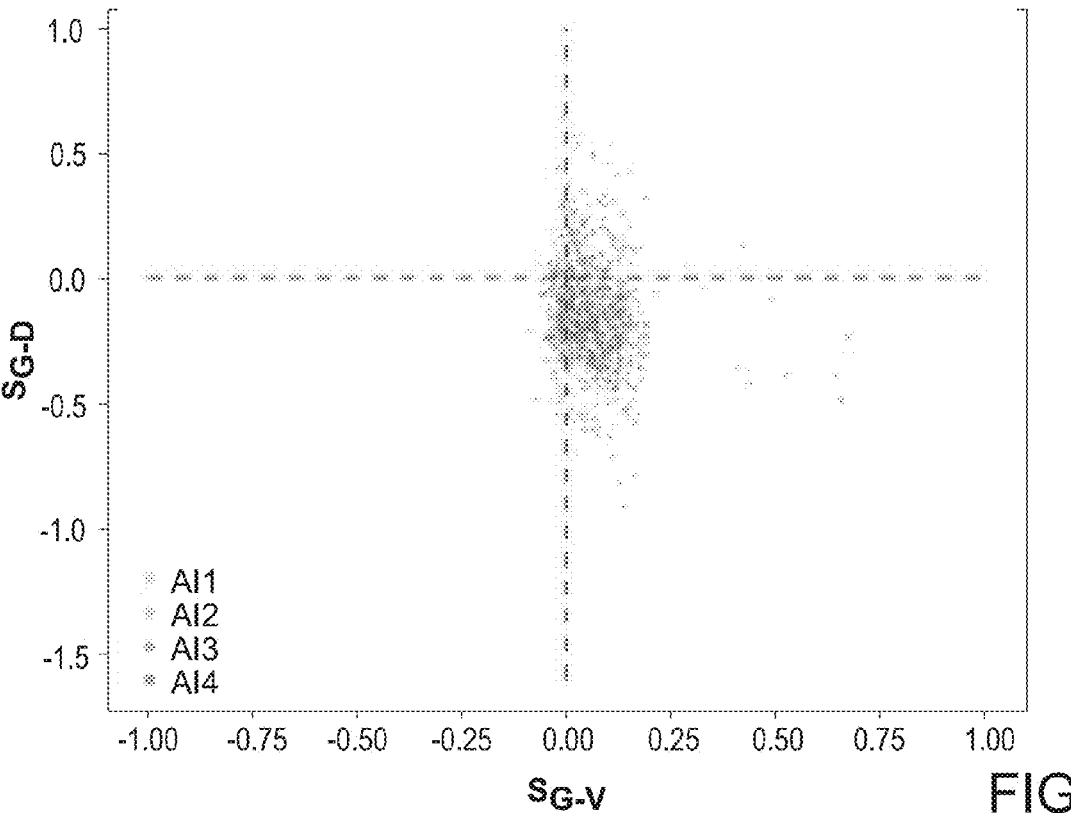
Figures 9C, 9D:
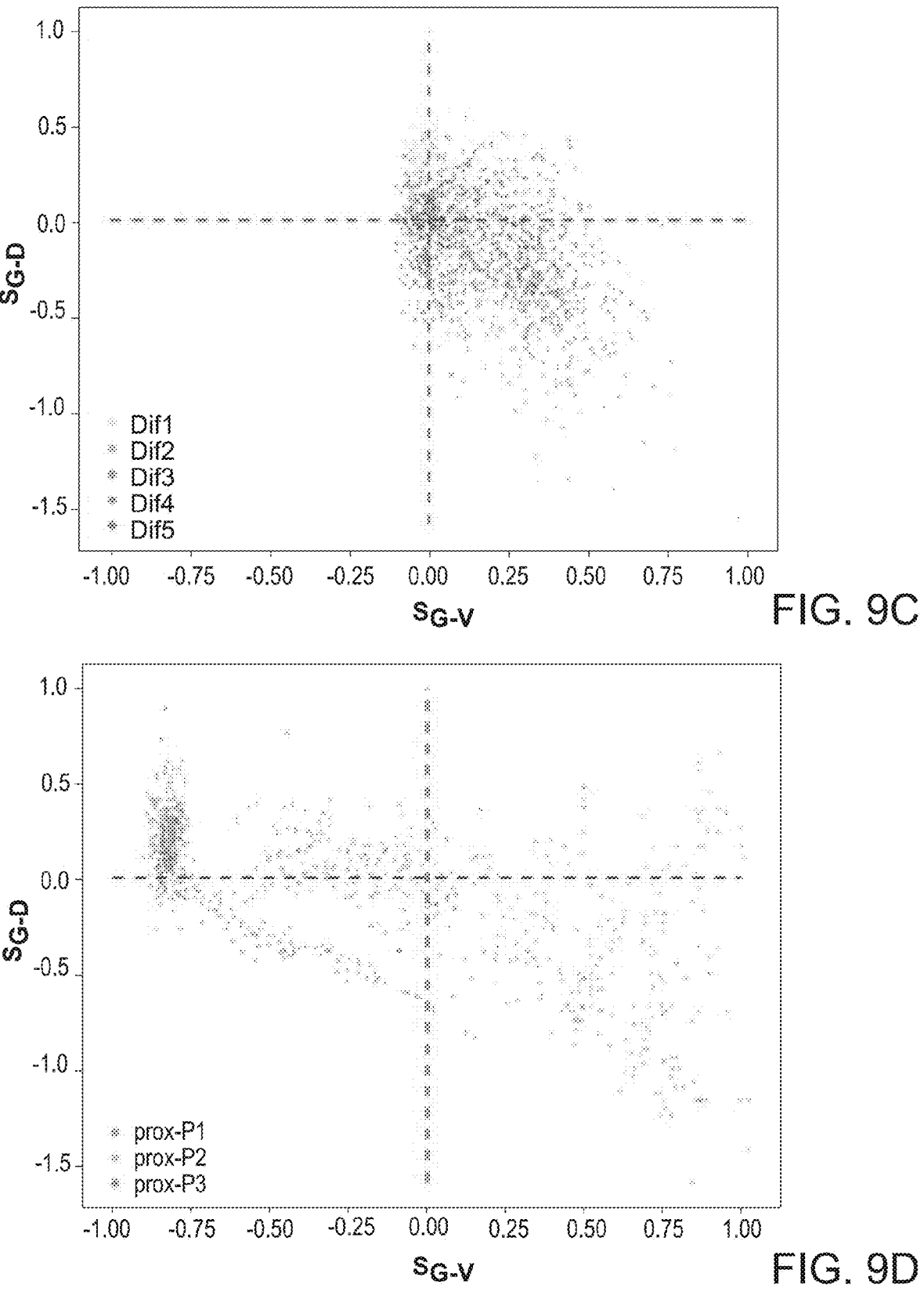

We designed a graph neural network for COVID-19 treatment recommendations based on a previously developed graph neural network (GNN) architecture (FIG. 7), described in M. Zitnik, M. Agrawal, J. Leskovec, Modeling polypharmacy side effects with graph convolutional networks. *Bioinformatics* 34, i457-i466 (2018). The multimodal graph is a heterogeneous graph G=(V, R) with N nodes $v_i \in V$ representing three distinct types of biomedical entities (i.e., drugs, proteins, diseases), and triplets, i.e., labeled edges $(v_i, r, v_j) \in R$ representing four semantically distinct types of edges r between the entities (i.e., protein-protein interactions, drug-target associations, disease-protein associations, and drug-disease indications).

COVID-19 drug treatment recommendation task. We cast the COVID-19 treatment recommendation task as a link prediction problem on the multimodal graph. The task was to predict new edges between drug and disease nodes such that a predicted link between a drug node $v_i$ and a disease node $v_j$ should carry the meaning that the drug $v_i$ is indicated for the disease $v_j$ (i.e., the drug has a known positive therapeutic effect in patients with the disease, e.g., COVID-19). Parameters of the GNN model were optimized during training to maximize the model's ability to predict examples of known and approved drug-disease indications. This process produced embeddings for drug and disease nodes in the graph that were predictive of therapeutic indications, and we used the embeddings to construct ranked lists of candidate drugs for COVID-19.

Overview of graph neural architecture. Our graph neural network is an end-to-end trainable model for link prediction on the multimodal graph and has two main components: (1) an encoder: a graph convolutional network operating on G and producing embeddings for nodes in G; and (2) a decoder: a model optimizing embeddings such that they are predictive of known drug-disease indications. The neural message-passing encoder took as input a graph G and produced a node d-dimensional embedding $z_i \in R^d$ for every drug and disease node in the graph.

We used the encoder that learned a message-passing algorithm and aggregation procedure to compute a function of the entire graph that transformed and propagated information across graph G. The graph convolutional operator took into account the first-order neighborhood of a node and applied the same transformation across all locations in the graph. Successive application of these operations then effectively convolved information across the Kth order neighborhood (i.e., embedding of a node depends on all the nodes that are at most K steps away), where K is the number of successive operations of convolutional layers in the neural network model. The graph convolutional operator takes the form $$ h_i^{(k+1)} = \phi\left( \sum_r \sum_{j \in N_r^i} \alpha_r^{ij} W_r^{(k)} h_j^{(k)} + \alpha_r^i h_i^{(k)} \right), \qquad (1) $$

where $h_i^{(k)} \in R^{d(k)}$ is the hidden state of node $v_i$ in the $k^{th}$ layer of the neural network with d(k) being the dimensionality of this layer's representation, r is an edge type, matrix $W_r^{(k)}$ is an edge-type specific parameter matrix, $\phi$ denotes a non-linear element-wise activation function (i.e., a rectified linear unit), and $\alpha_r$ denote attention coefficients. To arrive at the final embedding $z_i \in R^d$ of node $v_i$, we compute its representation as $z_i = h_i^{(k)}$. Next, the decoder takes node embeddings and combines them to reconstruct labeled edges in G. In particular, the decoder scores a $(v_i, r, v_j)$ triplet through a function g whose goal is to assign a score $g(v_i, r, v_j)$ representing how likely it is that drugs $v_i$ will treat disease $v_j$ (i.e., r denotes an 'indication' relationship).

Training the graph neural network. During model training, we optimized model parameters using the max-margin loss functions to encourage the model to assign higher probabilities to successful drug indications $(v_i, r, v_j)$ than to random drug-disease pairs. We took an end-to-end optimization approach that jointly optimized over all trainable parameters and propagated loss function gradients through both the encoder and the decoder. To optimize the model, we trained it for a maximum of 100 epochs (training iterations) using the Adam optimizer with a learning rate of 0.001. We initialized weights using the initialization described in X. Glorot, Y. Bengio, Understanding the difficulty of training deep feedforward neural networks in AISTATS, (2010), pp. 249-256. To make the model comparable to other drug repurposing methodologies in this study, we did not integrate additional side information into node feature vectors; instead, we used one-shot indicator vectors as node features. Additional examples of low-dimensional embedding are described in W. Hamilton, P. Bajaj, M. Zitnik, D. Jurafsky, J. Leskovec, Embedding logical queries on knowledge graphs in NIPS, (2018), pp. 2026-2037. For the model to generalize well to unobserved edges, we applied a regular dropout to hidden layer units. In practice, we used efficient sparse matrix multiplications, with complexity linear in the number of edges in G, to implement the model. We used a 2-layer neural architecture with $d_1=32$, $d_2=32$, $d_1=128$ hidden units in input, output, and intermediate layer, respectively; a dropout rate of 0.1; and a max-margin of 0.1. We used mini-batching by sampling triplets R from the multimodal graph G. That is, we processed multiple training mini-batches (mini-batches are of size 512), each obtained by sampling only a fixed number of triplets, resulting in dynamic batches that changed during model training.

Constructing ranked lists of candidate drugs for COVID-19. We generated four lists of candidate drugs for COVID-19. To generate the lists, we used embeddings returned by the graph neural network, in particular, embeddings learned for nodes representing either COVID-19 or drugs in multimodal graph G. The pipeline A1 searches for drugs that are in the vicinity of the COVID-19 disease by calculating the cosine distance between COVID-19 and all drugs in the decoded embedding space. The decoding is based on the N=10 nearest neighboring nodes in the embedding space, with a minimum distance between nodes of D=0.25. The pipeline A2 prevents that nodes in the decoding embedding space from packing together too closely, by using D=0.8 and keeping N unchanged. These constraints push the structures apart into softer, more general features, offering a better overarching view of the embedding space at the loss of the more detailed structure. Pipeline A3 forces the decoding to concentrate on the very local structure by using N=5, to explore a smaller neighborhood, while setting the minimum distance at a midrange point of D=0.5. Pipeline A4 focuses on a broader view of the embedding space by setting N=10 and D=1. Finally, to obtain lists of candidate drugs, each pipeline ranked drugs based on the pipeline-defined distances of drugs to COVID-19 (Figure S3). Intuitively, parameter N constrained the size of the local neighborhood each pipeline looked at in the embedding space when calculating the distances, and parameter D controlled how tightly the pipeline was allowed to pack the embeddings together.

Example 12. Diffusion-Based Algorithms (D1-D5)

The diffusion state distance (DSD) algorithm uses a graph diffusion property to derive a similarity metric for pairs of nodes that takes into account how similarly they affect the rest of the network. We calculate the expected number of times He(A,B) that a random walker starting at node A visits node B, representing each node by the vector:

$$He(V_i) = [He(V_i, V_2), He(V_i, V_3), \ldots, He(V_i, V_n)], \tag{2}$$

which describes how a perturbation initiated from that node affects other nodes in the interactome. The similarity between nodes A and B is provided by the L1-norm of their corresponding vector representations:

$$DSD(A, B) = \|He(A) - He(B)\|. \tag{3}$$

Inspired by the DSD, we developed five new metrics to calculate the impact of drug targets T on the SARSCoV-2 targets V. The first (Pipeline D1) is defined as:

$$I_{DSD}^{min} = \frac{1}{\|T\|} \sum_{t \in T} \min_{v \in V} DSD(t, v), \tag{4}$$

where DSD(s,t) represents the diffusion state distance between nodes t and v. Since the L1-norm of two large vectors may result in loss of information, we also used the metrics (Pipeline D2):

$$I_{KL}^{min} = \frac{1}{\|T\|} \sum_{t \in T} \min_{v \in V} KL(t, v) \tag{5}$$

and (Pipeline D3):

$$I_{KL}^{med} = \frac{1}{\|T\|} \sum_{t \in T} \text{median}_{v \in V} KL(t, v), \tag{6}$$

where KL is the Kullback-Leibler (KL) divergence between the vector representations of the nodes t and s.

Finally, to provide symmetric measures, we tested the metrics (Pipeline D4):

$$I_{JS}^{min} = \frac{1}{\|T\|} \sum_{t \in T} \min_{v \in V} JS(t, v) \tag{7}$$

and (Pipeline D5)

$$I_{JS}^{med} = \frac{1}{\|T\|} \sum_{t \in T} \text{median}_{v \in V} JS(t, v). \tag{8}$$

where JS is the Jensen Shannon (JS) divergence between the vector representations of nodes t and s. All five measures assume t≠s.

Example 13. Proximity Algorithm (P1-P3)

Given V, the set of COVID-19 virus targets, T, the set of drug targets, and d(v,t), the shortest path length between nodes v∈V and t∈T in the network, we define[21]:

$$d_c(V, T) = \frac{1}{\|T\|} \sum_{t \in T} \min_{v \in V} d(v, t). \tag{9}$$

We determined the expected distances between two randomly selected groups of proteins, matching the size and degrees of the original V and T sets. To avoid repeatedly selecting the same high degree nodes, we use degree-binning. The mean $\mu_d(V,T)$ and standard deviation $\sigma_d(V,T)$ of the reference distribution allows us to convert the absolute distance $d_c$ to a relative distance $Z_{dc}$, defined as:

$$Z_{d_c} = \frac{d_c - \mu_{d_c}(V, T)}{\sigma_{d_c}(V, T)}. \tag{10}$$

We implemented three versions of the proximity algorithm: 1) relying on all drug targets (P1); 2) ignoring drug targets identified as drug carriers, transporters, and drug-metabolizing enzymes—and therefore removing all proteins that had functions involved in drug delivery and metabolism (P2); and 3) based on differentially expressed genes (DEGs) identified by exposure of each drug to cultured cells, which was obtained from DrugBank's compilation of 17,222 DEGs linked to 793 drugs in multiple cell lines. P2 aims to understand if the role of proteins involved in drug delivery and drug metabolism can improve the prediction power of the proximity measure and P3 aims to understand if the use of differentially expressed genes under the presence of the drug—instead of binding information—was able to improve the proximity's accuracy.

Example 14. Network Properties of Prediction Algorithms—Explanatory Subgraphs For each pipeline, we identified "explanatory subgraphs" to help understand the predictions made by the respective pipeline. The key idea was to summarize where in the data the pipeline looks for evidence for their predictions. Given a particular prediction, an explanatory subgraph is a small sub-network of the entire network considered by the pipeline that is most influential for the prediction and contributes most to the predictive power. For the proximity method (P), the explanatory subgraphs can be derived exactly, representing the set of nodes contributing to proximity. For the artificial intelligence-based methods (A), the subgraphs were extracted using a GNN Explainer algorithm. GNNExplainer specifies an explanation as a subgraph of the entire network the GNN was trained on, such that the subgraph maximizes the mutual information with the GNN's prediction. This is achieved by formulating a mean field variational approximation and learning a realvalued graph mask, which selects the important subgraph using counterfactual reasoning. For the diffusion method, we first identified the SARS-CoV-2 targets (seeds) that have the maximum (or median, depending on the pipeline) similarity with the drug targets under consideration. Once the seeds are identified for each drug target, we extract the vector representation of the target and the corresponding seeds. Each element of these vectors corresponds to a node in the network:

$$t\colon [r_1, r_2, r_3, \dots, r_n]$$

$$s\colon [w_1, w_2, w_3, \dots, w_n]$$

Each pipeline performs an element-wise comparison of these two vectors to calculate similarity values, defined as similarity terms, using:

$$term_i^{DSD}(t, s) = |r_i - w_i| \qquad (11)$$

$$term_i^{KL}(t, s) = r_i \log\!\left(\frac{r_i}{w_i}\right) \qquad (12)$$

$$term_i^{JS}(t, s) = \frac{1}{2}\left[r_i \log\!\left(\frac{r_i}{m_i}\right) + w_i \log\!\left(\frac{w_i}{m_i}\right)\right], \; m_i = \frac{r_i + w_i}{2} \qquad (13)$$

These distance similarity terms collectively contribute to each drug's ranking score. Among all 18,446 nodes, we are only interested in those whose variations lead to the current ranking (drug prediction scores). Therefore, we applied a feature selection algorithm to eliminate the network nodes (features) that do not contribute to the predicted scores (outcomes). This task is done by training a regression tree model (DecisionTreeRegressor model, from Python 3 scikit-learn package) where feature values are the similarity terms (as defined above) between drug targets and the corresponding seeds. This resulted in 2,507 important features for pipeline D1 (DSD-min), 2198 for D2 (KL-min), 2,263 for D3 (KL-med), 1,655 for D4 (JS-min), and 1,817 for D5 (JS-med). Important features are those with non-zero importance value as characterized by the Regressor model.

Once the important features/nodes are extracted, we search this space to identify the explanatory network of each set of drug targets. To do so, we rank the similarity terms of each target and the corresponding seeds on the space of important features and identify the nodes with the highest contribution to the similarity measure such that they satisfy the following equation:

$$\log_{10}\!\left(\frac{l}{term_i}\right) \le 1, \; l = \max(term_i), \; i \in V \qquad (14)$$

If a drug has multiple targets or if each target has multiple corresponding seeds (seeds with the same similarity to a target), the results are aggregated. The explanatory network of a target that happens to be a seed is that seed itself.

FIGS. 8A-8D shows the similarities and differences among the explanatory subgraphs of the different prediction pipelines.

Example 15. Network Properties of Prediction Algorithms—Complementarity of Prediction Algorithms (FIG. 2C)

To investigate the complementarity among the prediction algorithms, for each drug we measured the network separation $S_{G-d}$ between the explanatory subgraph G and the drug's targets (d), and the separation $S_{G-v}$, between G and the 332 SARS-Cov2 viral targets (v) capturing the disease module. Each drug has twelve subgraphs, each corresponding to one of the twelve pipelines. A total of 320 drugs, for which all pipelines have predictive subgraph and separation values, are shown in FIGS. 9A-9D. Proximity Pipeline 3 uses differentially expressed genes as input drug data; thus, for proximity P3 we computed the separation between the subgraph and the differentially expressed genes. The figure shows complementarily patterns between methods: the AI pipelines extracts their predictions from subgraphs that overlap with the drug targets ($S_{G-d} < 0$), but are separated from the COVID-19 module ($S_{G-v} < 0$); proximity-based methods show the opposite pattern—for most of the predictive subgraphs the overlap with the COVID-19 module is apparent ($S_{G-v} < 0$; by contrast, diffusion-based predictive subgraphs avoid both the drug targets and the disease module ($S_{G-d} < 0$, $S_{G-v} < 0$).

Example 16. Experimental Validation—Cell Cultivation and Viruses Used

VeroE6 cells were obtained from ATCC (Manassas, VA, USA) and maintained in DMEM supplemented with 10% Fetal bovine serum (FBS) at 37° C. in a humidified CO2 incubator. The virus strain used was isolated from a traveler returning to Washington State, USA, from Wuhan, China, (USA-WA1/2020) and was obtained from BEI resources (Manassas, VA, USA). The virus stock was passaged twice on Vero cells by challenging the cells at an MOI of less than 0.01 and incubating until cytopathology was seen (typically 3 d after inoculation). A sample of the culture supernatant was sequenced by next generation sequencing (NGS) and was consistent with the original isolate without evidence of other virus or bacterial contaminants. The virus stock was stored at −80° C. The virus stock was serially passaged as above several times further on Huh7 cells for use in Huh7 cell infection assays.

High Throughput Virus Infection Inhibition Assay (E918). To evaluate the efficacy of a large library of compounds against SARS-CoV-2 infection, a high throughput screen of >6700 compounds was performed as described in Patten et al. In short, compounds were pre-spotted into 384 well plates and diluted in culture medium before being added to VeroE6 cells. The dilution scheme was a four-point ten-fold series, with final concentrations ranging from 8 uM to 8 nM. Compounds were incubated on cells for more than an hour, then challenged with virus at an MOI of about 0.2. After a 1-1.5 day incubation, cells were treated with 10% buffered formalin for at least 6 hours, washed in PBS, and virus antigen stained with SARS-CoV-2 specific antibody (Sino Biologicals, MM05) together with Hoechst 33342 dye to stain cell nuclei. Plates were imaged by a Biotek Cytation 1 microscope, and automated image analysis was used to count total number of infected cells and total cell nuclei. CellProfiler software (Broad Institute, MA, USA) was used for image analysis using a customized processing pipeline (available upon request to RAD). Infection efficiency was calculated as the ratio of infected cells to total cell nuclei, and was normalized to negative controls. Loss of cell nuclei was used to flag treatments suggestive of host cell toxicity. Compounds were classified by DRC as described below. The assay was performed in duplicate.

Example 17. Experimental Validation—Follow Up Virus Infection Assay (E74)

For further evaluation of small molecule efficacy against infection with wild type SARS-CoV-2 virus, compounds were first dissolved to 10 mM in DMSO and then diluted into culture medium before addition to cells. The compound stock was added to VeroE6 cells incubated for a minimum of 1 hour and then challenged with virus at a MOI of about 0.2. Dosing ranged from a final concentration of 25 μM down to 0.2 μM in a two-fold dilution series. As a positive control, 5 μM E-64 was used as it was previously reported to inhibit SARS-CoV-2 infection (Hoffman et al. 2020). Negative controls were <0.5% DMSO. Plates were processed as described above. Each assay was performed in duplicate in 384 well plates.

Example 18. Experimental Validation—Drug-Response Classification

The classification of the drug-response outcomes was done using a drug response curve (DRC) model. We used the R package drc to calculate the DRCs using a log-logistic model with four parameters (hill, IC50, min, and max). Each drug-response was classified in two steps: first inspecting toxicity and later evaluating the drug effect on the inhibition of viral proliferation.

To inspect the cytotoxicity, we first estimated the model parameters using as response variable the nuclei count in the treated cells, normalized by the nuclei count in the controls. We tested the dose-response effect for all drugs using a $\chi^2$ test for goodness of fit and drugs with p<0.01 (Bonferroni correction) were defined as cytotoxic, with the exception of drugs demonstration toxicity only at the highest dose. To evaluate inhibition of viral replication, we used as response for the DRC model the number of infected cells in the treated samples normalized by the controls. For that, a drug was considered to have a dose-response effect by using a $\chi^2$ test for goodness of fit (p<0.01, Bonferroni correction), and the significant drugs were defined as Strong (S) or Weak (W) if the viral reduction was greater than 80% and 50%, respectively. The drugs that did not meet the criteria for S or W were classified as no-effect (N). Finally, we classified drugs as cytotoxic (C) if their toxicity curves were greater than their viral proliferation curves in at least half of the doses tested.

Example 19. Experimental Validation—Huh7 Confirmation

We validated the outcomes for the top 200 ranked drugs with S&W response in the Huh7 cell line (human liver cell line). Drug dosing and infection were performed as described above, with remdesivir being used as a positive control. We found that six drugs had a positive response, and four of them (digoxin, fluvastatin, azelastine, and auranofin) are in a suitable dose bioavailability range (FIGS. 10 and 11). Even though auranofin and azelastine showed tracing cytotoxicity in Huh7 cells, in high concentration, the dose range where they are reducing nuclei count are inside pharmacological usage range, moreover, auranofin has been in used for treating asthma. Furthermore, our prediction has been confirmed not only by our in vitro assays, but also by a contemporaneous set of in vivo experiments performed after we locked in our ranking results.

Example 20. Experimental Validation—Biological Interpretation of Effective Drugs in E918 Dataset We observed 77 drugs that showed strong (S) or weak effects (W) in the high-throughput screening. There was no drug category (ATC Classification) that was enriched among the S, W, or S&W drugs (hypergeometric test FDR-BH padj>0.05). To search for common patterns that could explain their bioactivity, we performed hierarchical clustering on the drug target profiles, failing to find binding patterns shared by all drugs (FIG. 12). Only four small groups of drugs are observed, documenting various degrees of shared targets (FIG. 12), three of which contain drugs from multiple categories, and one group consists of 7 nervous system-related drugs with similar target profiles. We also performed pathway enrichment analysis to identify biological processes shared across the targets of drugs with strong or weak effects. Among the 77 S&W drugs, 42 are located in three groups associated with common pathways, and 20 of these drugs are of diverse indications linked to transport and metabolism of different substrates. Eighteen are associated with pathways related to membrane receptors, most of them indicated for nervous system disorders, targeting G protein-coupled receptors such as ADRA1A, HTR2A, and HRH1 (FIG. 13). Taken together, neither the pathway nor the target analysis reveals patterns that could explain the efficacy of the 77 S&W drugs.

Example 21. Statistical Validation—Performance Evaluation Using ROC Curves, Precision, and Recall We examined whether positive drugs (e.g., strong-effect drugs) were ranked high by measuring the predictive power of each pipeline in terms of area under the ROC (Receiver Operating Characteristics) curve, precision, and recall. First, we calculated ROC (Receiver Operating Characteristics) curves and AUC (area under the curve) scores for model selection and performance analysis. The AUC score measures the separation between positive examples (e.g., drugs with strong or weak responses) and negative examples (e.g., drugs showing no-effect in experimental screening). For the ranked lists of drugs, we applied different thresholds to compute false-positive and true-positive rates to plot the ROC curves. Scores of AUC range between 0 and 1, where 1 corresponds to perfect performance and 0.5 indicates the performance of a random classifier. We used the R package ROCR for computing the AUC scores and ggplot2 plotting the ROC curves.

The AUC metric operates on the whole ranked list of drugs, and thus it does not directly reflect the ability of the method to prioritize most promising drug candidates at the top of the list. To address this issue and account for unbalanced ground-truth information where negative examples vastly outnumber positives, we also considered hit-rate based metrics to evaluate the quality of top-K drugs in each ranked list. Here, we evaluated performance at a given cut-off rank K, considering only the topmost predictions by the pipeline. In particular, we calculated the fraction of top-K ranked drugs that were positive outcomes (precision at K) and the fraction of all positive outcomes that were among the top-K ranked drugs (recall at K).

We considered four types of ground-truth information to evaluate prediction performance: 1) The outcome of the experimental screening of 918 compounds (E918 dataset). We identified 806 no effect drugs, 40 with weak effect, and 37 with strong effect. 2) The outcome of the experimental screening of additional 74 compounds tested with a wider range of doses (0.625-20 μM, 0.2 MOI) (E74 dataset) (FIGS. 14A-14H). The E74 dataset represents a subset of 81 compounds by a medical doctor among the top 10% of all drug predictions that were available for purchase. We identified 39 no effect drugs, 10 with weak effect, and 11 with strong effect. 3) 67 drugs that, as of April 2020, were in ongoing trials for COVID-19, obtained from the ClinicalTrials.gov website (CT415 dataset). ClinicalTrials.gov organizes COVID-19 specific collection of all trials. Trial records consist of information on inclusion and exclusion criteria, details on drugs being tested, the scientific team behind the study, and funding agencies. We extract drug names from clinical trials' treatment information and match their names with records on the DrugBank database. 4) We also collected clinical trials data at the experimental readout time Jun. 15, 2020 (C615 dataset).

Note that some methods do not provide prediction for every drug in the full dataset. While that would make a fair comparison of the methods challenging, we note that ground-truth information described above is available for drugs predicted by all pipelines (except for P3, hence it is harder to compare this pipeline with the other 11). Finally, we note that we adopted a conservative approach by evaluating predictive performance using the rankings across all 6,340 drugs, not only 918 experimentally screened drugs. For example, it is possible to conceive that a particular topmost prediction in a pipeline represents a positive drug, however, that is impossible to know if the predicted drug was not included in experimental screening. Because of that, the reported precision and recall values represent conservative estimates of prediction performance, i.e., the values are lower than what one could obtain if the analysis was limited to only experimentally screened drugs. To determine the significance of predictive power, we calculated the expected number of positive drugs among top-K drugs for each pipeline and compared the expected values with the observed precision and recall values. To this end, we calculated the expected number of positive drugs by taking into account (a) the number of drugs for which ground-truth information is available, and (b) the number of drugs for which a pipeline makes predictions. We used an exact one-tailed binomial test (p-value<0.05) to test whether a top-K list returned by a pipeline is biased towards containing more positive drugs than what we would expect on average by pure chance had the ranking be a random one.

Example 22. Statistical Validation—Rank Aggregation Algorithms (RAAs)

Rank aggregation is concerned with how to combine several independently constructed rankings into one final ranking that represents a consensus ranking, i.e., a collective opinion of prediction methods that is representative of all rankings returned by the methods. The classical consideration for specifying the final ranking is to maximize the number of pairwise agreements between the final ranking and each input ranking. Unfortunately, this objective, known as the Kemeny consensus, is NP-hard to compute, which has motivated the development of methods that either use heuristics or approximate the Kemeny optimal ranking.

Example 23. Statistical Validation—Average Rank Method

The Average Rank method follows the most straightforward way to integrate multiple rankings. For each drug, it calculates a simple rank average over 12 rankings returned by the pipelines to obtain the overall ranking. While the Average Rank method is a popular ad-hoc rank aggregation strategy, many studies, including ours, found that studying the average ranks can be a poor aggregation approach. Next, we briefly overview methods that realize more sophisticated approaches to obtain the overall ranking.

Borda Method

Example 24. Statistical Validation—Borda Method

The Borda method is one of most commonly used rank aggregation methods. Briefly, the method proceeds as follows. Given are k rankings exist, $R_1, R_2 \ldots, R_k$. For each drug $\alpha \epsilon R_1, \alpha$ is assigned a score $B_i(\alpha)$ equal to the number of drugs that $\alpha$ outranks in ranking $R_1$ The Borda count $B(\alpha)$ of drug $\alpha$ is then calculated as $$\sum_{i}^{k} = _{i}^{B} (\alpha).$$

Finally, drugs are sorted in the descending order based on their Borda counts to create a consensus ranking. Theoretically, Borda method offers a guarantee on approximating Kemeny consensus. In particular, Borda method is a 5-approximation algorithm of the Kemeny optimal ranking. We used the Python package rank aggregation for computing the Borda ranking.

Example 25. Statistical Validation—Dowdall Method

The Dowdall method is a modified form of the Borda method that has been widely used in political elections in many countries. Intuitively, individual pipelines make predictions for drugs, which are interpreted as preferences of the pipeline. For a pipeline, its $1^{st}$ choice gets a score of 1, its $2^{nd}$ choice get $\frac{1}{2}$, its $3^{rd}$ choice gets $\frac{1}{3}$, and so on. Drug with the largest total score across pipelines wins. Formally, let be given k rankings, $R_1, R_2 \ldots, R_k$. For each drug $\alpha \epsilon R_1, \alpha$ is first assigned a score $D_i(\alpha)$ equal to the reciprocal of drug's rank in ranking $R_i$ The total score $D(\alpha)$ is then calculated as $$\sum_{i}^{k} = _{i}^{D} (\alpha).$$

Candidates are sorted in descending order based on their total score to create a consensus ranking.

Example 25. Statistical Validation—CRank

The CRank algorithm starts with ranked lists of drugs, $R_r$, each one arising from a different pipeline, r. Each ranked list is partitioned into equally sized groups, called bags. Each bag i in ranked list $R_r$ has attached importance weight $$K_r^i$$

whose initial values are all equal. CRank uses a two-stage iterative procedure to aggregate the individual rankings by taking into account uncertainty that is present across ranked lists. After initializing the aggregate ranking R as a weighted average of ranked lists $R_r$, CRank alternates between the following two stages until no changes were observed in the aggregated ranking R. (1) First, it uses the current aggregated ranking R to update the importance weights $$K_r^i$$

for each ranked list. For that purpose, the top ranked drugs in R serve as a temporary gold standard. Given bag i and ranked list $R_r$, CRank updates importance weight $$K_r^i$$

based on how many drugs from the temporary gold standard appear in bag i using Bayes factors. (2) Second, the ranked lists are re-aggregated based on the importance weights calculated in the previous stage. The updated importance weights are used to revise R in which the new rank R(α) of drug α is expressed as:

$$R(\alpha) = \sum_r K_r^{ir(\alpha)} R_r(\alpha), \text{ where } K_r^{ir(\alpha)}$$

indicates the importance weight of bag $i_r(\alpha)$ of drug α for ranking r, and $R_r(\alpha)$ is the rank of α according to r. By using an iterative approach, CRank allows for the importance of a ranked list returned by an individual pipeline not to be predetermined, i.e., a-priori fixed, and to vary across drugs. The final output is a global ranked list R of drugs that represents the collective opinion of all drug repurposing prediction algorithms. In all experiments, we set the number of bags to 1,000, the size of the temporary gold standard to 0.5% of the total number of drugs in R, and the maximum number of iterations to 50. In all cases, the algorithm converged, in fewer than 20 iterations. The Python source code implementation of CRank is available at github.com/mims-harvard/crank (raa.py).

Example 26. Statistical Validation—Comparison of RAAs

What explains CRank's outstanding performance across all datasets? Each RAA aims to approximate the optimal Kemeny consensus, which offers the best agreement with all 12 prediction pipelines. As this consensus remains unknown (NP-hard), we cannot assess how well the different RAA methods approximate it. We do, however, have a ground-truth ranking, offered by the experimental and clinical datasets (E918 and CT415). We assigned rank 1 to the strong drugs, rank 2 to the weak drugs, and rank 3 to the no-effect drugs, allowing us to measure the Kemeny score for each aggregated list, representing the fraction of pairwise disagreements between the respective ranked list and the experimental outcomes. For K=100, the Kemeny score of the Average Rank method is infinite for E918, as there are no positive drugs among the top 100. In contrast, for the Borda count, we obtain a Kemeny score of KS=0.7131, indicating that 71% of all drug pairs in the ranked list of Borda method disagrees with the ground-truth ranking in the E918 dataset. Note that the theoretical expectation for a purely random ranking is KS=0.5, meaning that 50% of all drug pairs in the random reference are flipped, i.e., while with KS=0.4545 Dowdall does better than random, we observe a much lower KS=0.2679 for CRank. We measured the Kemeny score for multiple values, for both datasets (E918 and CT415), finding that for K<250 (top drugs), CRank offers the best agreement with the outcomes.

What is claimed is:
1. A multi-modal system for generating drug repurposing predictions for a disease caused by a pathogen, comprising:

a protein-protein interaction network defining pathogen-protein interactions for the pathogen and drug-protein interactions for a plurality of candidate drugs;
a graph neural network comprising an embedded representation of the protein-protein interaction network, the embedded representation including candidate drug nodes and disease nodes, the graph neural network configured to predict new edges between the candidate drug nodes and disease nodes to produce a decoded embedding space, a first list comprising a subset of the plurality of candidate drugs being identifiable from the decoded embedding space; and
a processor, the processor configured to:
determine a diffusion metric for pairs of nodes in the protein-protein interaction network, each pair comprising a pathogen-protein node and a drug-protein node, a second list comprising a subset of the plurality of candidate drugs being identifiable from the determined diffusion metric;
determine a proximity distance for pairs of nodes in the protein-protein interaction network, each pair comprising a pathogen-protein node and a drug-protein node, a third list comprising a subset of the plurality of candidate drugs being identifiable from the determined proximity distances; and
generate a ranked list of candidate drugs predicted to be effective in treatment of the disease based on the first, second, and third lists.
2. The system of claim 1, wherein the processor is further configured to generate the ranked list based on a consensus ranking of the first, second, and third lists.
3. The system of claim 1, wherein the first list comprises at least two sub-lists, each sub-list generated based on varying decoding parameters applied to the decoded embedding space.
4. The system of claim 1, wherein the graph neural network is untrained for the pathogen.
5. The system of claim 4, wherein the graph neural network is a graph convolutional neural network trained by a zero-shot learning strategy.
6. The system of claim 1, wherein the diffusion metric is a diffusion state distance between nodes, a divergence between vector representations of nodes, or a combination thereof.
7. The system of claim 6, wherein the second list comprises at least two sub-lists, each sub-list generated based on varying distance or divergence parameters.
8. The system of claim 1, wherein the third list comprises at least two sub-lists, each sub-list generated based on varying drug-inclusion criteria.
9. The system of claim 1, wherein the protein-protein interaction network is a human interactome.
10. A multi-modal method for generating drug repurposing predictions for a disease related to a pathogen, comprising:
with a protein-protein interaction network defining pathogen-protein interactions for the pathogen and drug-protein interactions for a plurality of candidate drugs:
in a graph neural network comprising an embedded representation of the protein-protein interaction network, the embedded representation including candidate drug nodes and disease nodes:
predicting new edges between the candidate drug nodes and disease nodes to produce a decoded embedding space, and identifying a first list comprising a subset of the plurality of candidate drugs being from the decoded embedding space;

by a processor:

determining a diffusion metric for pairs of nodes in the protein-protein interaction network, each pair comprising a pathogen-protein node and a drug-protein node, identifying a second list comprising a subset of the plurality of candidate drugs from the determined diffusion metric;

determining a proximity distance for pairs of nodes in the protein-protein interaction network, each pair comprising a pathogen-protein node and a drug-protein node, identifying a third list comprising a subset of the plurality of candidate drugs from the determined proximity distances; and generating a ranked list of candidate drugs predicted to be effective in treatment of the disease based on the first, second, and third lists.

11. The method of claim 10, wherein generating the ranked list includes consensus ranking of the first, second, and third lists.

12. The method of claim 10, wherein identifying the first list comprises identifying at least two sub-lists, each sub-list generated based on varying decoding parameters applied to the decoded embedding space.

13. The method of claim 10, wherein the graph neural network is untrained for the pathogen.

14. The method of claim 13, wherein the graph neural network is a graph convolutional neural network trained by a zero-shot learning strategy.

15. The method of claim 10, wherein the diffusion metric is a diffusion state distance between nodes, a divergence between vector representations of nodes, or a combination thereof.

16. The method of claim 15, wherein identifying the second list comprises identifying at least two sub-lists, each sub-list generated based on varying distance or divergence parameters.

17. The method of claim 10, wherein identifying the third list comprises identifying at least two sub-lists, each sub-list generated based on varying drug-inclusion criteria.

18. A method of improving accuracy of drug repurposing predictions for a disease caused by a pathogen, comprising:

with a protein-protein interaction network defining pathogen-protein interactions for the pathogen and drug-protein interactions for a plurality of candidate drugs:

in a graph neural network comprising an embedded representation of the protein-protein interaction network, the embedded representation including candidate drug nodes and disease nodes:

predicting new edges between the candidate drug nodes and disease nodes to produce a decoded embedding space, and identifying a first list comprising a subset of the plurality of candidate drugs being from the decoded embedding space;

by a processor:

determining a diffusion metric for pairs of nodes in the protein-protein interaction network, each pair comprising a pathogen-protein node and a drug-protein node, identifying a second list comprising a subset of the plurality of candidate drugs from the determined diffusion metric;

determining a proximity distance for pairs of nodes in the protein-protein interaction network, each pair comprising a pathogen-protein node and a drug-protein node, identifying a third list comprising a subset of the plurality of candidate drugs from the determined proximity distances; and generating a consensus ranking of candidate drugs predicted to be effective in treatment of the disease based on the first, second, and third lists, the consensus ranking providing for improved predictive power over each of the first, second, and third lists.

* * * * *